US008329189B2

(12) United States Patent
McBride et al.

(10) Patent No.: US 8,329,189 B2
(45) Date of Patent: Dec. 11, 2012

(54) **IMMUNOREACTIVE *EHRLICHIA* P120/P140 EPITOPES AND USES THEREOF**

(75) Inventors: Jere W. McBride, League City, TX (US); Tian Luo, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 79 days.

(21) Appl. No.: 12/769,352

(22) Filed: Apr. 28, 2010

(65) Prior Publication Data

US 2010/0273194 A1  Oct. 28, 2010

Related U.S. Application Data

(60) Provisional application No. 61/173,345, filed on Apr. 28, 2009.

(51) Int. Cl.
*A61K 39/02* (2006.01)
*C12N 1/20* (2006.01)

(52) U.S. Cl. ............... 424/190.1; 424/184.1; 435/252.8; 435/810

(58) Field of Classification Search .................. None
See application file for complete search history.

(56) References Cited

U.S. PATENT DOCUMENTS 6,015,691 A    1/2000 Walker et al. ............... 435/69.1
6,043,085 A *  3/2000 Yu et al. ........................ 435/325

FOREIGN PATENT DOCUMENTS

WO      WO 00/12688          3/2000
WO      WO2006138509 A2 *  12/2006
WO      WO2008043000 A2 *   4/2008
WO      WO 2008/112007       9/2009

OTHER PUBLICATIONS

"*E. canis* 120 kDa protein repeat unit," Database Geneseq [Online], EBI accession No. GSP:AAY57278, Jun. 6, 2000.
"*E. chaffeensis* 120 kDa protein repeat unit," Database Geneseq [Online], EBI accession No. GSP:AAY57277, Jun. 6, 2000.
"*E. chaffeensis* gp120 immunogenic gragment SEQ ID No. 28 (from WO2006138509)," EBI accession No. GSP:AEN67779, Apr. 5, 2007.
"*Ehrlichia canis* str. Jake gp140 immunogenic fragment SEQ ID No. 27 (from WO2006138509)," EBI accession No. GSP:AEN67778, Apr. 5, 2007.
Harrus et al., "Comparison of three enzyme-linked immunosorbant assays with the indirect immunofluorescent antibody test for the diagnosis of canine infection with *Ehrlichia canis*," *Veterinary Microbiology*, 86(4):361-368, 2002.
Luo et al., "Major species-specific antibody epitopes of the *Ehrlichia chaffeensis* p120 and *E. canis* p140 orthologs in surface-exposed tandem repeat regions," *Clinical and Vaccine Immunology*, 16(7):982-990, 2009.
PCT International Search Report and Written Opinion, issued in International application No. PCT/US2010/032744, mailed Aug. 11, 2010.

Carpenter et al., "The Incidence of Ehrlichial and Rickettsial Infection in Patients with Unexplained Fever and Recent History of Tick Bite in Central North Carolina"., *J. Infect. Dis.*, 180:900-903, 1999.
Chen et al, "Identification of the Antigenic Constituents of *Ehrlichia chaffeensis*," *Am. J. Trop. Med. Hyg.*, 50:52-58, 1994.
Chen et al., "Western immunoblotting analysis of the antibody responses of patients with human monocytotropic ehrlichiosis to different strains of *Ehrlichia chaffeensis* and *Ehrlichia canis*," *Clin. Diagn. Lab Immunol.*, 4:731-735, 1997.
Childs et al., "Outcome of Diagnostic Tests Using Samples from Patients with Culture-Proven Human Monocytic Ehrlichiosis: Implications for Surveillance" *J. Clin. Microbiol.*, 37:2997-3000, 1999.
Collins et al., "The genome of the heartwater agent *Ehrlichia ruminantium* contains multiple tandem repeats of actively variable copy number," *Proc. Natl. Acad. Sci. USA*, 102(3):838-43, 2005.
Comer et al., "Serologic Testing for Human Granulocytic Ehrlichiosis at a National Referral Center," *J. Clin. Microbiol.*, 37:558-564, 1999.
Doyle et al., "Differentially Expressed and Secreted Major Immunoreactive Protein Orthologs of *Ehrlichia canis* and *E. chaffeensis* Elicit Early Antibody Responses to Epitopes on Glycosylated Tandem Repeats," *Infect. Immun.*, 74:711-720, 2006.
Dumler et al, "Ehrlichioses in Humans: Epidemiology, Clinical Presentation, Diagnosis, and Treatment,"*Clin. Infect. Dis.* 45:S45-S51, 2007.
Feng and Walker, "Mechanisms of Immunity to *Ehrlichia muris*: a Model of Monocytotropic Ehrlichiosis," *Infect. Immun.*, 72:966-971, 2004.
Frutos et al., "Comparative genomics of three strains of *Ehrlichia ruminantium*: a review," *Ann. NY. Acad. Sci.*, 1081:417-33, 2006.
Hotopp et al. "Comparative Genomics of Emerging Human Ehrlichiosis Agents," *PLoS Genet.* 2(2):e21, 2006.
Luo et al., "A Variable-Length PCR Target Protein of *Ehrlichia chaffeensis* Contains Major Species-Specific Antibody Epitopes in Acidic Serine-Rich Tandem Repeats," *Infect. Immun.*, 76:1572-1580, 2008.
Luo et al., "Molecular Characterization of Antibody Epitopes of *Ehrlichia chaffeensis* Ankyrin Protein 200 and Tandem Repeat Protein 47 and Evaluation of Synthetic Immunodeterminants for Serodiagnosis of Human Monocytotropic Ehrlichiosis ," *Clinical and Vaccine Immunology*, 17(1):87-97, 2010, Published ahead of print on Dec. 2, 2009.
Mavromatis et al , "The Genome of the Obligately Intracellular Bacterium *Ehrlichia canis* Reveals Themes of Complex Membrane Structure and Immune Evasion Strategies,"*J. Bacteriol.*, 188(11):4015-4023, 2006.
McBride et al, "Identification of a Glycosylated *Ehrlichia canis* 19-Kilodalton Major Immunoreactive Protein with a Species-Specific Serine-Rich Glycopeptide Epitope," *Infect. Immun.*, 75:74-82, 2007.
McBride et al., "Glycosylation of Homologous Immunodominant Proteins of *Ehrlichia chaffeenis* and *Ehrlichia canis*", *Infection and Immunity*, 68:13-18, 2000.

(Continued)

*Primary Examiner* — Padma Baskar
(74) *Attorney, Agent, or Firm* — Parker Highlander PLLC

(57) ABSTRACT

Provided herein are immunoreactive peptides which can selectively bind *Ehrlichia*-specific anti-p120 or anti-p140 antibodies. Methods and kits utilizing the immunoreactive peptides are also provided. The immunoreactive peptides may be utilized, e.g., for determining whether or not a subject is infected with *Ehrlichia chaffeensis* or *Ehrlichia canis*. In certain embodiments, the immunoreactive peptides may be utilized in an ELISA or lateral flow assay.

17 Claims, 14 Drawing Sheets

OTHER PUBLICATIONS

McBride et al., "PCR detection of acute *Ehrlichia canis* infection in dogs," *J Vet. Diagn. Invest.*, 8:441-447, 1996.

McBride et al., "Glycosylation of Homologous Immunodominant Proteins of *Ehrlichia chaffeensis* and *Ehrlichia canis*," *Infect. Immun.*, 68:13-18, 2000.

McBride et al., "Kinetics of Antibody Response to *Ehrlichia canis* Immunoreactive Proteins," *Infect. Immun.*, 71:2516-2524, 2003.

Nethery et al., "*Ehrlichia canis* gp200 Contains Dominant Species-Specific Antibody Epitopes in Terminal Acidic Domains," *Infect. Immun.*, 75:4900-4908, 2007.

Paddock and Childs, "*Ehrlichia chaffeensis*: a Prototypical Emerging Pathogen," *J. Clin. Microbiol.*, 16:37-64, 2003.

Popov et al., "The 120 kDa outer membrane protein of *Ehrlichia chaffeensis*: Preferential expression on dense-core cells and gene expression in *Escherichia coli* associated with attachment and entry," *Microb. Pathog.*, 28:71-80, 2000.

Rikihisa et al., Western immunoblot analysis of *Ehrlichia chaffeensis, E. canis,* or *E. ewingii* infections in dogs and humans. *J. Clin. Microbiol.*, 32:2107-2112, 1994.

Storey et al., "Molecular cloning and sequencing of three granulocytic *Ehrlichia* genes encoding high-molecular-weight immunoreactive proteins," *Infect. Immun.*, 66:1356-1363, 1998.

Sumner et al., "Molecular Cloning and Characterization of the *Ehrlichia chaffeensis* Variable-Length PCR Target: an Antigen-Expressing Gene That Exhibits Interstrain Variation," *J Clin Microbiol.* 37(5):1447-53, 1999.

Unver et al., "Western blot analysis of sera reactive to human monocytic ehrlichiosis and human granulocytic ehrlichiosis agents," *J. Clin. Microbiol.*, 39(11):3982-6, 2001.

Walker and Task Force on Consensus Approach for Ehrlichiosis, In: *Diagnosing human ehrlichioses: current status and recommendations*, ASM News, 66:287-290, 2000.

Winslow et al., "Antibody-mediated elimination of the obligate intracellular bacterial pathogen *Ehrlichia chaffeensis* during active infection," *Infect. Immun.*, 68:2187-2195, 2000.

Winslow et al., "Immunity to the ehrlichiae: new tools and recent developments," *Curr. Opin. Infect. Dis.*, 18:217-221, 2005.

Yabsley et al., "Molecular variation in the variable-length PCR target and 120-kilodalton antigen genes of *Ehrlichia chaffeensis* from white-tailed deer (*Odocoileus virginianus*)," *J. Clin. Microbiol.*, 41:5202-5206, 2003.

Yager et al., "Essential role for humoral immunity during *Ehrlichia* infection in immunocompetent mice," *Infect. Immun.*, 73:8009-8016, 2005.

Yu et al., Molecular Cloning and Characterization of the 120-Kilodalton Protein Gene of *Ehrlichia canis* and Application of the Recombinant 120-Kilodalton Protein for Serodiagnosis of Canine Ehrlichiosis, *Journal of Clinical Microbiology*, 38(1):369-374, 2000.

Yu et al., "The Recombinant 120-Kilodalton Protein of *Ehrlichia chaffeenis*, a Potential Diagnostics Tool", *Journal of Clinical Microbiology*, 34:2853-2855, 1996.

Yu et al., "Cloning and sequencing of the gene for a 120-kDa immunodominant protein of *Ehrlichia chaffeensis*," *Gene*, 184:149-154, 1997.

Zhang et al., "Genetic and antigenic diversities of major immunoreactive proteins in globally distributed *Ehrlichia canis* strains," *Clin. Vaccine Immunol.*, 15:1080-1088, 2008.

* cited by examiner

```
p120R  SSSEPFVAS--SEVSKVEQEETNPEVIINDLQDVAS
p140R  SSSE--VGEKVSETSN---EESTPEVKAEDLGNIVD p120N  MDIDNSNISTADIKSNILGLIDIIMRIILGFGN
p140N  MDIDNNNVTTSSTDKSQNLMEVIMRIINFGN p120C  GQYSLGIEMAMYGFQLVKDLLGGLISNUPVG-LNVSLYRMERNVFTNHS
p140C  GEHVIMYGIYVVPVQSVKDISIVENIDHSTEDCNLDVYFVGTNSFTNKE
```

FIG. 2

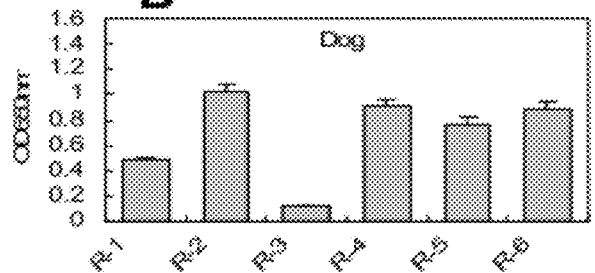
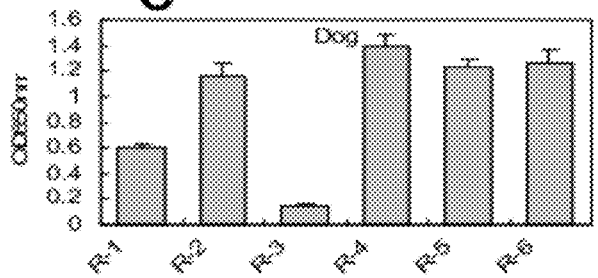
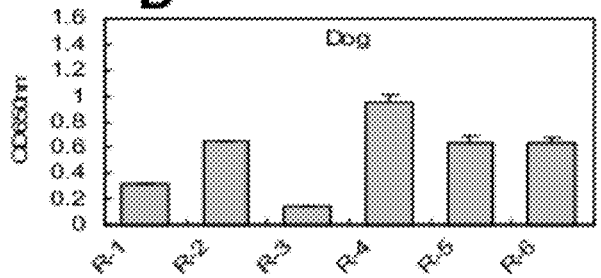
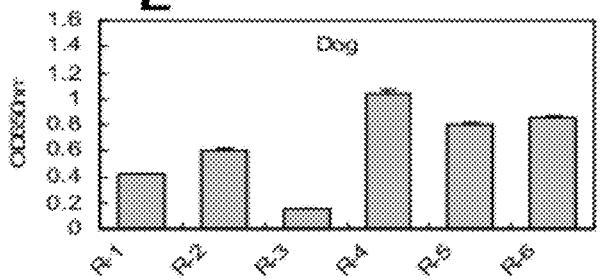
FIG. 6

A
TRP47-N4 (44 aa)
                HHNEHDHDAHGRGAASSVAEGVGSAISQILSLSDSIVVPVLEGN
    1 (22)      HHNEHDHDAHGRGAASSVAEGV
    2 (22)                RGAASSVAEGVGSAISQILSLS
    3 (22)                        GSAISQILSLSDSIVVPVLEGN
TRP47-R(19)  ASVSEGDAVVNAVSQETPA
TRP47-C(26)  TQPQSRDSLLHEEDMAAQFGNRYFYF
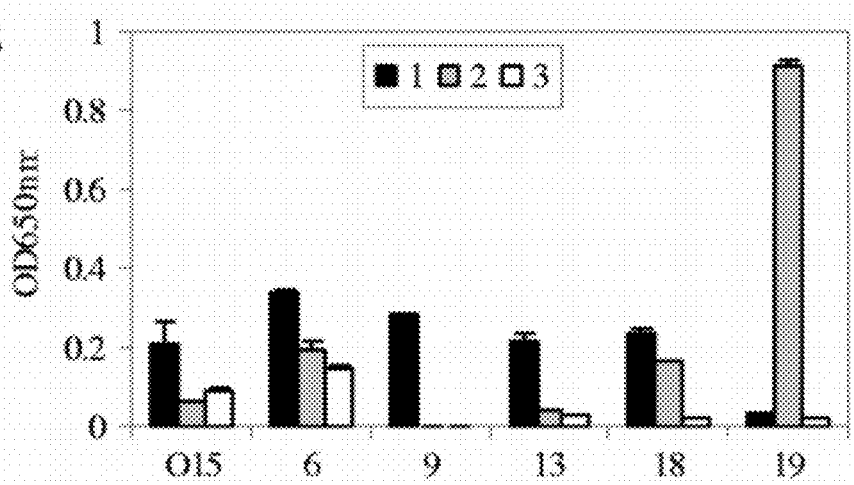
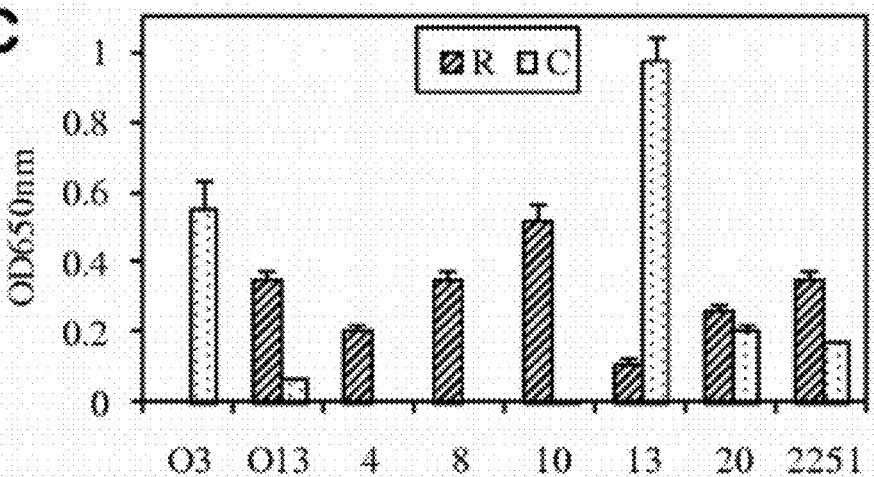
FIGS. 12A-C

SEQUENCE LISTING

```
<160> NUMBER OF SEQ ID NOS: 123

<210> SEQ ID NO 1
<211> LENGTH: 22
<212> TYPE: PRT
<213> ORGANISM: Artificial Sequence
<220> FEATURE:
<223> OTHER INFORMATION: Synthetic peptide

<400> SEQUENCE: 1

Ser Lys Val Glu Gln Glu Glu Thr Asn Pro Glu Val Leu Ile Lys Asp
1               5                   10                  15

Leu Gln Asp Val Ala Ser
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic peptide

<400> SEQUENCE: 2
```

```
Ser Lys Glu Glu Ser Thr Pro Glu Val Lys Ala Glu Asp Leu Gln Pro
1               5                   10                  15

Ala Val Asp

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Glu Gln Glu Glu Thr Asn Pro Glu Val Leu Ile Lys
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Ser Lys Val Glu Gln Glu Glu Thr Asn Pro Glu Val Leu Ile Lys Asp
1               5                   10                  15

Leu

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Glu Gln Glu Glu Thr Asn Pro Glu Val Leu Ile Lys Asp Leu Gln Asp
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Glu Thr Asn Pro Glu Val Leu Ile Lys Asp Leu Gln Asp Val Ala
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Synthetic peptide

<400> SEQUENCE: 7

Ser Ser Ser Glu Val Gly Lys Lys Val Ser Thr Ser Lys Glu Glu
1               5                   10                  15

Ser Thr Pro

<210> SEQ ID NO 8
<211> LENGTH: 19
<212> TYPE: PRT
<213> ORGANISM: Artificial Sequence
<220> FEATURE:
```

-continued

```
<223> OTHER INFORMATION: Synthetic peptide

<400> SEQUENCE: 8

Ser Glu Thr Ser Lys Glu Glu Ser Thr Pro Glu Val Lys Ala Glu Asp
1               5                   10                  15

Leu Gln Pro

<210> SEQ ID NO 9
<211> LENGTH: 14
<212> TYPE: PRT
<213> ORGANISM: Artificial Sequence
<220> FEATURE:
<223> OTHER INFORMATION: Synthetic peptide

<400> SEQUENCE: 9

Thr Pro Glu Val Lys Ala Glu Asp Leu Gln Pro Ala Val Asp
1               5                   10

<210> SEQ ID NO 10
<211> LENGTH: 19
<212> TYPE: PRT
<213> ORGANISM: Artificial Sequence
<220> FEATURE:
<223> OTHER INFORMATION: Synthetic peptide

<400> SEQUENCE: 10

Thr Pro Glu Val Lys Ala Glu Asp Leu Gln Pro Ala Val Asp Gly Ser
1               5                   10                  15

Ile Glu His

<210> SEQ ID NO 11
<211> LENGTH: 25
<212> TYPE: PRT
<213> ORGANISM: Artificial Sequence
<220> FEATURE:
<223> OTHER INFORMATION: Synthetic peptide

<400> SEQUENCE: 11

Glu His Ser Ser Ser Glu Val Gly Glu Lys Val Ser Lys Thr Ser Lys
1               5                   10                  15

Glu Glu Ser Thr Pro Glu Val Lys Ala
                20                  25

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Ser Lys Val Glu Gln Glu Glu Thr Asn Pro
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Asp Leu Gln Asp Val Ala Ser
1               5
```

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Ser Lys Glu Glu Ser Thr Pro
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Glu Asp Leu Gln Pro Ala Val Asp
1               5

<210> SEQ ID NO 16
<211> LENGTH: 29
<212> TYPE: DNA
<213> ORGANISM: Artificial Sequence
<220> FEATURE:
<223> OTHER INFORMATION: Synthetic primer

<400> SEQUENCE: 16
atggatattg ataatagtaa cataagtac                                    29

<210> SEQ ID NO 17
<211> LENGTH: 27
<212> TYPE: DNA
<213> ORGANISM: Artificial Sequence
<220> FEATURE:
<223> OTHER INFORMATION: Synthetic primer

<400> SEQUENCE: 17
tacaatatca tttactacat tgtgatt                                      27

<210> SEQ ID NO 18
<211> LENGTH: 29
<212> TYPE: DNA
<213> ORGANISM: Artificial Sequence
<220> FEATURE:
<223> OTHER INFORMATION: Synthetic primer

<400> SEQUENCE: 18
atggatattg ataatagtaa cataagtac                                    29

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
tgtgtcatct tcttgctctt g                                            21

<210> SEQ ID NO 20
<211> LENGTH: 25
<212> TYPE: DNA
<213> ORGANISM: Artificial Sequence
<220> FEATURE:
<223> OTHER INFORMATION: Synthetic primer

```
<400> SEQUENCE: 20
attctagtag aagatttgcc attag                                              25

<210> SEQ ID NO 21
<211> LENGTH: 27
<212> TYPE: DNA
<213> ORGANISM: Artificial Sequence
<220> FEATURE:
<223> OTHER INFORMATION: Synthetic primer

<400> SEQUENCE: 21
tacaatatca tttactacat tgtgatt                                            27

<210> SEQ ID NO 22
<211> LENGTH: 29
<212> TYPE: DNA
<213> ORGANISM: Artificial Sequence
<220> FEATURE:
<223> OTHER INFORMATION: Synthetic primer

<400> SEQUENCE: 22
atggatattg ataacaataa tgtgactac                                          29

<210> SEQ ID NO 23
<211> LENGTH: 27
<212> TYPE: DNA
<213> ORGANISM: Artificial Sequence
<220> FEATURE:
<223> OTHER INFORMATION: Synthetic primer

<400> SEQUENCE: 23
tattaaatca actgtttctt tgttagt                                            27

<210> SEQ ID NO 24
<211> LENGTH: 29
<212> TYPE: DNA
<213> ORGANISM: Artificial Sequence
<220> FEATURE:
<223> OTHER INFORMATION: Synthetic primer

<400> SEQUENCE: 24
atggatattg ataacaataa tgtgactac                                          29

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
tggatttcct acattgtcat tc                                                 22

<210> SEQ ID NO 26
<211> LENGTH: 19
<212> TYPE: DNA
<213> ORGANISM: Artificial Sequence
<220> FEATURE:
<223> OTHER INFORMATION: Synthetic primer

<400> SEQUENCE: 26
gaagtacagc ctgttgcag                                                     19

<210> SEQ ID NO 27
<211> LENGTH: 27
```

```
<212> TYPE: DNA
<213> ORGANISM: Artificial Sequence
<220> FEATURE:
<223> OTHER INFORMATION: Synthetic primer

<400> SEQUENCE: 27
tattaaatca actgtttctt tgttagt                                        27

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Ser Lys Glu Glu Ser
1               5

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
caacaaaatc ctaattcgca ag                                             22

<210> SEQ ID NO 30
<211> LENGTH: 22
<212> TYPE: DNA
<213> ORGANISM: Artificial Sequence
<220> FEATURE:
<223> OTHER INFORMATION: Synthetic primer

<400> SEQUENCE: 30
cgattttata tcattaccag ca                                             22

<210> SEQ ID NO 31
<211> LENGTH: 23
<212> TYPE: DNA
<213> ORGANISM: Artificial Sequence
<220> FEATURE:
<223> OTHER INFORMATION: Synthetic primer

<400> SEQUENCE: 31
caccatggca gatccaaaac aag                                            23

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
taccgcatac aatggatctt                                                20

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
```

```
caccccttta cctaaaggtc aaag                                              24

<210> SEQ ID NO 34
<211> LENGTH: 17
<212> TYPE: DNA
<213> ORGANISM: Artificial Sequence
<220> FEATURE:
<223> OTHER INFORMATION: Synthetic primer

<400> SEQUENCE: 34
atccctaaca ccttccc                                                      17

<210> SEQ ID NO 35
<211> LENGTH: 25
<212> TYPE: DNA
<213> ORGANISM: Artificial Sequence
<220> FEATURE:
<223> OTHER INFORMATION: Synthetic primer

<400> SEQUENCE: 35
caccgcagtt attcatgatg aagag                                             25

<210> SEQ ID NO 36
<211> LENGTH: 17
<212> TYPE: DNA
<213> ORGANISM: Artificial Sequence
<220> FEATURE:
<223> OTHER INFORMATION: Synthetic primer

<400> SEQUENCE: 36
caatggggat tgatttc                                                      17

<210> SEQ ID NO 37
<211> LENGTH: 23
<212> TYPE: DNA
<213> ORGANISM: Artificial Sequence
<220> FEATURE:
<223> OTHER INFORMATION: Synthetic primer

<400> SEQUENCE: 37
cacccatgtt atggttcaga acc                                               23

<210> SEQ ID NO 38
<211> LENGTH: 18
<212> TYPE: DNA
<213> ORGANISM: Artificial Sequence
<220> FEATURE:
<223> OTHER INFORMATION: Synthetic primer

<400> SEQUENCE: 38
atcattacca gcaacagc                                                     18

<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39
caccatggca gatccaaaac aag                                               23

<210> SEQ ID NO 40
<211> LENGTH: 18
<212> TYPE: DNA
<213> ORGANISM: Artificial Sequence
<220> FEATURE:
```

<223> OTHER INFORMATION: Synthetic primer

<400> SEQUENCE: 40
ttgctgagaa ggcaaatc        18

<210> SEQ ID NO 41
<211> LENGTH: 25
<212> TYPE: DNA
<213> ORGANISM: Artificial Sequence
<220> FEATURE:
<223> OTHER INFORMATION: Synthetic primer

<400> SEQUENCE: 41
caccgaaaca ggagaaactg tagaa        25

<210> SEQ ID NO 42
<211> LENGTH: 21
<212> TYPE: DNA
<213> ORGANISM: Artificial Sequence
<220> FEATURE:
<223> OTHER INFORMATION: Synthetic primer

<400> SEQUENCE: 42
taccgcatac aatggatctt c        21

<210> SEQ ID NO 43
<211> LENGTH: 25
<212> TYPE: DNA
<213> ORGANISM: Artificial Sequence
<220> FEATURE:
<223> OTHER INFORMATION: Synthetic primer

<400> SEQUENCE: 43
caccgcagtt attcatgatg aagag        25

<210> SEQ ID NO 44
<211> LENGTH: 24
<212> TYPE: DNA
<213> ORGANISM: Artificial Sequence
<220> FEATURE:
<223> OTHER INFORMATION: Synthetic primer

<400> SEQUENCE: 44
agctaaatgc agtaatgtca ttac        24

<210> SEQ ID NO 45
<211> LENGTH: 28
<212> TYPE: DNA
<213> ORGANISM: Artificial Sequence
<220> FEATURE:
<223> OTHER INFORMATION: Synthetic primer

<400> SEQUENCE: 45
caccgtaatg acattactgc atttagct        28

<210> SEQ ID NO 46
<211> LENGTH: 17
<212> TYPE: DNA
<213> ORGANISM: Artificial Sequence
<220> FEATURE:
<223> OTHER INFORMATION: Synthetic primer

<400> SEQUENCE: 46
caatggggat tgatttc        17

<210> SEQ ID NO 47

```
<211> LENGTH: 25
<212> TYPE: DNA
<213> ORGANISM: Artificial Sequence
<220> FEATURE:
<223> OTHER INFORMATION: Synthetic primer

<400> SEQUENCE: 47
caccgcagtt attcatgatg aagag                                              25

<210> SEQ ID NO 48
<211> LENGTH: 21
<212> TYPE: DNA
<213> ORGANISM: Artificial Sequence
<220> FEATURE:
<223> OTHER INFORMATION: Synthetic primer

<400> SEQUENCE: 48
aatttcttct agatctggct c                                                  21

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
caccgagcca gatctagaag aaatt                                              25

<210> SEQ ID NO 50
<211> LENGTH: 24
<212> TYPE: DNA
<213> ORGANISM: Artificial Sequence
<220> FEATURE:
<223> OTHER INFORMATION: Synthetic primer

<400> SEQUENCE: 50
agctaaatgc agtaatgtca ttac                                               24

<210> SEQ ID NO 51
<211> LENGTH: 22
<212> TYPE: DNA
<213> ORGANISM: Artificial Sequence
<220> FEATURE:
<223> OTHER INFORMATION: Synthetic primer

<400> SEQUENCE: 51
tgttcagtta aaggacgtgt tc                                                 22

<210> SEQ ID NO 52
<211> LENGTH: 21
<212> TYPE: DNA
<213> ORGANISM: Artificial Sequence
<220> FEATURE:
<223> OTHER INFORMATION: Synthetic primer

<400> SEQUENCE: 52
agctaaatgc agcggtgtat c                                                  21

<210> SEQ ID NO 53
<211> LENGTH: 22
<212> TYPE: DNA
<213> ORGANISM: Artificial Sequence
<220> FEATURE:
<223> OTHER INFORMATION: Synthetic primer

<400> SEQUENCE: 53
```
tttgctgaaa agggtgtaaa aa          22

<210> SEQ ID NO 54
<211> LENGTH: 28
<212> TYPE: DNA
<213> ORGANISM: Artificial Sequence
<220> FEATURE:
<223> OTHER INFORMATION: Synthetic primer

<400> SEQUENCE: 54
atcttcagat gtaataggag gtagtccc          28

<210> SEQ ID NO 55
<211> LENGTH: 22
<212> TYPE: DNA
<213> ORGANISM: Artificial Sequence
<220> FEATURE:
<223> OTHER INFORMATION: Synthetic primer

<400> SEQUENCE: 55
tttgctgaaa agggtgtaaa aa          22

<210> SEQ ID NO 56
<211> LENGTH: 21
<212> TYPE: DNA
<213> ORGANISM: Artificial Sequence
<220> FEATURE:
<223> OTHER INFORMATION: Synthetic primer

<400> SEQUENCE: 56
tccatgtaga ccatgaactg c          21

<210> SEQ ID NO 57
<211> LENGTH: 21
<212> TYPE: DNA
<213> ORGANISM: Artificial Sequence
<220> FEATURE:
<223> OTHER INFORMATION: Synthetic primer

<400> SEQUENCE: 57
gcagttcatg gtctacatgg a          21

<210> SEQ ID NO 58
<211> LENGTH: 19
<212> TYPE: DNA
<213> ORGANISM: Artificial Sequence
<220> FEATURE:
<223> OTHER INFORMATION: Synthetic primer

<400> SEQUENCE: 58
tttgctctgg caagaactt          19

<210> SEQ ID NO 59
<211> LENGTH: 21
<212> TYPE: DNA
<213> ORGANISM: Artificial Sequence
<220> FEATURE:
<223> OTHER INFORMATION: Synthetic primer

<400> SEQUENCE: 59
gcagttcatg gtctacatgg a          21

<210> SEQ ID NO 60
<211> LENGTH: 18
<212> TYPE: DNA
<213> ORGANISM: Artificial Sequence
<220> FEATURE:

<223> OTHER INFORMATION: Synthetic primer

<400> SEQUENCE: 60
cgctgatgca cctagaga                                                    18

<210> SEQ ID NO 61
<211> LENGTH: 18
<212> TYPE: DNA
<213> ORGANISM: Artificial Sequence
<220> FEATURE:
<223> OTHER INFORMATION: Synthetic primer

<400> SEQUENCE: 61
tctctaggtg catcagcg                                                    18

<210> SEQ ID NO 62
<211> LENGTH: 19
<212> TYPE: DNA
<213> ORGANISM: Artificial Sequence
<220> FEATURE:
<223> OTHER INFORMATION: Synthetic primer

<400> SEQUENCE: 62
tttgctctgg caagaactt                                                   19

<210> SEQ ID NO 63
<211> LENGTH: 18
<212> TYPE: DNA
<213> ORGANISM: Artificial Sequence
<220> FEATURE:
<223> OTHER INFORMATION: Synthetic primer

<400> SEQUENCE: 63
tctctaggtg catcagcg                                                    18

<210> SEQ ID NO 64
<211> LENGTH: 21
<212> TYPE: DNA
<213> ORGANISM: Artificial Sequence
<220> FEATURE:
<223> OTHER INFORMATION: Synthetic primer

<400> SEQUENCE: 64
acccttatca aatattccac t                                                21

<210> SEQ ID NO 65
<211> LENGTH: 21
<212> TYPE: DNA
<213> ORGANISM: Artificial Sequence
<220> FEATURE:
<223> OTHER INFORMATION: Synthetic primer

<400> SEQUENCE: 65
agtggaatat ttgataaggg t                                                21

<210> SEQ ID NO 66
<211> LENGTH: 19
<212> TYPE: DNA
<213> ORGANISM: Artificial Sequence
<220> FEATURE:
<223> OTHER INFORMATION: Synthetic primer

<400> SEQUENCE: 66
tttgctctgg caagaactt                                                   19

<210> SEQ ID NO 67

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 67
atgcttcatt taacaacaga a                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetic primer

<400> SEQUENCE: 68
atgataacca cgatcaggtt c                                              21

<210> SEQ ID NO 69
<211> LENGTH: 21
<212> TYPE: DNA
<213> ORGANISM: Artificial Sequence
<220> FEATURE:
<223> OTHER INFORMATION: Synthetic primer

<400> SEQUENCE: 69
gaacctgatc gtggttatca t                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetic primer

<400> SEQUENCE: 70
aggatcaact aagaaagaag c                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic primer

<400> SEQUENCE: 71
gcttctttct tagttgatcc t                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic primer

<400> SEQUENCE: 72
atgatcatgt tcattgtgat g                                              21

<210> SEQ ID NO 73
<211> LENGTH: 22
<212> TYPE: DNA
<213> ORGANISM: Artificial Sequence
<220> FEATURE:
<223> OTHER INFORMATION: Synthetic primer

<400> SEQUENCE: 73
```
catcacaatg aacatgatca tg                                              22

<210> SEQ ID NO 74
<211> LENGTH: 21
<212> TYPE: DNA
<213> ORGANISM: Artificial Sequence
<220> FEATURE:
<223> OTHER INFORMATION: Synthetic primer

<400> SEQUENCE: 74
atttccttca agaactggaa c                                               21

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide

<400> SEQUENCE: 75

Glu Gly Asp Ala Val Val Asn Ala Val Ser Gln Glu Thr Pro Ala
1               5                   10                  15

<210> SEQ ID NO 76
<211> LENGTH: 30
<212> TYPE: PRT
<213> ORGANISM: Artificial Sequence
<220> FEATURE:
<223> OTHER INFORMATION: Synthetic peptide

<400> SEQUENCE: 76

Ser Asp Leu His Gly Ser Phe Ser Val Glu Leu Phe Asp Pro Phe Lys
1               5                   10                  15

Glu Ala Val Gln Leu Gly Asn Asp Leu Gln Gln Ser Ser Asp
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: Synthetic peptide

<400> SEQUENCE: 77

Ser Asp Ser His Glu Pro Ser His Leu Glu Leu Pro Ser Leu Ser Glu
1               5                   10                  15

Glu Val Ile Gln Leu Glu Ser Asp Leu Gln Gln Ser Ser Asn
            20                  25                  30

<210> SEQ ID NO 78
<211> LENGTH: 18
<212> TYPE: PRT
<213> ORGANISM: Artificial Sequence
<220> FEATURE:
<223> OTHER INFORMATION: Synthetic peptide

<400> SEQUENCE: 78

Thr Glu Asp Ser Val Ser Ala Pro Ala Thr Glu Asp Ser Val Ser Ala
1               5                   10                  15

Pro Ala

<210> SEQ ID NO 79
<211> LENGTH: 12
<212> TYPE: PRT
<213> ORGANISM: Artificial Sequence
<220> FEATURE:

<223> OTHER INFORMATION: Synthetic peptide

<400> SEQUENCE: 79

Glu Thr Gly Glu Thr Val Glu Glu Gly Leu Tyr Ala
1               5                   10

<210> SEQ ID NO 80
<211> LENGTH: 18
<212> TYPE: PRT
<213> ORGANISM: Artificial Sequence
<220> FEATURE:
<223> OTHER INFORMATION: Synthetic peptide

<400> SEQUENCE: 80

Glu Thr Gly Glu Thr Val Glu Glu Gly Leu Tyr Ala Val Pro Leu Pro
1               5                   10                  15

Lys Asp

<210> SEQ ID NO 81
<211> LENGTH: 28
<212> TYPE: PRT
<213> ORGANISM: Artificial Sequence
<220> FEATURE:
<223> OTHER INFORMATION: Synthetic peptide

<400> SEQUENCE: 81

Glu Thr Gly Glu Thr Val Glu Glu Gly Leu Tyr Ala Val Pro Leu Pro
1               5                   10                  15

Lys Asp Gln Arg Pro Thr Pro Thr Gln Val Leu Glu
            20                  25

<210> SEQ ID NO 82
<211> LENGTH: 20
<212> TYPE: PRT
<213> ORGANISM: Artificial Sequence
<220> FEATURE:
<223> OTHER INFORMATION: Synthetic peptide

<400> SEQUENCE: 82

Glu Pro Asp Leu Glu Glu Ile Val Ser Ile Leu Lys Asn Asp Lys Glu
1               5                   10                  15

Gly Ile Ser Glu
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic peptide

<400> SEQUENCE: 83

Ile Asn Glu Pro Val Gln Val Asp Ile Pro Asn Asn Pro Val Arg Glu
1               5                   10                  15

Gly Arg Asn Val
            20

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide

<400> SEQUENCE: 84

```
Met Thr Leu Leu His Leu Ala
1               5

<210> SEQ ID NO 85
<211> LENGTH: 13
<212> TYPE: PRT
<213> ORGANISM: Artificial Sequence
<220> FEATURE:
<223> OTHER INFORMATION: Synthetic peptide

<400> SEQUENCE: 85

Gln Gly Ala Asp Val Lys Lys Ser Ser Cys Gln Ser Lys
1               5                   10

<210> SEQ ID NO 86
<211> LENGTH: 21
<212> TYPE: PRT
<213> ORGANISM: Artificial Sequence
<220> FEATURE:
<223> OTHER INFORMATION: Synthetic peptide

<400> SEQUENCE: 86

Gln Ala Val Ser Pro Ser Thr Ser Gln Gly Ala Asp Val Lys Lys Ser
1               5                   10                  15

Ser Cys Gln Ser Lys
            20

<210> SEQ ID NO 87
<211> LENGTH: 5
<212> TYPE: PRT
<213> ORGANISM: Artificial Sequence
<220> FEATURE:
<223> OTHER INFORMATION: Synthetic peptide

<400> SEQUENCE: 87

Ser Cys Gln Ser Lys
1               5

<210> SEQ ID NO 88
<211> LENGTH: 34
<212> TYPE: PRT
<213> ORGANISM: Artificial Sequence
<220> FEATURE:
<223> OTHER INFORMATION: Synthetic peptide

<400> SEQUENCE: 88

Ser Ser Ser Glu Pro Phe Val Ala Glu Ser Glu Val Ser Lys Val Glu
1               5                   10                  15

Gln Glu Glu Thr Asn Pro Glu Val Leu Ile Lys Asp Leu Gln Asp Val
            20                  25                  30

Ala Ser

<210> SEQ ID NO 89
<211> LENGTH: 31
<212> TYPE: PRT
<213> ORGANISM: Artificial Sequence
<220> FEATURE:
<223> OTHER INFORMATION: Synthetic peptide

<400> SEQUENCE: 89

Ser Ser Ser Glu Val Gly Glu Lys Val Ser Glu Thr Ser Lys Glu Glu
1               5                   10                  15

Ser Thr Pro Glu Val Lys Ala Glu Asp Leu Gln Pro Ala Val Asp
            20                  25                  30
```

```
<210> SEQ ID NO 90
<211> LENGTH: 32
<212> TYPE: PRT
<213> ORGANISM: Artificial Sequence
<220> FEATURE:
<223> OTHER INFORMATION: Synthetic peptide

<400> SEQUENCE: 90

Met Asp Ile Asp Asn Ser Asn Ile Ser Thr Ala Asp Ile Arg Ser Asn
1               5                   10                  15

Thr Asp Gly Leu Ile Asp Ile Ile Met Arg Ile Leu Gly Phe Gly Asn
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Synthetic peptide

<400> SEQUENCE: 91

Met Asp Ile Asp Asn Asn Asn Val Thr Thr Ser Ser Thr Gln Asp Lys
1               5                   10                  15

Ser Gly Asn Leu Met Glu Val Ile Met Arg Ile Leu Asn Phe Gly Asn
            20                  25                  30

<210> SEQ ID NO 92
<211> LENGTH: 48
<212> TYPE: PRT
<213> ORGANISM: Artificial Sequence
<220> FEATURE:
<223> OTHER INFORMATION: Synthetic peptide

<400> SEQUENCE: 92

Gly Gln Tyr Val Cys Gly Tyr Glu Met Tyr Met Tyr Gly Phe Gln Asp
1               5                   10                  15

Val Lys Asp Leu Leu Gly Gly Leu Leu Ser Asn Val Pro Val Cys Cys
            20                  25                  30

Asn Val Ser Leu Tyr Phe Met Glu His Asn Tyr Phe Thr Asn His Glu
        35                  40                  45

<210> SEQ ID NO 93
<211> LENGTH: 48
<212> TYPE: PRT
<213> ORGANISM: Artificial Sequence
<220> FEATURE:
<223> OTHER INFORMATION: Synthetic peptide

<400> SEQUENCE: 93

Gly Glu His Val His Met Tyr Gly Ile Tyr Val Tyr Arg Val Gln Ser
1               5                   10                  15

Val Lys Asp Leu Ser Gly Val Phe Asn Ile Asp His Ser Thr Cys Asp
            20                  25                  30

Cys Asn Leu Asp Val Tyr Phe Gly Tyr Asn Ser Phe Thr Asn Lys Glu
        35                  40                  45

<210> SEQ ID NO 94
<211> LENGTH: 80
<212> TYPE: PRT
<213> ORGANISM: Artificial Sequence
<220> FEATURE:
<223> OTHER INFORMATION: Synthetic peptide

<400> SEQUENCE: 94

Ser Ser Ser Glu Pro Phe Val Ala Glu Ser Glu Val Ser Lys Val Glu
```

```
                1               5                  10                   15
Gln Glu Glu Thr Asn Pro Glu Val Leu Ile Lys Asp Leu Gln Asp Val
            20                  25                  30

Ala Ser His Glu Ser Gly Val Ser Asp Gln Pro Ala Gln Val Val Thr
        35                  40                  45

Glu Arg Glu Ser Glu Ile Gly Ser His Gln Gly Thr Glu Lys Glu
    50                  55                  60

Ser Gly Ile Thr Glu Ser His Gln Lys Glu Asp Glu Ile Val Ser Gln
65                  70                  75                  80

<210> SEQ ID NO 95
<211> LENGTH: 22
<212> TYPE: PRT
<213> ORGANISM: Artificial Sequence
<220> FEATURE:
<223> OTHER INFORMATION: Synthetic peptide

<400> SEQUENCE: 95

Ser Ser Ser Glu Pro Phe Val Ala Glu Ser Glu Val Ser Lys Val Glu
1               5                   10                  15

Gln Glu Glu Thr Asn Pro
            20

<210> SEQ ID NO 96
<211> LENGTH: 16
<212> TYPE: PRT
<213> ORGANISM: Artificial Sequence
<220> FEATURE:
<223> OTHER INFORMATION: Synthetic peptide

<400> SEQUENCE: 96

Glu Thr Asn Pro Glu Val Leu Ile Lys Asp Leu Gln Asp Val Ala Ser
1               5                   10                  15

<210> SEQ ID NO 97
<211> LENGTH: 23
<212> TYPE: PRT
<213> ORGANISM: Artificial Sequence
<220> FEATURE:
<223> OTHER INFORMATION: Synthetic peptide

<400> SEQUENCE: 97

Asp Leu Gln Asp Val Ala Ser His Glu Ser Gly Val Ser Asp Gln Pro
1               5                   10                  15

Ala Gln Val Val Thr Glu Arg
            20

<210> SEQ ID NO 98
<211> LENGTH: 22
<212> TYPE: PRT
<213> ORGANISM: Artificial Sequence
<220> FEATURE:
<223> OTHER INFORMATION: Synthetic peptide

<400> SEQUENCE: 98

Gln Val Val Thr Glu Arg Glu Ser Glu Ile Gly Ser His Gln Gly Glu
1               5                   10                  15

Thr Glu Lys Glu Ser Gly
            20

<210> SEQ ID NO 99
<211> LENGTH: 21
<212> TYPE: PRT
<213> ORGANISM: Artificial Sequence
```

```
<220> FEATURE:
<223> OTHER INFORMATION: Synthetic peptide

<400> SEQUENCE: 99

Glu Thr Glu Lys Glu Ser Gly Ile Thr Glu Ser His Gln Lys Glu Asp
1               5                   10                  15

Glu Ile Val Ser Gln
            20

<210> SEQ ID NO 100
<211> LENGTH: 36
<212> TYPE: PRT
<213> ORGANISM: Artificial Sequence
<220> FEATURE:
<223> OTHER INFORMATION: Synthetic peptide

<400> SEQUENCE: 100

Ser Ser Ser Glu Val Gly Glu Lys Val Ser Glu Thr Ser Lys Glu Glu
1               5                   10                  15

Ser Thr Pro Glu Val Lys Ala Glu Asp Leu Gln Pro Ala Val Asp Gly
            20                  25                  30

Ser Val Glu His
        35

<210> SEQ ID NO 101
<211> LENGTH: 11
<212> TYPE: PRT
<213> ORGANISM: Artificial Sequence
<220> FEATURE:
<223> OTHER INFORMATION: Synthetic peptide

<400> SEQUENCE: 101

Ser Lys Glu Glu Asn Thr Pro Glu Val Lys Ala
1               5                   10

<210> SEQ ID NO 102
<211> LENGTH: 63
<212> TYPE: PRT
<213> ORGANISM: Artificial Sequence
<220> FEATURE:
<223> OTHER INFORMATION: Synthetic peptide

<400> SEQUENCE: 102

Glu Thr Gly Glu Thr Val Glu Glu Gly Leu Tyr Ala Val Pro Leu Pro
1               5                   10                  15

Lys Asp Gln Arg Pro Thr Pro Thr Gln Val Leu Glu Gly Asp Pro Ser
            20                  25                  30

Val Glu Glu Glu Glu Ile Ala Pro Pro Leu Pro Pro Arg Gly Asp Val
        35                  40                  45

Ala Glu Leu Gln Glu Ala Val Glu Glu Asp Pro Leu Tyr Ala Val
    50                  55                  60

<210> SEQ ID NO 103
<211> LENGTH: 16
<212> TYPE: PRT
<213> ORGANISM: Artificial Sequence
<220> FEATURE:
<223> OTHER INFORMATION: Synthetic peptide

<400> SEQUENCE: 103

Val Pro Leu Pro Lys Asp Gln Arg Pro Thr Pro Thr Gln Val Leu Glu
1               5                   10                  15

<210> SEQ ID NO 104
```

```
<211> LENGTH: 19
<212> TYPE: PRT
<213> ORGANISM: Artificial Sequence
<220> FEATURE:
<223> OTHER INFORMATION: Synthetic peptide

<400> SEQUENCE: 104

Gln Arg Pro Thr Pro Thr Gln Val Leu Glu Glu Asp Pro Ser Val Glu
1               5                   10                  15

Glu Glu Glu

<210> SEQ ID NO 105
<211> LENGTH: 16
<212> TYPE: PRT
<213> ORGANISM: Artificial Sequence
<220> FEATURE:
<223> OTHER INFORMATION: Synthetic peptide

<400> SEQUENCE: 105

Glu Asp Pro Ser Val Glu Glu Glu Ile Ala Pro Pro Leu Pro Pro
1               5                   10                  15

<210> SEQ ID NO 106
<211> LENGTH: 26
<212> TYPE: PRT
<213> ORGANISM: Artificial Sequence
<220> FEATURE:
<223> OTHER INFORMATION: Synthetic peptide

<400> SEQUENCE: 106

Ile Ala Pro Pro Leu Pro Pro Arg Gly Asp Val Ala Glu Leu Gln Glu
1               5                   10                  15

Ala Val Glu Glu Asp Pro Leu Tyr Ala Val
            20                  25

<210> SEQ ID NO 107
<211> LENGTH: 48
<212> TYPE: PRT
<213> ORGANISM: Artificial Sequence
<220> FEATURE:
<223> OTHER INFORMATION: Synthetic peptide

<400> SEQUENCE: 107

Glu Pro Asp Leu Glu Glu Ile Val Ser Ile Leu Lys Asn Asp Lys Glu
1               5                   10                  15

Gly Ile Ser Glu Leu Ile Asn Glu Pro Val Gln Val Asp Ile Pro Asn
            20                  25                  30

Asn Pro Val Arg Glu Gly Arg Asn Val Met Thr Leu Leu His Leu Ala
        35                  40                  45

<210> SEQ ID NO 108
<211> LENGTH: 20
<212> TYPE: PRT
<213> ORGANISM: Artificial Sequence
<220> FEATURE:
<223> OTHER INFORMATION: Synthetic peptide

<400> SEQUENCE: 108

Ser Ile Leu Lys Asn Asp Lys Glu Gly Ile Ser Glu Leu Ile Asn Glu
1               5                   10                  15

Pro Val Gln Val
            20

<210> SEQ ID NO 109
<211> LENGTH: 20
```

```
<212> TYPE: PRT
<213> ORGANISM: Artificial Sequence
<220> FEATURE:
<223> OTHER INFORMATION: Synthetic peptide

<400> SEQUENCE: 109

Ile Asn Glu Pro Val Gln Val Asp Ile Pro Asn Asn Pro Val Arg Glu
1               5                   10                  15

Gly Arg Asn Val
            20

<210> SEQ ID NO 110
<211> LENGTH: 25
<212> TYPE: PRT
<213> ORGANISM: Artificial Sequence
<220> FEATURE:
<223> OTHER INFORMATION: Synthetic peptide

<400> SEQUENCE: 110

Glu Pro Val Gln Val Asp Ile Pro Asn Asn Pro Val Arg Glu Gly Arg
1               5                   10                  15

Asn Val Met Thr Leu Leu His Leu Ala
            20                  25

<210> SEQ ID NO 111
<211> LENGTH: 63
<212> TYPE: PRT
<213> ORGANISM: Artificial Sequence
<220> FEATURE:
<223> OTHER INFORMATION: Synthetic peptide

<400> SEQUENCE: 111

Ser Gly Ile Phe Asp Lys Gly Glu Gly Gln His Lys Ala Ser Glu Glu
1               5                   10                  15

Gln Leu Gln Glu Leu Ser Glu Glu Ile Thr Asp Ile Val Gln Gly Leu
            20                  25                  30

Pro Pro Ile Thr Ser Glu Asp Ile Gly Ala Gln Ala Val Ser Pro Ser
        35                  40                  45

Thr Ser Gln Gly Ala Asp Val Lys Lys Ser Ser Cys Gln Ser Lys
    50                  55                  60

<210> SEQ ID NO 112
<211> LENGTH: 25
<212> TYPE: PRT
<213> ORGANISM: Artificial Sequence
<220> FEATURE:
<223> OTHER INFORMATION: Synthetic peptide

<400> SEQUENCE: 112

Ser Gly Ile Phe Asp Lys Gly Glu Gly Gln His Lys Ala Ser Glu Glu
1               5                   10                  15

Gln Leu Gln Glu Leu Ser Glu Glu Ile
            20                  25

<210> SEQ ID NO 113
<211> LENGTH: 26
<212> TYPE: PRT
<213> ORGANISM: Artificial Sequence
<220> FEATURE:
<223> OTHER INFORMATION: Synthetic peptide

<400> SEQUENCE: 113

Ser Glu Glu Gln Leu Gln Glu Leu Ser Glu Glu Ile Thr Asp Ile Val
1               5                   10                  15
```

```
Gln Gly Leu Pro Pro Ile Thr Ser Glu Asp
            20                  25

<210> SEQ ID NO 114
<211> LENGTH: 25
<212> TYPE: PRT
<213> ORGANISM: Artificial Sequence
<220> FEATURE:
<223> OTHER INFORMATION: Synthetic peptide

<400> SEQUENCE: 114

Thr Asp Ile Val Gln Gly Leu Pro Pro Ile Thr Ser Glu Asp Ile Gly
1               5                   10                  15

Ala Gln Ala Val Ser Pro Ser Thr Ser
            20                  25

<210> SEQ ID NO 115
<211> LENGTH: 25
<212> TYPE: PRT
<213> ORGANISM: Artificial Sequence
<220> FEATURE:
<223> OTHER INFORMATION: Synthetic peptide

<400> SEQUENCE: 115

Asp Ile Gly Ala Gln Ala Val Ser Pro Ser Thr Ser Gln Gly Ala Asp
1               5                   10                  15

Val Lys Lys Ser Ser Cys Gln Ser Lys
            20                  25

<210> SEQ ID NO 116
<211> LENGTH: 20
<212> TYPE: PRT
<213> ORGANISM: Artificial Sequence
<220> FEATURE:
<223> OTHER INFORMATION: Synthetic peptide

<400> SEQUENCE: 116

Asp Ile Gly Ala Gln Ala Val Ser Pro Ser Thr Ser Gln Gly Ala Asp
1               5                   10                  15

Val Lys Lys Ser
            20

<210> SEQ ID NO 117
<211> LENGTH: 21
<212> TYPE: PRT
<213> ORGANISM: Artificial Sequence
<220> FEATURE:
<223> OTHER INFORMATION: Synthetic peptide

<400> SEQUENCE: 117

Gln Ala Val Ser Pro Ser Thr Ser Gln Gly Ala Asp Val Lys Lys Ser
1               5                   10                  15

Ser Cys Gln Ser Lys
            20

<210> SEQ ID NO 118
<211> LENGTH: 44
<212> TYPE: PRT
<213> ORGANISM: Artificial Sequence
<220> FEATURE:
<223> OTHER INFORMATION: Synthetic peptide

<400> SEQUENCE: 118

His His Asn Glu His Asp His Asp Ala His Gly Arg Gly Ala Ala Ser
1               5                   10                  15
```

-continued

```
Ser Val Ala Glu Gly Val Gly Ser Ala Ile Ser Gln Ile Leu Ser Leu
            20                  25                  30

Ser Asp Ser Ile Val Val Pro Val Leu Glu Gly Asn
            35                  40
```

<210> SEQ ID NO 119
<211> LENGTH: 22
<212> TYPE: PRT
<213> ORGANISM: Artificial Sequence
<220> FEATURE:
<223> OTHER INFORMATION: Synthetic peptide

<400> SEQUENCE: 119

```
His His Asn Glu His Asp His Asp Ala His Gly Arg Gly Ala Ala Ser
1               5                   10                  15

Ser Val Ala Glu Gly Val
            20
```

<210> SEQ ID NO 120
<211> LENGTH: 22
<212> TYPE: PRT
<213> ORGANISM: Artificial Sequence
<220> FEATURE:
<223> OTHER INFORMATION: Synthetic peptide

<400> SEQUENCE: 120

```
Arg Gly Ala Ala Ser Ser Val Ala Glu Gly Val Gly Ser Ala Ile Ser
1               5                   10                  15

Gln Ile Leu Ser Leu Ser
            20
```

<210> SEQ ID NO 121
<211> LENGTH: 22
<212> TYPE: PRT
<213> ORGANISM: Artificial Sequence
<220> FEATURE:
<223> OTHER INFORMATION: Synthetic peptide

<400> SEQUENCE: 121

```
Gly Ser Ala Ile Ser Gln Ile Leu Ser Leu Ser Asp Ser Ile Val Val
1               5                   10                  15

Pro Val Leu Glu Gly Asn
            20
```

<210> SEQ ID NO 122
<211> LENGTH: 19
<212> TYPE: PRT
<213> ORGANISM: Artificial Sequence
<220> FEATURE:
<223> OTHER INFORMATION: Synthetic peptide

<400> SEQUENCE: 122

```
Ala Ser Val Ser Glu Gly Asp Ala Val Val Asn Ala Val Ser Gln Glu
1               5                   10                  15

Thr Pro Ala
```

<210> SEQ ID NO 123
<211> LENGTH: 26
<212> TYPE: PRT
<213> ORGANISM: Artificial Sequence
<220> FEATURE:
<223> OTHER INFORMATION: Synthetic peptide

<400> SEQUENCE: 123

```
Thr Gln Pro Gln Ser Arg Asp Ser Leu Leu Asn Glu Glu Asp Met Ala
```

-continued

```
1               5                   10                  15
Ala Gln Phe Gly Asn Arg Tyr Phe Tyr Phe
            20                  25
```

IMMUNOREACTIVE *EHRLICHIA* P120/P140 EPITOPES AND USES THEREOF

This application claims priority to U.S. Application No. 61/173,345 filed on Apr. 28, 2009, the entire disclosure of which is specifically incorporated herein by reference in its entirety without disclaimer.

This invention was made with U.S. government support under grant R01 AI 071145 from the National Institutes of Health. The government has certain rights in the invention.

BACKGROUND OF THE INVENTION

I. Field of the Invention

The present invention relates generally to the diagnosis and treatment of *Ehrlichia* infection. In particular, the invention is related to p120/p140 immunoreactive peptides derived from *Ehrlichia* proteins, and the use of such peptides in the detection of *Ehrlichia* infection in humans and animals.

II. Background and Description of Related Art

*Ehrlichia chaffeensis* and *Ehrlichia canis* are tick-transmitted, obligately intracellular bacterium that cause monocytotropic ehrlichiosis, an emerging life-threatening disease in humans and a mild to severe disease in wild and domestic canids. A number of studies have demonstrated that antibodies play an essential role in immunity against Ehrlichial pathogens (Feng and Walker, 2004; Winslow et al., 2003; Winslow et al., 2000; Yager et al., 2005). However, only a small subset of *E. chaffeensis* and *E. canis* proteins react strongly with antibodies in sera from infected humans or dogs, and thus are considered to be major immunoreactive proteins (Chen et al., 1997; Chen et al., 1994; McBride et al., 2003; Rikihisa et al., 1994). Molecularly characterized major immunoreactive proteins of *E. chaffeensis* and *E. canis* include four protein ortholog pairs (p200/p200, p120/p140, p47/p36, and VLPT/p19, respectively) (Doyle et al., 2006; Luo et al., 2008; McBride et al., 2003; McBride et al., 2007; McBride et al., 2000; Nethery et al., 2007). Three of these ortholog pairs (p120/p140, p47/p36, and VLPT/p19) have acidic serine-rich tandem repeats (TRs), and continuous species-specific epitopes have been identified in the TRs of p47/p36 and VLPT/p19 (Doyle et al., 2006; Luo et al., 2008; McBride et al., 2007; McBride et al., 2000).

The p120 is differentially expressed by dense-cored *E. chaffeensis*, and is found on the surface of the organism and free in the morula space; however, the role of this protein in pathobiology or in eliciting a protective immune response is unknown (Popov et al., 2000). *E. chaffeensis* p120 has two to five nearly identical serine-rich 80-amino acid TRs, and similarly orthologous *E. canis* p140 contains 12 or 14 nearly identical serine-rich 36-amino acid TRs (Yabsley et al., 2003; Yu et al., 1997; Yu et al., 2000; Zhang et al., 2008). Specific regions of the p120 and p140 proteins are immunoreactive (McBride et al., 2000; Yu et al., 1996; Yu et al., 2000); however, it is presently unclear as to which sequences within the immunoreactive regions may be recognized by a host immune system.

Current methodologies for diagnosing human monocytotropic ehrlichiosis (HME) present significant clinical limitations. Clinical diagnosis of HME is usually confirmed retrospectively by detection of *Ehrlichia*-specific antibodies in patient sera using an indirect fluorescent-antibody assay (IFA) (Dumler et al., 2007). The limitations of IFA include lack of standardization between laboratories, false positive interpretations due to autoantibodies or antibodies directed at conserved bacterial proteins, and cross-reactive antibodies produced by related organisms (for example, *E. canis*, *E. ewingii*, and *Anaplasma phagocytophilum*) that can make identification of the specific etiologic agent difficult (Carpenter et al., 1999; Chen et al., 1994; Comer et al., 1999; Paddock and Childs, 2003; Unver et al., 2001). Furthermore, IFA requires expensive microscopy equipment and highly skilled technicians to produce the antigen and interpret results. Molecular diagnostic methods such as PCR are useful for specific and sensitive detection of *E. chaffeensis* prior to development of reactive antibodies (Childs et al., 1999), but PCR is not useful after antibiotic therapy is initiated, and the clinical sensitivity of PCR in the primary care setting has not been unequivocally determined. Therefore, PCR is currently considered only a valuable adjunct to IFA for diagnosis (Walker et al., 2000). HME diagnosis thus presents significant clinical limitations, and Ehrlichiosis continues to be an emerging infectious disease. Clearly, there is a need for new and improved methods for the detection and diagnosis of Ehrlichiosis.

SUMMARY OF THE INVENTION

The present invention overcomes limitations in the prior art by providing compositions and methods for the diagnosis or detection of *Ehrlichia* infection. The present invention provides, in certain embodiments, p120/p140 immunoreactive peptides derived from *Ehrlichia* proteins which may be used to identify *Ehrlichia*-specific antibodies in a sample, diagnose an *Ehrlichia* infection in a subject, distinguish between infected and immunized subjects, and/or determine whether the *Ehrlichia* infection in a subject is caused by *Ehrlichia chaffeensis* or *Ehrlichia canis*. These immunoreactive peptides may also be included in a vaccine composition or used to induce a protective immune response in a subject against an *Ehrlichia* infection. The p120/p140 immunoreactive peptides may selectively bind an *Ehrlichia*-specific antibody, such as antibodies specific for the 120 kD protein of an *Ehrlichia chaffeensis* or the 140 kD protein of an *Ehrlichia canis*. One or more of the p120/p140 immunoreactive peptides may be included or used in a diagnostic kit or assay such as, e.g., an enzyme-linked immunosorbent assay (ELISA), a solid phase assay, and/or a lateral flow assay.

Certain aspects of the present invention are based, in part, on the discovery that certain p120 immunoreactive peptides, such as the synthetic TRP120-R-I1 peptide, described herein below, can surprisingly exhibit substantially improved and increased sensitivity for diagnosing ehrlichiosis in humans as compared to other immunoreactive *Ehrlichia* peptides or even a recombinant *Ehrlichia* p120 protein. For example, as shown in the below examples, TRP120-R-I1 peptide exhibited a 96.7% specificity for diagnosing HME, whereas p32 immunoreactive peptides, p47 immunoreactive peptides, Ank200 immunoreactive peptides, and recombinant p120 only displayed specificities of 87.1%, 77.4%, 61.3%, and 90.3%, respectively. Further, various p120/p140 immunoreactive peptides of the present invention may be synthesized, e.g., using solid-phase synthesis; without wishing to be bound by any theory, synthetic p120/p140 immunoreactive peptides may provide the advantage of efficient generation in consistently highly pure forms without contaminating *E. coli* proteins that can result in false positive reactions when utilizing recombinant proteins. The data presented in the below Examples demonstrates that a single synthetic peptide from TRP120 can provide highly sensitive and specific diagnosis of HME infection comparable to the "gold standard" IFA and may be used for standardized specific point-of-care and/or reference laboratory immunodiagnostics for HME.

An aspect of the present invention relates to an isolated peptide 45 amino acids in length or less and comprising the sequence of SEQ ID NO:1, 2, 4, 5, 6, 7, 8, 9 or 10, or a sequence having at least 90% identity to SEQ ID NO:1, 2, 4, 5, 6, 7, 8, 9 or 10, wherein the peptide selectively binds an antibody that recognizes and binds an *Ehrlichia* p120 or p140 protein. In certain embodiments, peptide is from 20 to 30 amino acids in length. The peptide may comprise SEQ ID NO:1 or SEQ ID NO:2. In various embodiments, the peptide consists of SEQ ID NO:1 or SEQ ID NO:2. In certain embodiments, the peptide has at least 95% identity to SEQ ID NO:1, 2, 4, 5, 6, 7, 8, 9 or 10. The peptide may comprise, in certain embodiments, SEQ ID NO: 4, 5, 6, 7, 8, 9, or 10. In various embodiments, the isolated peptide is immobilized on a surface of a support substrate. The support substrate may comprise latex, polystyrene, nylon, nitrocellulose, cellulose, silica, agarose, or magnetic resin. In certain embodiments, the support substrate is a reaction chamber, a well, a membrane, a filter, a paper, an emulsion, a bead, a microbead, a dipstick, a card, a glass slide, a lateral flow apparatus, a microchip, a comb, a silica particle, a magnetic particle, a nanoparticle, or a self-assembling monolayer. The peptide may be comprised in a kit. The peptide may be comprised in a pharmaceutical preparation. In certain embodiments, the peptide is produced via peptide synthesis. In other embodiments, the peptide may be recombinantly produced. The isolated peptide may further comprises a detectable label.

Another aspect of the present invention relates to a method of detecting antibodies that specifically bind an *Ehrlichia* organism in a test sample, comprising: (a) contacting an isolated p120/p140 immunoreactive peptide (e.g., a peptide 45 amino acids or less in length and comprising the sequence of SEQ ID NO:1, 2, 4, 5, 6, 7, 8, 9 or 10, or a sequence having at least 90% identity to SEQ ID NO:1, 2, 4, 5, 6, 7, 8, 9 or 10, wherein the peptide selectively binds an antibody that recognizes and binds an *Ehrlichia* p120 or p140 protein), with the test sample, under conditions that allow peptide-antibody complexes to form; (b) detecting the peptide-antibody complexes; wherein the detection of the peptide-antibody complexes is an indication that antibodies specific for an *Ehrlichia* organism are present in the test sample, and wherein the absence of the peptide-antibody complexes is an indication that antibodies specific an *Ehrlichia* organism are not present in the test sample. The *Ehrlichia* organism may be an *Ehrlichia chaffeensis* or an *Ehrlichia canis* organism. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a Bio-Plex® suspension array assay, a mass spectrometry assay, or a particulate-based assay. The step of detecting may comprise a lateral flow assay or a an enzyme-linked immunoassay, wherein the enzyme-linked immunoassay is an ELISA.

Yet another aspect of the present invention relates to a method of identifying an *Ehrlichia* infection in a subject comprising: (a) contacting a sample from the subject with an isolated p120/p140 immunoreactive peptide (e.g., a peptide of 45 amino acids or less in length and comprising the sequence of SEQ ID NO:1, 2, 4, 5, 6, 7, 8, 9 or 10, or a sequence having at least 90% identity to SEQ ID NO:1, 2, 4, 5, 6, 7, 8, 9 or 10, wherein the peptide selectively binds an antibody that recognizes and binds an *Ehrlichia* p120 or p140 protein) under conditions that allow peptide-antibody complexes to form; and (b) detecting the peptide-antibody complexes; wherein the detection of the peptide-antibody complexes is an indication that the subject has an *Ehrlichia* infection. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a Bio-Plex suspension array assay, a dipstick test, or a particulate-based assay. In certain embodiments, the subject is a dog or a human. The method may be at least about 90.3%, 91%, 92%, 93%, 94%, 95%, 96%, or about 96.8% sensitive.

Another aspect of the present invention relates to a method of distinguishing between an active *Ehrlichia* infection and a previous *Ehrlichia* immunization in a subject, the method comprising: (a) contacting a sample from the subject with at least one isolated p120/p140 immunoreactive peptide that is not a component of an *Ehrlichia* vaccine; and (b) detecting whether an antibody in the sample specifically binds to the isolated peptide; wherein if an antibody in the sample specifically binds to the isolated peptide, then the subject has an active *Ehrlichia* infection, and if an antibody does not specifically bind to the isolated peptide, then the subject is either previously immunized with an *Ehrlichia* vaccine or is not infected with an *Ehrlichia* organism. The subject may be a dog or a human. The *Ehrlichia* organism may be an *Ehrlichia chaffeensis* or an *Ehrlichia canis* organism.

Yet another aspect of the present invention relates to a method of distinguishing between an *Ehrlichia chaffeensis* infection and an *Ehrlichia canis* infection in a subject, the method comprising: (a) contacting a first sample from the subject with an isolated peptide comprising an amino acid sequence having about 95% or more sequence identity with a peptide selected from the group consisting of SEQ ID NOs 1, 4, 5, and 6; (b) contacting a second sample from the subject with an isolated peptide comprising an amino acid sequence having about 95% or more sequence identity with a peptide selected from the group consisting of SEQ ID NOs: 2, 7, 8, 9, and 10; (c) detecting the presence of peptide-antibody complexes in each of the first and second samples; wherein the presence of peptide-antibody complexes in the first sample is an indication that the subject has an *Ehrlichia chaffeensis* infection, and wherein the presence of peptide-antibody complexes in the second sample is an indication that the subject has an *Ehrlichia canis* infection. The subject may be a dog.

Another aspect of the present invention relates to an isolated amino acid sequence having about 90% or more sequence identity with SEQ ID NOs 1, 2, 3, 4, 5, 6, 7, 8, 9, or 10; wherein the peptide is from 15 to 40 amino acids in length, and wherein the peptide can selectively bind an *Ehrlichia*-specific antibody. In certain embodiments, the isolated amino acid has about 95% or more or more sequence identity with SEQ ID NOs 1, 2, 3, 4, 5, 6, 7, 8, 9, or 10.

Yet another aspect of the present invention relates to an isolated nucleic acid segment encoding an isolated peptide, wherein the peptide is 45 amino acids or less in length and comprises the sequence of SEQ ID NO:1, 2, 4, 5, 6, 7, 8, 9 or 10, or a sequence having at least 90% identity to SEQ ID NO:1, 2, 4, 5, 6, 7, 8, 9 or 10, wherein the peptide selectively binds an antibody that recognizes and binds an *Ehrlichia* p120 or p140 protein. The isolated nucleic acid may, in various embodiments, encode an amino acid sequence having about 90% or more, or about 95% or more sequence identity with SEQ ID NOs 1, 2, 4, 5, 6, 7, 8, 9, or 10; wherein the peptide is from 15 to 40 amino acids in length, and wherein the peptide can selectively bind an *Ehrlichia*-specific antibody.

Another aspect of the present invention relates to a vector comprising a contiguous sequence consisting of the nucleic acid segment.

Yet another aspect of the present invention relates to a host cell comprising the nucleic acid segment.

Another aspect of the present invention relates to a kit comprising: (a) an isolated p120/p140 immunoreactive peptide (e.g., a peptide 45 amino acids or less in length and comprising the sequence of SEQ ID NO:1, 2, 4, 5, 6, 7, 8, 9 or 10, or a sequence having at least 90% identity to SEQ ID NO:1, 2, 4, 5, 6, 7, 8, 9 or 10, wherein the peptide selectively binds an antibody that recognizes and binds an *Ehrlichia* p120 or p140 protein), (b) an anti-dog or anti-human secondary antibody linked to a reporter molecule; and, (c) an appropriate reagent for detection of the reporter molecule. The peptide may be immobilized on a membrane or a microtiter plate. The reporter molecule may be selected from the group consisting of luciferase, horseradish peroxidase, P-galactosidase, and a fluorescent label. The kit may further comprises a dilution buffer for dog or human serum. The kit may comprise a lateral flow immunoassay, a lateral flow immunochromatographic assay, or an enzyme-linked immunosorbent assay (ELISA).

In various embodiments, antibody epitopes of *Ehrlichia chaffeensis* Ankrin protein 200 and Tandem repeat protein 47 are also provided (e.g., as shown in FIG. 10 and FIG. 12A). These peptides may be used for the diagnosis of *Ehrlichia* infection. In various embodiments, one or more of these peptides may be included in a vaccine composition or used for vaccination purposes or to induce an immune response against *Ehrlichia chaffeensis* or *Ehrlichia canis*.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It is contemplated that any embodiment discussed in this specification can be implemented with respect to any method or composition of the invention, and vice versa. Furthermore, compositions of the invention can be used to achieve methods of the invention.

Other objects, features and/or advantages of the present invention will become apparent from the following detailed description. It should be understood that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Schematic of *E. chaffeensis* p120 and *E. canis* p140 proteins showing domains, location of TRs (number of amino acids in parentheses; R=repeat), and recombinant proteins used for epitope mapping. For both p120 and p140, there were two incomplete repeats preceding the first repeat and following the last repeat, respectively, which were homologous to tandem repeats and also shown in gray. The N-terminus (N); C-terminus (C); tandem repeat region (TR); whole protein (W). (FIG. 1B) Schematic of synthetic peptides used to map the tandem repeat epitope of *E. chaffeensis* p120 and *E. canis* p140 proteins.

FIG. 2. Alignments of amino acid sequence of homologous regions in tandem repeat unit, N- and C-terminal regions of *E. chaffeensis* p120 and *E. canis* p140 proteins. Residues that match the consensus within two distance units are boxed, and gaps are shown by dashes. The major TR epitope of *E. chaffeensis* p120 (22-mer) and *E. canis* p140 (19-mer) are identified with a bar.

(FIG. 3A) *E. chaffeensis* whole-cell lysates (lane 1), supernatants derived from *E. chaffeensis*-infected cells (lane 2), and *E. canis* whole-cell lysates (lane 3) reacted with rabbit anti-p120R-I1 antibody. (FIG. 3B) *E. canis* whole-cell lysates (lane 1), supernatants derived from *E. canis*-infected cells (lane 2), and *E. chaffeensis* whole-cell lysates (lane 3) reacted with rabbit anti-p140 peptide antibody. Pre-immunization rabbit serum controls did not recognize *Ehrlichia* whole-cell lysates. Precision Protein Standard (Bio-Rad).

(FIG. 4A) SDS-PAGE and total protein staining of purified recombinant p120 recombinant fragments (whole protein [W], N-terminus [N], tandem repeats [TR, two repeats], and C-terminus [C]) (left), and corresponding Western immunoblot probed with two anti-*E. chaffeensis* dog (experimentally infected; 2251 and 2495 [D-2251/Ech and D-2495/Ech]) sera and two HME patient (SC07 and CDC4 [H-SC07/Ech and H-CDC4/Ech]) sera (right). (FIG. 4B) SDS-PAGE and total protein staining of purified recombinant p140 proteins fragments (whole protein [W], N-terminus [N], tandem repeats [TR, fourteen repeats], and C-terminus [C]) (left), and corresponding Western immunoblot probed with three anti-*E. canis* sera from one experimentally infected dog (2995 [D-2995/Eca]) and two naturally infected dogs (4283 and 2160 [D-4283/Eca and D-2160/Eca]) (right). Human or dog sera did not recognize thioredoxin or GST proteins, and the normal human or dog sera did not recognize these recombinant proteins by Western immunoblot. M, Precision Protein Standard (Bio-Rad).

(FIG. 5A) Sequence and orientation of all overlapping peptides representing *E. chaffeensis* p120 repeat unit. (FIG. 5B) *E. chaffeensis* p120 peptides reacted with the anti-*E. chaffeensis* dog serum derived from an experimentally infected dog (2251). (FIGS. 5C, 5D, and 5E) *E. chaffeensis* p120 peptides reacted with three HME patients (3, 18 and 20, respectively) sera. The OD readings represent the means for three wells (±standard deviations), with the OD of the buffer-only wells subtracted. The OD readings of peptide p120R-I1 were significantly higher than those of smaller overlapping peptides (I1-S1, I1-S3 and I1-S4, P<0.05 for all sera; I1-S2, P<0.05 for all patient sera). Normal dog or human serum did not recognize these peptides.

FIGS. 6A-6E. Immunoreactivity of E. canis p140 repeat overlapping synthetic peptides as determined by ELISA. (FIG. 6A) Six overlapping peptides spanning the E. canis p140 repeat unit. (FIGS. 6B, 6C, 6D, and 6E) E. canis p140 peptides reacted with anti-E. canis dog sera obtained from four naturally infected dogs (2160, 6, 10 and 18, respectively). The OD readings represent the means for three wells (±standard deviations), with the OD of the buffer-only wells subtracted. The OD readings of peptide R-4 were significantly higher than those of R-2 with half of the dog sera (10 and 18, P<0.05). The normal dog serum did not recognize these peptides.

(FIG. 10A) Ank200-N6 peptides (left) reacted with four HME patient serum samples (no. F3, F5, F13, and F22) and an anti-E. chaffeensis dog serum sample derived from an experimentally infected dog (no. 2251). The OD readings of peptide $N_6$-1 were significantly (P<0.05) higher than those of $N_6$-2, -3, and -4 for the dog serum sample and for most patient sera, and the OD readings of peptide N6-1a were significantly (P<0.05) higher than those of $N_6$-1b for all patient sera. (FIG. 10B) Ank200-N10 peptides (left) reacted with four HME patient serum samples (no. F2, F4, F5, and F21) and the dog serum sample. (FIG. 10C) Ank200-C6 peptides (left) reacted with four HME patient serum samples (no. F2, F4, F15, and SC07) and the dog serum sample. The OD readings of peptide $C_6$-4 were significantly (P<0.05) higher than those of $C_6$-1, -2, and -3 for all sera, and OD readings of peptide $C_6$-4b were significantly (P<0.05) higher than those of $C_6$-4a for all sera. The OD readings represent the mean values for three wells (±standard deviations), with the OD values of the buffer-only wells subtracted. Normal dog or human sera did not recognize these peptides.

FIGS. 12A-C. Immunoreactivity of overlapping synthetic peptides spanning E. chaffeensis TRP47-$N_4$ and synthetic TRP47-R and TRP47-C peptides as determined by ELISA. (FIG. 12A) Sequences of three overlapping peptides spanning the TRP47-$N_4$ fragment and TRP47-R and TRP47-C peptides. (FIG. 12B) TRP47-$N_4$ peptides reacted with five HME patient sera (nos. O15, 6, 9, 13, 18 and 19) by ELISA. (FIG. 12C) TRP47-R and TRP47-C peptides reacted with seven HME patient sera (nos. O3, O13, 4, 8, 10, 13 and 20) and an anti-E. chaffeensis dog serum (no. 2251) by ELISA. The OD readings represent the means for three wells (±standard deviations), with the OD of the buffer-only wells subtracted. The OD readings of peptide TRP47-R were significantly (P<0.05) higher than those of TRP47-C for all patient sera except for no. O3 and no. 13, for which the OD readings of peptide TRP47-C were significantly (P<0.05) higher than those of TRP47-R. The normal human or dog serum did not recognize TRP47 polypeptides.

(FIG. 13A) Synthetic epitope peptides of TRP32 ($R_3$+$R_4$), TRP47 ($N_4$-1+R+C), TRP120 (R-$I_1$) and Ank200 ($N_6$-1a+$N_{10}$-1+$C_6$-4b) reacted with 31 HME patient sera (nos. 1~31) and an anti-E. chaffeensis dog (no. 2251) serum. (FIG. 13B) An equal mixture of TRP32-$R_3$, TRP32-$R_4$ and TRP120-R-$I_1$ peptides as well as the recombinant TRP120 TR protein (rTRP120-TR, containing first two tandem repeats of TRP120 only) reacted with 31 HME patient (nos. 1~31) sera and an anti-E. chaffeensis dog (no. 2251) serum. The OD readings represent the means for three wells (±standard deviations), with the OD of the negative control (E. canis TRP36-2R peptide) wells subtracted. The cut-off OD (0.1) established for the positive reading is shown by a dotted line. The normal human or dog serum did not recognize these peptides.

DESCRIPTION OF ILLUSTRATIVE EMBODIMENTS

Figure 1:
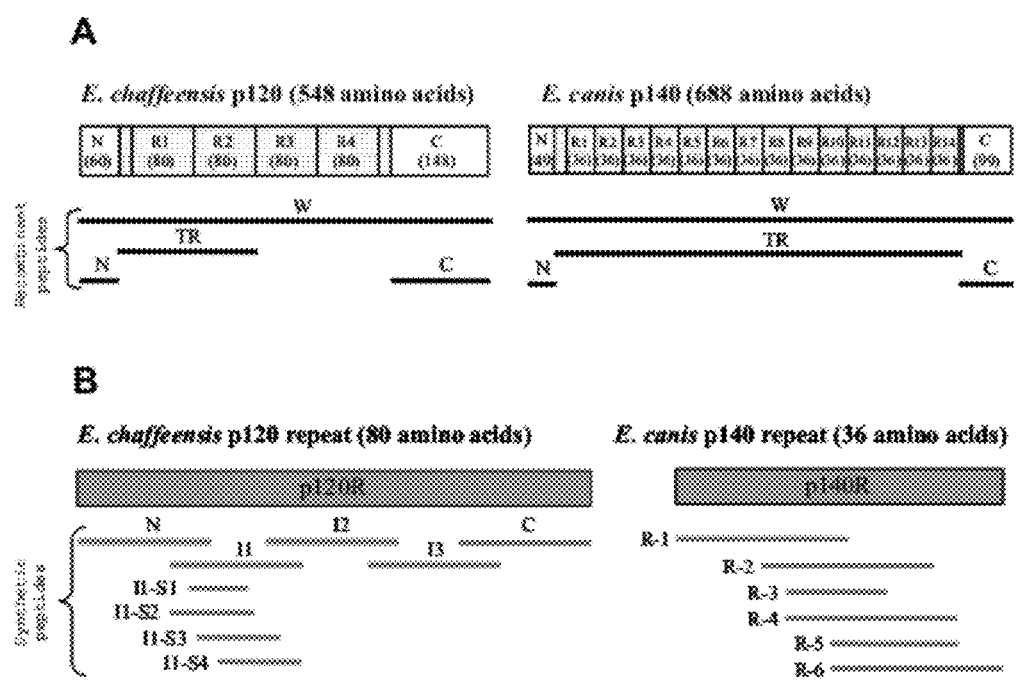
FIGS. 1A-1B.

The present invention is based, in part, on the discovery by the inventors of peptides corresponding to single continuous species-specific major epitopes within each of the E. chaffeensis p120 and E. canis p140 proteins. These immunoreactive peptides may be used for the detection of Ehrlichia infection, for example, by selectively binding Ehrlichia-specific antibodies in a biological sample, such as a blood or serum sample. Alternately, one or more of these peptides may be included in a vaccine formulation to induce a protective immune response in a subject against Ehrlichia.

Surprisingly, it was observed that various synthetic p120 immunoreactive peptides provided herein can display superior sensitivity and reactivity as compared to other immunoreactive proteins for the diagnosis of the emerging zoonosis human monocytotropic ehrlichiosis (HME) caused by Ehrlichia chaffeensis. As shown in the Examples below, the sensitivity and specificity of synthetic peptides representing immunodeterminants of E. chaffeensis were determined by enzyme-linked immunosorbent assay (ELISA). Thirty-one HME patient sera that had detectable E. chaffeensis antibodies (titers from 64 to 8192) by indirect fluorescent-antibody assay (IFA) were tested. All 31 sera reacted with at least one E. chaffeensis peptide and 30 sera (96.8%) with TRP120 peptide, 27 (87.1%) with TRP32 peptides, 24 (77.4%) with TRP47 peptides, 19 (61.3%) with Ank200 peptides, and 28 (90.3%) with recombinant TRP120-TR protein. A mixture of the two most sensitive peptides from TRP120 and TRP32 did not provide enhanced analytical sensitivity over the TRP120 alone. These results demonstrate that a p120 immunoreactive peptide may be used in a standardized sensitive point-of-care and/or reference laboratory immunodiagnostics for HME. To the inventors knowledge, these are the first studies to compare molecularly-defined major antibody epitopes with IFA for diagnosis of HME.

I. *EHRLICHIA* IMMUNODOMINANT PROTEINS AND IMMUNOREACTIVE PEPTIDES THEREOF

Most *Ehrlichia* species, including *Ehrlichia chaffeensis* and *Ehrlichia canis*, are obligately intracellular bacteria that exhibit tropism for mononuclear phagocytes (Winslow et al., 2005), interacting with these cells and other components of the immune system through a small subset of their constituent proteins (Collins et al., 2005; Hotopp et al., 2006; Frutos et al., 2006; Mavromatis et al., 2006). Among these host-pathogen interacting proteins are the major immunoreactive proteins which are recognized by antibodies in human and animal hosts (Doyle et al., 2006; McBride et al., 2003; McBride et al., 2000) and include p200, p120, p47 and VLPT in *Ehrlichia chaffeensis* and their orthologs in *Ehrlichia canis*, p200, p140, p36, and p19, respectively (Doyle et al., 2006; Luo et al., 2008; McBride et al., 2003; McBride et al., 2007; McBride et al., 2000; Nethery et al., 2007).

*E. chaffeensis* p120 and *E. canis* p140 are each major immunoreactive proteins that are differentially expressed and are secreted (Doyle et al., 2006; Popov, et al., 2000) by their respective organisms. Extensive variability in the number and/or sequence of tandem repeats in the *E. chaffeensis* and *E. canis* immunoreactive proteins is well documented (Chen et al., 1997; Doyle et al., 2006; Sumner et al., 1999). The p120 protein is a 120 kD protein that contains two to five serine-rich tandem repeats with 80-amino acids each, and the orthologous *E. canis* p140 is a 140 kD protein that contains twelve to fourteen serine-rich 36-amino acid TRs (Yabsley et al., 2003; Yu et al., 1997; Yu et al., 2000; Zhang et al., 2008). Disclosed herein is the mapping of a single species-specific epitope to each of the *Ehrlichia* proteins, p120 and p140, and in each protein, the epitope lies within the serine-rich, acidic tandem repeats. Such an epitope may, for example, be comprised in one or more immunoreactive peptides, i.e., p120/p140 immunoreactive peptides, from each of the *Ehrlichia* proteins and may be bound, identified, or recognized by an *Ehrlichia* specific antibody.

As used herein, the term "peptide" encompasses amino acid chains comprising less than about 100 amino acids and preferably less than about 50 amino acid residues, wherein the amino acid residues are linked by covalent peptide bonds. As used herein, an "antigenic peptide" is a peptide which, when introduced into a vertebrate, can stimulate the production of antibodies in the vertebrate, i.e., is antigenic, and wherein the antibody can selectively recognize and/or bind the antigenic peptide. An antigenic peptide may comprise an immunoreactive sequence derived from a p120 or p140 *Ehrlichia* protein, and may comprise additional sequences. The additional sequences may be derived from a native *Ehrlichia* antigen and may be heterologous, and such sequences may (but need not) be immunogenic.

As used herein, an "p120/p140 immunoreactive peptide" is an peptide which can selectively bind with an anti-p120 antibody or an anti-p140 antibody. For example, a p120/p140 immunoreactive peptide may bind one or more antibodies produced by a mammalian host (e.g., a dog or human) which was previously exposed to or infected by *Ehrlichia chaffeensis* or *Ehrlichia canis*. Accordingly, a "p120 immunoreactive peptide" refers to a peptide which can selectively bind an anti-p120 antibody, and "p140 immunoreactive peptide" refers to a peptide which can selectively bind an anti-p140 antibody. A p120/p140 immunoreactive peptide may have at least about, or comprise a sequence with at least about, 90%, 91%, 92%, 93%, 94%, 95%, 96%, 97%, 98%, 99%, or 100% sequence identity with any of SEQ ID NOs: 1, 2, 3, 4, 5, 6, 7, 8, 9, and/or 10 disclosed herein. The p120/p140 immunoreactive peptide may be from 10 to 45, 15 to 50, 15 to 45, 15 to 40, 16 to 45, 16 to 40, 18 to 35, or 20 to 30 amino acids in length, or any length or range derivable therein.

In certain embodiments, a p120/p140 peptide may be immunogenic or antigenic. For example, certain p120/p140 peptides may comprise an *Ehrlichia* antigen which, when introduced into a vertebrate, may stimulate the production of antibodies in the vertebrate which selectively recognize and/or bind a portion of an *Ehrlichia* p120 or p140 protein. It is envisioned that such peptides could be used to induce some degree of protective immunity.

A p120/p140 immunoreactive peptide may be a recombinant peptide, synthetic peptide, purified peptide, immobilized peptide, detectably labeled peptide, encapsulated peptide, or a vector-expressed peptide. In certain embodiments, a synthetic p120/p140 immunoreactive peptide may be used for diagnostic testing, and synthetic peptides may display certain advantages, such as a decreased risk of bacterial contamination, as compared to recombinantly expressed peptides. In select embodiments, an p120/p140 immunoreactive peptide of the present invention may be comprised in a kit, or may be immobilized onto a surface of a component of the kit. An p120/p140 immunoreactive peptide may also be comprised in a composition, such as, for example, a vaccine composition, which is formulated for administration to a human or canine subject.

Immobilized Immunoreactive Peptides

In certain embodiments, an p120/p140 immunoreactive peptide described herein may be used as diagnostic or prophylactic tools for detection of or immunization against *Ehrlichia* infection. In particular, p120/p140 immunoreactive peptides disclosed herein may be useful in solution-phase assays, or in assays in which the isolated p120/p140 immunoreactive peptide is immobilized on a surface of a support substrate. Alternatively, an p120/p140 immunoreactive peptide described herein may be comprised in a vaccine formulation to induce a protective immune response in a subject, or an immune response against *Ehrlichia chaffeensis* or *Ehrlichia canis*. One or more p120/p140 immunoreactive peptides may be immobilized on a surface by covalent attachment, encapsulation, or adsorption using methods generally known in the art, and may include the use of cross-linkers, capture molecules and such like, to which peptides may be coupled, conjugated, or cross-linked.

A p120/p140 immunoreactive peptide may be immobilized onto a surface of a support or a solid substrate; for example, the p120/p140 immunoreactive peptide may be immobilized directly or indirectly by coupling, cross-linking, adsorption, encapsulation, or by any appropriate method known in the art. By way of non-limiting example, binding of an p120/p140 immunoreactive peptide disclosed herein by adsorption to a well in a microtiter plate or to a membrane may be achieved by contacting the peptide, in a suitable buffer, with the well surface for a suitable amount of time. The contact time can vary with temperature, but is typically between about 1 hour and 1 day when using an amount of peptide ranging from about 50 ng to about 1 mg, and preferably about 500 ng.

In some embodiments, an p120/p140 immunoreactive peptide disclosed herein is covalently attached to a support substrate by first reacting the support with a reagent that will chemically react with both the support and a functional group (i.e., crosslink), such as a hydroxyl or amino group, on the peptide. For example, an p120/p140 immunoreactive peptide may be crosslinked to a surface through an amine or carboxylic group on either end of the peptide, and a peptide may be crosslinked through a group on each end of the peptide (i.e., head-to-tail crosslinked). Such peptomers (i.e., head-to-tail crosslinked or otherwise immobilized peptides) may be used with both diagnostic and therapeutic methods of the present invention.

Numerous support substrates for peptide immobilization are known in the art which may be employed with an p120/p140 immunoreactive peptide disclosed herein, formed from materials such as, for example, latex, polystyrene, nylon, nitrocellulose, cellulose, silica, agarose, inorganic polymers, lipids, proteins, sugars, or magnetic resin. A person of ordinary skill in the art may select the support substrate that is appropriate for a given application. In particular embodiments of the present invention, a support substrate may be a reaction chamber, a microplate well, a membrane, a filter, a paper, an emulsion, a bead, a microbead, a microsphere, a nanocrystal, a nanosphere, a dipstick, a card, a glass slide, a microslide, a lateral flow apparatus, a microchip, a comb, a silica particle, a magnetic particle, a nanoparticle, or a self-assembling monolayer.

Detectably-Labeled Immunoreactive peptides

A p120/p140 immunoreactive peptide may be conjugated to or attached to detectable label such as, for example, a radioactive isotope, a non-radioactive isotope, a particulate label, a fluorescent label, a chemiluminescent label, a paramagnetic label, an enzyme label or a colorimetric label. The detectably-labelled peptides may be used, e.g., in diagnostic or prophylactic methods and compositions. In certain embodiments, the peptide portion of the detectably labeled p120/p140 immunoreactive peptide may be immobilized on a surface of a support substrate. In other embodiments, the detectable label may be used to immobilize the detectably labeled p120/p140 immunoreactive peptide to the surface of a support substrate.

As used herein, "detectable label" is a compound and/or element that can be detected due to its specific functional properties, and/or chemical characteristics, the use of which allows the peptide to which it is attached be detected, and/or further quantified if desired.

Exemplary labels include, but are not limited to, a particulate label such as colloidal gold, a radioactive isotope such as astatine$^{211}$, $^{14}$-carbon, $^{51}$chromium, $^{36}$-chlorine, $^{57}$cobalt, $^{58}$cobalt, copper$^{67}$, gallium$^{67}$, $^{3}$hydrogen, iodine$^{123}$, iodine$^{125}$, iodine$^{131}$, indium$^{111}$, $^{59}$iron, $^{32}$phosphorus, rhenium186, rhenium188, $^{75}$selenium, $^{35}$sulphur, technicium99, technetium-99m or yttrium$^{90}$, a colorimetric label such as dinitrobenzene, dansyl chloride, dabsyl chloride, any of the azo, cyanin or triazine dyes, or chromophores disclosed in U.S. Pat. Nos. 5,470,932, 5,543,504, or 6,372,445, all of which are incorporated herein by reference; a paramagnetic label such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III), a fluorescent label such as Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, or Lucifer Yellow, an enzyme label such as urease, luciferase, alkaline phosphatase, (horseradish) hydrogen peroxidase, or glucose oxidase, or a chemiluminescent label such as luminol, phthalazinedione, and others disclosed in any of U.S. Pat. Nos. 4,373,932, 4,220,450, 5,470,723, and U.S. Patent Application 2007/0264664, all of which are incorporated herein by reference.

Methods of Producing an Immunoreactive Peptide

Certain p120/p140 immunoreactive peptide of the present invention may be synthesized, e.g., using solid-phase synthesis. Synthetic peptides may provide certain advantages over recombinant proteins; for example, synthetic peptides can be produced consistently in highly pure forms without contaminating *E. coli* proteins that can result in false positive reactions when utilizing recombinant proteins. In addition, peptides can be produced quickly and efficiently without costly and laborious purification procedures and need for defined expression vectors and hosts.

An isolated p120/p140 immunoreactive peptide disclosed herein may be produced by any appropriate method known in the organic chemistry arts. For example, such peptides may be produced using one of the established solid-phase peptide synthesis techniques, such as those of Merrifield, Carpino, or Atherton [Merrifield 1963; Carpino 1993, Atherton and Sheppard, 1989]. Peptides may be synthesized using equipment for automated peptide synthesis that is widely available from commercial suppliers such as Perkin Elmer (Foster City, Calif.). A p120/p140 immunoreactive peptide of the invention may also be chemically synthesized using solution-phase techniques such as those described in Carpino et al., (2003) or U.S. Patent Application 2009/0005535, both incorporated herein in their entirety by reference. Due to the length of the peptides, in certain embodiments, the peptides may be synthesized, e.g., using solid-phase peptide synthesis (SPPS), t-Boc solid-phase peptide synthesis, or Fmoc solid-phase peptide synthesis.

In alternative embodiments, an isolated p120/p140 immunoreactive peptide may be recombinantly prepared from a nucleic acid encoding the peptide. Such a nucleic acid may be operably linked to an expression vector and used to produce a peptide of the present invention using known methods. By way of nonlimiting example, a p120/p140 immunoreactive peptide may be expressed from a vector and isolated from the growth media of a host cell comprising the vector. Alternatively, the present p120/p140 immunoreactive peptides may be produced in a cell-free system from a nucleic acid encoding the peptide.

An immobilized p120/p140 immunoreactive peptide may be synthesized onto a support substrate, or conjugated, crosslinked, or adsorbed, either directly or indirectly onto a surface of a support substrate.

It is anticipated that virtually any method of peptide immobilization known in the art which would not impact the structure or function of the disclosed peptides may be used to immobilize a p120/p140 immunoreactive peptide. For example, peptide immobilization may be accomplished using a crosslinking or conjugation agent such as methyl-p-hydroxybenzimidate, N-succinimidyl-3-(4-hydroxyphenyl) propionate, using sulfosuccinimidyl 4-(N-maleimidomethyl) cyclohexane-1-carboxylate (sSMCC), N-[maleimidocaproyloxy]sulfosuccinimide ester (sEMCS), N-maleimidobenzoyl-N-hydroxysuccinimide ester (MBS), glutaraldehyde, 1-ethyl-3-(3-dimethylaminopropyl) carbodiimide (EDCI), Bis-diazobenzidine (BDB), or N-acetyl homocysteine thiolactone (NAHT), and others disclosed in any of U.S. Pat. Nos. 5,853,744, 5,891,506, 6,210,708, 6,617, 142, 6,875,750, 6,951,765, 7,163,677, and 7,282,194, each incorporated herein by reference. Peptides may be conjugated directly or indirectly to any of the commercially available support substrates having a surface coatings comprising crosslinkers, coupling agents, thiol or hydroxyl derivatizing agents, carboxyl- or amine-reactive groups such as of maleic anhydride (e.g., Pierce Immunotechnology Catalog and Handbook, at A12-A13, 1991).

In some embodiments, peptide of the invention may also be immobilized using metal chelate complexation, employing, for example, an organic chelating agent such a diethylenetriaminepentaacetic acid anhydride (DTPA); EDTA; N-chloro-p-toluenesulfonamide; and/or tetrachloro-3α-6 α-diphenylglycouril-3 attached to the antibody (U.S. Pat. Nos. 4,472,509 and 4,938,948, each incorporated herein by reference). Peptides can be immobilized by coupling to other peptides and to condensation groups immobilized on a surface or present in an immobilization buffer such as glutaraldehyde or periodate. Conjugates with fluorescence markers may also prepared in the presence of such agents or by reaction with an isothiocyanate. A peptide may be attached to a surface by conjugation, crosslinking or binding to an affinity binding agent such as biotin, streptavidin, a polysaccharide such as an alginate, a lectin, and the like.

In general, regardless of the method of preparation or immobilization status, the p120/p140 immunoreactive peptides disclosed herein are preferably prepared in a substantially pure form. Preferably, the p120/p140 immunoreactive peptides are at least about 80% pure, more preferably at least about 90% pure and most preferably at least about 99% pure.

Nuclieic Acids

In an aspect, the present invention provides a nucleic acid encoding an isolated p120/p140 immunoreactive peptide comprising a sequence that has at least about 90%, 91%, 92%, 93%, 94%, 95%, 96%, 97%, 98%, 99%, or 100% sequence identity to any of SEQ ID NOs. 1, 2, 3, 4, 5, 6, 7, 8, 9, and/or 10. Such a p120/p140 immunoreactive peptide may be from 10 to 45, 15 to 40, 15 to 30, 18 to 35, or 20 to 30 amino acids in length, or any range derivable therein. The term "nucleic acid" is intended to include DNA and RNA and can be either double stranded or single stranded.

Some embodiments of the present invention provide recombinantly produced p120/p140 immunoreactive peptides which can specifically bind *Ehrlichia* specific antibodies. Accordingly, a nucleic acid encoding a p120/p140 immunoreactive pe Biological Functional Equivalents Preferred p120/p140 immunoreactive peptides or analogs thereof specifically or preferentially bind an *Ehrlichia* p120 or p140 specific antibody. Determining whether or to what degree a particular p120/p140 immunoreactive peptide or labeled peptide, or an analog thereof, can bind an *Ehrlichia* p120 or p140 specific antibody can be assessed using an in vitro assay such as, for example, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and/or an avidity assay.

An p120/p140 immunoreactive peptide of the present invention may be modified to contain amino acid substitutions, insertions and/or deletions that do not alter their respective interactions with anti-*Ehrlichia* antibody binding regions. Such a biologically functional equivalent of an p120/p140 immunoreactive peptide derived from an *Ehrlichia* p120 or p140 protein could be a molecule having like or otherwise desirable characteristics, i.e., binding of *Ehrlichia* specific antibodies. As a nonlimiting example, certain amino acids may be substituted for other amino acids in an p120/p140 immunoreactive peptide disclosed herein without appreciable loss of interactive capacity, as demonstrated by detectably unchanged antibody binding. It is thus contemplated that an p120/p140 immunoreactive peptide disclosed herein (or a nucleic acid encoding such a peptide) which is modified in sequence and/or structure, but which is unchanged in biological utility or activity remains within the scope of the present invention.

It is also well understood by the skilled artisan that, inherent in the definition of a biologically functional equivalent peptide, is the concept that there is a limit to the number of changes that may be made within a defined portion of the molecule while still maintaining an acceptable level of equivalent biological activity. Biologically functional equivalent peptides are thus defined herein as those peptides in which certain, not most or all, of the amino acids may be substituted. Of course, a plurality of distinct peptides with different substitutions may easily be made and used in accordance with the invention.

The skilled artisan is also aware that where certain residues are shown to be particularly important to the biological or structural properties of a peptide, e.g., residues in specific epitopes, such residues may not generally be exchanged. This may be the case in the present invention, as a mutation in an p120/p140 immunoreactive peptide disclosed herein could result in a loss of species-specificity and in turn, reduce the utility of the resulting peptide for use in methods of the present invention. Thus, peptides which are antigenic (i.e., bind anti-*Ehrlichia* antibodies specifically) and comprise conservative amino acid substitutions are understood to be included in the present invention. Conservative substitutions are least likely to drastically alter the activity of a protein. A "conservative amino acid substitution" refers to replacement of amino acid with a chemically similar amino acid, i.e., replacing nonpolar amino acids with other nonpolar amino acids; substitution of polar amino acids with other polar amino acids, acidic residues with other acidic amino acids, etc.

Amino acid substitutions, such as those which might be employed in modifying an p120/p140 immunoreactive peptide disclosed herein are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

The invention also contemplates isoforms of the p120/p140 immunoreactive peptides disclosed herein. An isoform contains the same number and kinds of amino acids as a peptide of the invention, but the isoform has a different molecular structure. The isoforms contemplated by the present invention are those having the same properties as a peptide of the invention as described herein.

Nonstandard amino acids may be incorporated into proteins by chemical modification of existing amino acids or by de novo synthesis of a peptide disclosed herein. A nonstandard amino acid refers to an amino acid that differs in chemical structure from the twenty standard amino acids encoded by the genetic code.

In select embodiments, the present invention contemplates a chemical derivative of an p120/p140 immunoreactive peptide disclosed herein. "Chemical derivative" refers to a peptide having one or more residues chemically derivatized by reaction of a functional side group, and retaining biological activity and utility. Such derivatized peptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include those peptides which comprise one or more naturally occurring amino acids derivatives of the twenty standard amino acids. For example, 4-hydroxyproline may be substituted for serine; and ornithine may be substituted for lysine.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The amino acids described herein are preferred to be in the "L" isomeric form. However, residues in the "D" isomeric form can be substituted for any L-amino acid residue, as long as the desired functional properties set forth herein are retained by the protein. In keeping with standard protein nomenclature, *J. Biol. Chem.,* 243:3552-59 (1969), abbreviations for amino acid residues are known in the art.

Peptidomimetics

In addition to the biological functional equivalents discussed above, the inventors also contemplate that structurally similar compounds may be formulated to mimic the key portions of an p120/p140 immunoreactive peptide of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, alpha-helix mimetics are disclosed in U.S. Pat. Nos. 5,446,128; 5,710,245; 5,840,833; and 5,859,184. These structures render the peptide more thermally stable, also increase resistance to proteolytic degradation. Six, seven, eleven, twelve, thirteen and fourteen membered ring structures are disclosed.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties. Methods for generating conformationally restricted beta turns and beta bulges are described, for example, in U.S. Pat. Nos. 5,440,013; 5,618,914; and 5,670,155.

Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

II. EHRLICHIOSIS AND DETECTING *EHRLICHIA* INFECTION

Ehrlichiosis in humans generally refers to infections caused by obligate intracellular bacteria in the family Anaplasmataceae, chiefly in the genera *Ehrlichia* and *Anaplasma*. The majority of cases of human ehrlichiosis (HE) are caused by 3 distinct species: *Ehrlichia chaffeensis*, chief among them (Dumler et al., 2007). *Ehrlichia* infections in animals are also referred to as Ehrlichiosis, along with a variety of diseases caused by a diverse group of pathogens from genuses *Ehrlichia, Anaplasma, Neorickettsia*, and *Cowdria* (Dumler et al., 2007). *Ehrlichia* infections are sustained mostly in monocytes or granulocytes, and studies have demonstrated that antibodies play an essential role in the immune response to *Ehrlichia* infection (Feng et al., 2004; Winslow et al., 2003; Winslow et al., 2000; Yager et al., 2005).

Accordingly, select embodiments of the present invention provide methods of detecting antibodies that specifically bind an *Ehrlichia* organism in a sample. Such a method may involve contacting an isolated p120/p140 immunoreactive peptide disclosed herein, with the test sample, under conditions that allow peptide-antibody complexes to form, and detecting the peptide-antibody complexes. In these embodiments, the detection of the peptide-antibody complexes is an indication that antibodies specific for an *Ehrlichia* organism are present in the test sample, and the absence of the peptide-antibody complexes is an indication that antibodies specific an *Ehrlichia* organism are not present in the test sample.

In multiple embodiments, the detection of an p120/p140 immunoreactive peptide disclosed herein bound to an *Ehrlichia* specific antibody (i.e., a peptide-antibody complex) may be accomplished using an enzyme-linked immunoassay, a radioimmunoassay, an immunoprecipitation, a fluorescence immunoassay, a chemiluminescent assay, an immunoblot assay, a lateral flow assay, a flow cytometry assay, a mass spectrometry assay, latex agglutination, an indirect hemagglutination assay (IHA), complement fixation, an inhibition assay, an avidity assay, a dipstick test, or a particulate-based assay. In preferred embodiments, peptide-antibody complexes described herein are detected using an enzyme-linked immunoassay, a lateral flow assay, or a particle-based assay.

As used herein, a "sample" is any sample that comprises or is suspected to comprise antibodies. Preferably, the sample is whole blood, sputum, serum, plasma, saliva, cerebrospinal fluid or urine. In some embodiments, the sample is a blood, serum or plasma sample obtained from a subject or patient.

Ehrlichiosis caused by an *Ehrlichia chaffeensis* infection in humans presents with flu-like symptoms of fever, chills, headache, and muscle aches. In more severe cases, nausea, loss of appetite, weight loss, abdominal pain, cough, diarrhea and change in mental status may also be observed. Ehrlichiosis in humans is potentially fatal.

In dogs, ehrlichiosis is most often caused by either *Ehrlichia chaffeensis* or *Ehrlichia canis* bacteria, and progresses in three phases: an acute phase, a subclinical phase, and a chronic phase. The acute phase normally extends weeks after infection and features symptoms similar to those of human ehrlichiosis, i.e., fever, lethargy, loss of appetite, shortness of breath, joint pain and stiffness, and can include more sever symptoms such as anemia, depression, bruising, and enlarged lymph nodes, liver, and spleen. The subclinical phase can persist for years and most often presents no symptoms, although antibodies to *Ehrlichia* antigens may be detectable. The chronic phase of *Ehrlichia* infection generally features recurring symptoms of weight loss, anemia, neurological dysfunction, bleeding, ocular inflammation, leg edema, and fever, and presents a blood profile which often leads to a misdiagnosis of leukemia. An *Ehrlichia* infection that progesses to the chronic stage of disease is often fatal.

The nonspecific symptoms of an *Ehrlichia* infection and their resemblance to mild and severe influenza symptoms makes diagnosis of Ehrlichiosis difficult in humans and dogs. Diagnosis is further hampered by current laboratory testing procedures for *Ehrlichia* infection which are not point-of-care tests, i.e., the tests are not available in most hospitals, clinics, and physician or veterinarian offices where a patient can receive treatment.

Accordingly, select embodiments of the present invention provide methods of identifying an *Ehrlichia* infection in a subject. Such a method may involve contacting a sample from the subject with an isolated p120/p140 immunoreactive peptide disclosed herein under conditions that allow peptide-antibody complexes to form, and detecting the peptide-antibody complexes. In these embodiments, the detection of the peptide-antibody complexes is an indication that the subject has an *Ehrlichia* infection. The *Ehrlichia* organism may be an *Ehrlichia chaffeensis* organism or an *Ehrlichia canis* organism. In some embodiments, the subject is a human or a dog. As with other methods disclosed herein, the detection step may be accomplished using any appropriate type of assay known in the art, and may be preferably accomplished using a lateral flow assay or an ELISA.

The terms "subject" and "patient" are used interchangeably herein, and may refer to a mammal, especially a human or a dog. In certain embodiments, a "subject" or "patient" refers to a mammalian *Ehrlichia* host (i.e., animal infected with an *Ehrlichia* organism). An *Ehrlichia* host may be, for example, human or non-human primate, bovine, canine, caprine, cavine, corvine, epine, equine, feline, hircine, lapine, leporine, lupine, murine, ovine, porcine, racine, vulpine, and the like, including livestock, zoological specimens, exotics, as well as companion animals, pets, and any animal under the care of a veterinary practitioner. A subject may be or may not be infected with an *Ehrlichia* organism, and a subject may be a mammal suspected of being infected with an *Ehrlichia* organism.

Without wishing to be bound by theory, the p120/p140 immunoreactive peptides disclosed herein each comprise at least a part of a major *Ehrlichia* epitope that accounts for a species-specific immunogenicity in humans and animals. The term "epitope" is used herein to indicate that portion of an immunogenic substance that is specifically identified, recognized, and bound by, an antibody or cell-surface receptor of a host immune system that has mounted an immune response to the immunogenic substance as determined by any method known in the art. (see, for example, Geysen et al., 1984). Thus, an epitope that is "species-specific" is an epitope that can be used to differentiate one species of the *Ehrlichia* genus from another *Ehrlichia* species. By way of non-limiting example, an p120/p140 immunoreactive peptide that has at least 95% identity with SEQ ID NO:1 from *Ehrlichia chaffeensis* comprises an epitope that may be distinguishable by the immune system of a host mammal from an p120/p140 immunoreactive peptide that has at least 95% identity with SEQ ID NO:2 from *Ehrlichia canis*.

Accordingly, an aspect of the present invention provides a method of distinguishing between an *Ehrlichia chaffeensis* infection and an *Ehrlichia canis* infection in a subject. Such a method may comprise contacting a first sample from the subject with an isolated p120 immunoreactive peptide (e.g., comprising an amino acid sequence having about 95% or more sequence identity with a peptide selected from the group consisting of SEQ ID NOs 1, 4, 5, and 6); contacting a second sample from the subject with an isolated p140 immunoreactive peptide (e.g., comprising an amino acid sequence having about 95% or more sequence identity with a peptide selected from the group consisting of SEQ ID NOs: 2, 7, 8, 9, and 10); detecting the presence or absence of peptide-antibody complexes in each of the first and second samples. In these embodiments, the presence of peptide-antibody complexes in the first sample is an indication that the subject has an *Ehrlichia chaffeensis* infection, and the presence of peptide-antibody complexes in the second sample is an indication that the subject has an *Ehrlichia canis* infection.

Particular embodiments relate to determining whether a subject has been immunized against *Ehrlichia* or is actively infected with an *Ehrlichia* organism. In these embodiments, the method comprises contacting a sample from the subject with at least one isolated p120/p140 immunoreactive peptide disclosed herein that is not a component of an *Ehrlichia* vaccine, and detecting whether an antibody in the sample specifically binds to the isolated p120/p140 immunoreactive peptide. According to the method, if an antibody in the sample specifically binds to the isolated p120/p140 immunoreactive peptide, then the subject has an active *Ehrlichia* infection, and if an antibody does not specifically bind to the isolated p120/p140 immunoreactive peptide, then the subject is either previously immunized with an *Ehrlichia* vaccine or is not infected with an *Ehrlichia* organism. An *Ehrlichia* organism may be an *Ehrlichia chaffeensis* organism or an *Ehrlichia canis* organism.

A p120/p140 immunoreactive peptide may be used to bind an *Ehrlichia*-specific antibody using a variety of methods or kits. The specific binding between an antibody and an p120/p140 immunoreactive peptide of the present invention may therefore be assessed by any appropriate method known in the art including, but not limited to, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and avidity assay. Exemplary methods of detecting the binding of an *Ehrlichia*-specific antibody to an p120/p140 immunoreactive peptide disclosed herein may include, for example, an ELISA performed in a microplate, a lateral flow test performed using a dipstick or lateral flow device, or a particulate-based suspension array assay performed using the Bio-Plex® system (Bio-Rad Laboratories, Hercules, Calif., USA).

ELISA

In certain embodiments, the detection of an peptide-antibody complex described herein is accomplished using an enzyme linked immunosorbent assay (ELISA). This assay may be performed by first contacting an p120/p140 immunoreactive peptide that has been immobilized on a solid support, commonly the well of a microtiter plate, with the sample, such that antibodies specific for the peptide within the sample are allowed to bind to the immobilized peptide. Unbound sample is then removed from the immobilized peptide and a detection reagent capable of binding to the immobilized antibody-polypeptide complex is added. The amount of detection reagent that remains bound to the solid support is then determined using a method appropriate for the specific detection reagent.

In some embodiments, the detection reagent contains a binding agent (such as, for example, Protein A, Protein G, immunoglobulin, lectin or free antigen) conjugated to a reporter group or label. Exemplary reporter groups or labels include enzymes (such as horseradish peroxidase), substrates, cofactors, inhibitors, dyes, radionuclides, luminescent groups, fluorescent groups and biotin. The conjugation of binding agent to reporter group or label may be achieved using standard methods known to those of ordinary skill in the art. Common binding agents may also be purchased conjugated to a variety of reporter groups from many commercial sources (e.g., Zymed Laboratories, San Francisco, Calif.; and Pierce, Rockford, Ill.).

In an aspect of the present invention, the presence or absence of *Ehrlichia* specific antibodies may be determined in the sample by comparing the level of a signal detected from a reporter group or label in the sample with the level of a signal that corresponds to a control sample or predetermined cut-off value. In certain embodiments, the cut-off value may be the average mean signal obtained when the immobilized p120/p140 immunoreactive peptide is incubated with samples from an uninfected subject. The cut-off value may be determined using a statistical method or computer program.

Lateral Flow Tests

Lateral flow tests may also be referred to as immunochromatographic strip (ICS) tests or simply strip-tests. In general, a lateral flow test is a form of assay in which the test sample flows laterally along a solid substrate via capillary action, or alternatively, under fluidic control. Such tests are often inexpensive, require a very small amount (e.g., one drop) of sample, and can typically be performed reproducibly with minimal training. The economical simplicity and robustness of many lateral flow assay formats makes these types of tests ideal for identifying an *Ehrlichia* infection at the point of care, which is particularly important when the subject is, for example, a dog exhibiting detectable antibodies during the treatable acute phase of infection.

Exemplary lateral flow device formats include, but are not limited to, a dipstick, a card, a chip, a microslide, and a cassette, and it is widely deomonstrated in the art that the choice of format is largely dependent upon the features of a particular assay. Accordingly, lateral flow devices are now ubiquitous in human and verinarian medicine and quite varied, providing many options to the ordinarily skilled artisan for detecting a peptide-antibody complex in a sample using a lateral flow assay (See any of U.S. Pat. Nos. 7,344,893, 7,371, 582, 6,136,610, and U.S. Patent Applications, 2005/0250141 and 2005/0047972, each incorporated herein by reference.) By way of a nonlimiting example, a sample from a subject suspected of having an *Ehrlichia* infection is applied to a lateral flow device comprising at least a sample zone and a binding zone. The sample may be a serum sample, and may be drawn laterally from the sample zone to the binding zone which comprises an p120/p140 immunoreactive peptide disclosed herein immobilized to a surface of the lateral flow device. In this example, the binding of the immobilized p120/p140 immunoreactive peptides on the lateral flow device is an indication that *Ehrlichia* specific antibodies are present in the sample from the subject, indicating an *Ehrlichia* infection in the subject.

In related embodiments, an ELISA assay as described above may be performed in a rapid flow-through, lateral flow, or strip test format, wherein the antigen is immobilized on a membrane, such as a nitrocellulose membrane. In this flow-through test, *Ehrlichia* antibodies within the sample bind to the immobilized p120/p140 immunoreactive peptide as the sample passes through the membrane. A detection reagent, such as protein A labeled with gold, a fluorophore, or a chromophore, binds to the peptide-antibody complex as the solution containing the detection reagent flows through the membrane. The detection peptide-antibody complexes bound to detection reagent may then be performed as is appropriate for the detection reagent used.

In an aspect, a flow-through format ELISA may be performed in which one end of the membrane to which p120/p140 immunoreactive peptide is immobilized may be immersed in a solution containing the sample, or the sample may be added to an area (i.e., a sample zone) at one end of the membrane. The sample migrates along the membrane through a region (i.e., a labeling zone) comprising the detection reagent, and flows to the area (i.e., a binding zone) comprising an immobilized p120/p140 immunoreactive peptide disclosed herein. An accumulation of detection reagent at the binding zone indicates the presence of *Ehrlichia* specific antibodies in the sample.

Typically, a flow-through ELISA may feature a detection reagent applied to a test strip in a pattern, such as a line, that can be read visually. As with other lateral flow tests, the absence of such a pattern indicates a negative result. It is within the ability of an ordinarily skilled artisan to select an amount of p120/p140 immunoreactive peptide for immobilization on the membrane that can generate a visually discernible pattern when the biological sample contains a level of antibodies that would be sufficient to generate a positive signal in a standard format ELISA. Preferably, the amount of peptide immobilized on the membrane ranges from about 25 ng to about 1 mg.

Particulate-Based Assays

In general, particle-based assays use a capture-binding partner, such as an antibody or an antigen in the case of an immunoassay, coated on the surface of particles, such as microbeads, crystals, chips, or nanoparticles. Particle-based assays may be effectively multi-plexed or modified to assay numerous variables of interest by incorporating fluorescently labeled particles or particles of different sizes in a single assay, each coated or conjugated to one or more labeled capture-binding partners. The use of sensitive detection and amplification technologies with particle-based assay platforms known in the art has resulted in numerous flexible and sensitive assay systems to choose from in performing a method described herein. For example, a multi-plex particle-based assay such as the suspension array Bio-Plex® assay system available from Bio-Rad Laboratories, Inc. (Hercules, Calif.) and Luminex, Inc. (Austin, Tex.) may be useful in identifying *Ehrlichia* antibodies in a sample.

In an aspect, the present invention contemplates the immobilization of an isolated p120/p140 immunoreactive peptide disclosed herein on a surface of a particle for use in a particle-based immunoassay. As described herein, methods of peptide immobilization onto support surfaces is well known in the art. In a preferred embodiment, a labeled p120/p140 immunoreactive peptide disclosed herein is immobilized onto a surface of a particle and the peptide-particle complex is employed in an ELISA or in a flow cytometry assay according to established protocols.

III. *EHRLICHIA* VACCINE COMPOSITIONS AND USES THEREOF

In select embodiments, it is contemplated that an p120/p140 immunoreactive peptide of the present invention may be comprised in a vaccine composition and administered to a subject to induce a protective immune response in the subject that may substantially prevent or ameliorate infection in the subject by an *Ehrlichia* organism such as *Ehrlichia chaffeensis* or *Ehrlichia canis*. A vaccine composition for pharmaceutical use in a subject may comprises an p120/p140 immunoreactive peptide composition disclosed herein and a pharmaceutically acceptable carrier.

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1289-1329, 1990, incorporated herein by reference). Except insofar as any conventional carrier is incompatible with the active ingredient, its use in the vaccine compositions of the present invention is contemplated.

As used herein, a "protective immune response" refers to a response by the immune system of a mammalian host to an *Ehrlichia* antigen which results in increased recognition of the antigen and antibody production by the immune system of the mammalian host upon subsequent exposure to an *Ehrlichia* pathogen. A protective immune response may substantially reduce or prevent symptoms as a result of a subsequent exposure to *Ehrlichia chaffeensis* or *Ehrlichia canis*.

In some embodiments, a vaccine composition of the present invention may comprise an p120/p140 immunoreactive peptide (e.g., having a sequence that has at least about 90%, 91%, 92%, 93%, 94%, 95%, 96%, 97%, 98%, 99%, or 100% sequence identity to any of SEQ ID NOs. 1, 4, 5, 6, or SEQ, ID NOs. 2, 7, 8, 9, and 10). The vaccine composition may comprises at least one p120 immunoreactive peptide (e.g., having a sequence that has at least about 90%, 91%, 92%, 93%, 94%, 95%, 96%, 97%, 98%, 99%, or 100% sequence identity to any of SEQ ID NOs. 1, 4, 5, 6). A vaccine composition comprising a p120 immunoreactive peptide may be used to induce a protective immune response against *Ehrlichia chaffeensis*. The vaccine composition may comprise least one p140 immunoreactive peptide (e.g., having a sequence that has at least about 90%, 91%, 92%, 93%, 94%, 95%, 96%, 97%, 98%, 99%, or 100% or more sequence identity to any of SEQ, ID NOs. 2, 7, 8, 9, and 10). A vaccine composition comprising a p140 immunoreactive peptide may be used to induce a protective immune response against *Ehrlichia canis*.

A person having ordinary skill in the medical arts will appreciate that the actual dosage amount of a vaccine composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, vaccine compositions may comprise, for example, at least about 0.1% of an p120/p140 immunoreactive peptide. In other embodiments, the an active compound may comprise between about 2% to about 75% of the weight of the unit, or between about 25% to about 60%, for example, and any range derivable therein. As with many vaccine compositions, frequency of administration, as well as dosage, will vary among members of a population of animals or humans in ways that are predictable by one skilled in the art of immunology. By way of nonlimiting example, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1-36 week period. Preferably, 3 doses are administered, at intervals of 3-4 months, and booster vaccinations may be given periodically thereafter.

In some embodiments, a "suitable dose" is an amount of an p120/p140 immunoreactive peptide that, when administered as described above, is capable of raising an immune response in an immunized patient sufficient to protect the subject from an *Ehrlichia* infection in subsequent exposures to *Ehrlichia* organisms. In general, the amount of peptide present in a suitable dose (or produced in situ by the nucleic acid in a dose) ranges from about 1 pg to about 500 mg per kg of host, typically from about 10 pg to about 10 mg, preferably from about 100 pg to about 1 mg and more preferably from about 100 pg to about 100 microgram.

A vaccine composition of the present invention may comprise different types of carriers depending on whether it is to be administered in solid, liquid or aerosol form, and whether it needs to be sterile for such routes of administration as injection. A vaccine composition disclosed herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularly, orally, topically, locally, and by inhalation, injection, infusion, continuous infusion, lavage, and localized perfusion. A vaccine composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference).

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Of particular interest in an aspect of the present invention is a vaccine composition that may be administered by microstructured transdermal or ballistic particulate delivery. Microstructures as carriers for vaccine formulation are a desirable configuration for vaccine applications and are widely known in the art (Gerstel and Place 1976 (U.S. Pat. No. 3,964,482); Ganderton and McAinsh 1974 (U.S. Pat. No. 3,814,097); U.S. Pat. Nos. 5,797,898, 5,770,219 and 5,783,208, and U.S. Patent Application 2005/0065463). Such a vaccine composition formulated for ballistic particulate delivery may comprise an isolated p120/p140 immunoreactive peptide disclosed herein immobilized on a surface of a support substrate. In these embodiments, a support substrate can include, but is not limited to, a microcapsule, a microparticle, a microsphere, a nanocapsule, a nanoparticle, a nanosphere, or a combination thereof Microstructures or ballistic particles that serve as a support substrate for an p120/p140 immunoreactive peptide disclosed herein may be comprised of biodegradable material and non-biodegradable material, and such support substrates may be comprised of synthetic polymers, silica, lipids, carbohydrates, proteins, lectins, ionic agents, crosslinkers, and other microstructure components available in the art. Protocols and reagents for the immobilization of a peptide of the invention to a support substrate composed of such materials are widely available commercially and in the art.

In other embodiments, a vaccine composition comprises an immobilized or encapsulated p120/p140 immunoreactive peptide disclosed herein and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868 and 5,795,587, each of which is specifically incorporated in its entirety by reference).

In addition to the methods of delivery described herein, a number of alternative techniques are also contemplated for administering the disclosed vaccine compositions. By way of nonlimiting example, a vaccine composition may be administered by sonophoresis (i.e., ultrasound) which has been used and described in U.S. Pat. No. 5,656,016 for enhancing the rate and efficacy of drug permeation into and through the circulatory system; intraosseous injection (U.S. Pat. No. 5,779,708), or feedback-controlled delivery (U.S. Pat. No. 5,697,899), and each of the patents in this paragraph is specifically incorporated herein in its entirety by reference.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

A peptide may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

IV. *EHRLICHIA* DETECTION AND VACCINATION KITS

Various embodiments of the present invention are concerned with kits for the detection of antibodies in a sample that specifically bind an *Ehrlichia* organism. The kits may thus be used for the diagnosis or identification of an *Ehrlichia* infection in a subject. In other embodiments, the invention provides kits for distinguishing between an *Ehrlichia chaffeensis* infection and an *Ehrlichia canis* infection in a subject, or for determining whether a subject has been immunized against *Ehrlichia* or is actively infected with an *Ehrlichia* organism. In still other embodiments, kits are provided for vaccination of a subject against *Ehrlichia chaffeensis* infection and an *Ehrlichia canis* infection.

In select embodiments, a kit of the present invention may be used to perform a method disclosed herein. For example, a kit may be suitable for detecting *Ehrlichia* antibodies in a sample, for identifying an *Ehrlichia* infection individual, for distinguishing between an *Ehrlichia chaffeensis* infection and an *Ehrlichia canis* infection in a subject, for determining whether a subject has been immunized against *Ehrlichia* or is actively infected with an *Ehrlichia* organism, or for vaccinating a subject against an *Ehrlichia* organism. In these embodiments, one or more p120/p140 immunoreactive peptides (e.g., having about 95% or more sequence identity with any of SEQ ID NOs 1, 2, 3, 4, 5, 6, 7, 8, 9, and 10) may be comprised in the kit. The p120/p140 immunoreactive peptide in the kit may be detectably labeled or immobilized on a surface of a support substrate also comprised in the kit. The p120/p140 immunoreactive peptide(s) may, for example, be provided in the kit in a suitable form, such as sterile, lyophilized, or both.

The support substrate comprised in a kit of the invention may be selected based on the method to be performed. By way of nonlimiting example, a support substrate may be a multi-well plate or microplate, a membrane, a filter, a paper, an emulsion, a bead, a microbead, a microsphere, a nanobead, a nanosphere, a nanoparticle, an ethosome, a liposome, a niosome, a transferosome, a dipstick, a card, a celluloid strip, a glass slide, a microslide, a biosensor, a lateral flow apparatus, a microchip, a comb, a silica particle, a magnetic particle, or a self-assembling monolayer.

As appropriate to the method being performed, a kit may further comprise one or more apparatuses for delivery of a composition to a subject or for otherwise handling a composition of the invention. By way of nonlimiting example, a kit may include an apparatus that is a syringe, an eye dropper, a ballistic particle applicator (e.g., applicators disclosed in U.S. Pat. Nos. 5,797,898, 5,770,219 and 5,783,208, and U.S. Patent Application 2005/0065463), a scoopula, a microslide cover, a test strip holder or cover, and such like.

A detection reagent for labeling a component of the kit may optionally be comprised in a kit for performing a method of the present invention. In particular embodiments, the labeling or detection reagent is selected from a group comprising reagents used commonly in the art and including, without limitation, radioactive elements, enzymes, molecules which absorb light in the UV range, and fluorophores such as fluorescein, rhodamine, auramine, Texas Red, AMCA blue and Lucifer Yellow. In other embodiments, a kit is provided comprising one or more container means and a BST protein agent already labeled with a detection reagent selected from a group comprising a radioactive element, an enzyme, a molecule which absorbs light in the UV range, and a fluorophore.

In particular embodiments, the present invention provides a kit for detecting anti-*Ehrlichia* antibodies in a sample which may also be used for identification of an *Ehrlichia* infection in a subject, for distinguishing between an *Ehrlichia chaffeensis* infection and an *Ehrlichia canis* infection in a subject, and/or for determining whether a subject has been immunized against *Ehrlichia* or is actively infected with an *Ehrlichia* organism. Such a kit may comprise one or more p120/p140 immunoreactive peptides (e.g., having about 95% or more sequence identity with any of SEQ ID NOs 1, 2, 3, 4, 5, 6, 7, 8, 9, and/or 10), and the peptides may be detectably labeled and immobilized to one or more support substrates comprised in the kit.

In some embodiments, a kit comprises an p120/p140 immunoreactive peptide having about 95% or more sequence identity with SEQ ID NO 1 and/or an p120/p140 immunoreactive peptide having about 95% or more sequence identity with SEQ ID NO 2. The peptides may be immobilized to one or more separate lateral flow assay devices, such as a nitrocellulose test strips. In these embodiments, each of the test strips may further comprises a detection reagent, for example, a chromophore-labeled protein A. Such a kit may further comprise one or more containers for sample material, one or more diluents for sample dilution, and one or more control indicator strips for comparison.

When reagents and/or components comprising a kit are provided in a lyophilized form (lyophilisate) or as a dry powder, the lyophilisate or powder can be reconstituted by the addition of a suitable solvent. In particular embodiments, the solvent may be a sterile, pharmaceutically acceptable buffer and/or other diluent. It is envisioned that such a solvent may also be provided as part of a kit.

When the components of a kit are provided in one and/or more liquid solutions, the liquid solution may be, by way of non-limiting example, a sterile, aqueous solution. The compositions may also be formulated into an administrative composition. In this case, the container means may itself be a syringe, pipette, topical applicator or the like, from which the formulation may be applied to an affected area of the body, injected into a subject, and/or applied to or mixed with the other components of the kit.

V. EXAMPLES

The following examples are included to demonstrate preferred embodiments of the invention. It should be appreciated by those of skill in the art that the techniques disclosed in the following example represent techniques identified by the applicant to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Major Species-Specific Antibody Epitopes of the *Ehrlichia chaffeensis* p120 and *Ehrlichia canis* p140 Orthologs in Surface-Exposed Tandem Repeat Regions Here is presented the identification and characterization of the immunodeterminants of the *E. chaffeensis* p120 and *E. canis* p140. Major antibody epitope-containing regions of both p120 and p140 were localized to the TR regions, which reacted strongly by Western immunoblot with antibodies in sera from *E. chaffeensis*-infected dogs/patients and *E. canis*-infected dogs, respectively. Single continuous species-specific major epitopes within the *E. chaffeensis* p120 and *E. canis* p140 TRs were mapped to homologous surface-exposed glutamate/aspartate-rich regions (19 to 22 amino acids). In addition, minor cross-reactive epitopes were localized to homologous N- and C-terminal regions of p120 and p140. Furthermore, although the native and recombinant p120 and p140 proteins exhibited larger-than-predicted molecular masses, posttranslational modifications were not present on abnormally migrating p120 and p140 TR recombinant proteins as determined by matrix-assisted laser desorption ionization-time-of-flight mass spectrometry.

Materials and Methods

Culture and purification of *Ehrlichiae*. *E. chaffeensis* (Arkansas strain) and *E. canis* (Jake strain) were propagated and purified by size exclusion chromatography as previously described (McBride et al., 2001; Rikihisa et al., 1992). The fractions containing bacteria were frozen and utilized as antigen and DNA sources.

Preparation of *Ehrlichia* Genomic DNA and Antigen. Genomic DNA and antigen were purified from *E. chaffeensis* (Arkansas strain) and *E. canis* (Jake strain) as previously described (McBride et al., 1996). *Ehrlichia*-infected DH82 cell culture supernatants (0.5 ml) were collected five days postinfection without disturbing the cell monolayer and clarified by high speed centrifugation (10,000 g for 5 min) to remove *Ehrlichiae*. Supernatants were subsequently concentrated 10-fold using Microcon ultra centrifugal filter with a 10-kDa cutoff (Millipore, Billerica, Mass.).

PCR amplification of the *Ehrlichia* genes. Oligonucleotide primers for the amplification of the *E. chaffeensis* p120 and *E. canis* p140 gene fragments were designed manually, or by using PrimerSelect (Lasergene v5.08, DNAStar, Madison, Wis.) according to the sequences in GenBank (accession numbers U49426 and NC_007354, respectively) and synthesized (Sigma-Genosys, Woodlands, Tex.) (Table 1). Gene fragments corresponding to the N-termini (p120N/p140N), the C-termini (p120C/p140C), and the entire open reading frames (p120W/p140W) were amplified by PCR (FIG. 1A). Constructs containing the tandem repeat regions (designated p120TR and p140TR in this report, respectively) were described previously and used in this study (Yu et al., 1996; Yu et al., 2000). The *E. chaffeensis* p120TR contained only the first two tandem repeats (R1 and R2), whereas the p140TR contained the complete tandem repeat region (14 repeats) of the *E. canis* p140 (FIG. 1A).

PCR was performed with PCR HotMaster Mix (Eppendorf, Westbury, N.Y.) and the appropriate *Ehrlichia* genomic DNA as the template. The thermal cycling profile was: 95° C. for 3 min, 30 cycles of 94° C. for 30 s, annealing temperature (1° C. less than the lowest primer $T_m$) for 30 s, and 72° C. for the appropriate extension time (1 min/1000 base pairs) followed by a 72° C. extension for 10 min and a 4° C. hold.

Expression and purification of the recombinant *Ehrlichia* p120 and p140 proteins. The amplified PCR products were cloned directly into the pBAD/Thio-TOPO expression vector (Invitrogen, Carlsbad, Calif.) and transformed *E. coli* TOP10 cells (Invitrogen). The resulting transformants were screened by PCR for correctly oriented inserts, and plasmids from the positive transformants were isolated and sequenced to verify the inserts with an ABI Prism 377XL DNA sequencer (Applied Biosystems, Foster City, Calif.) at the University of Texas Medical Branch Protein Chemistry Core Laboratory.

Figure 5:
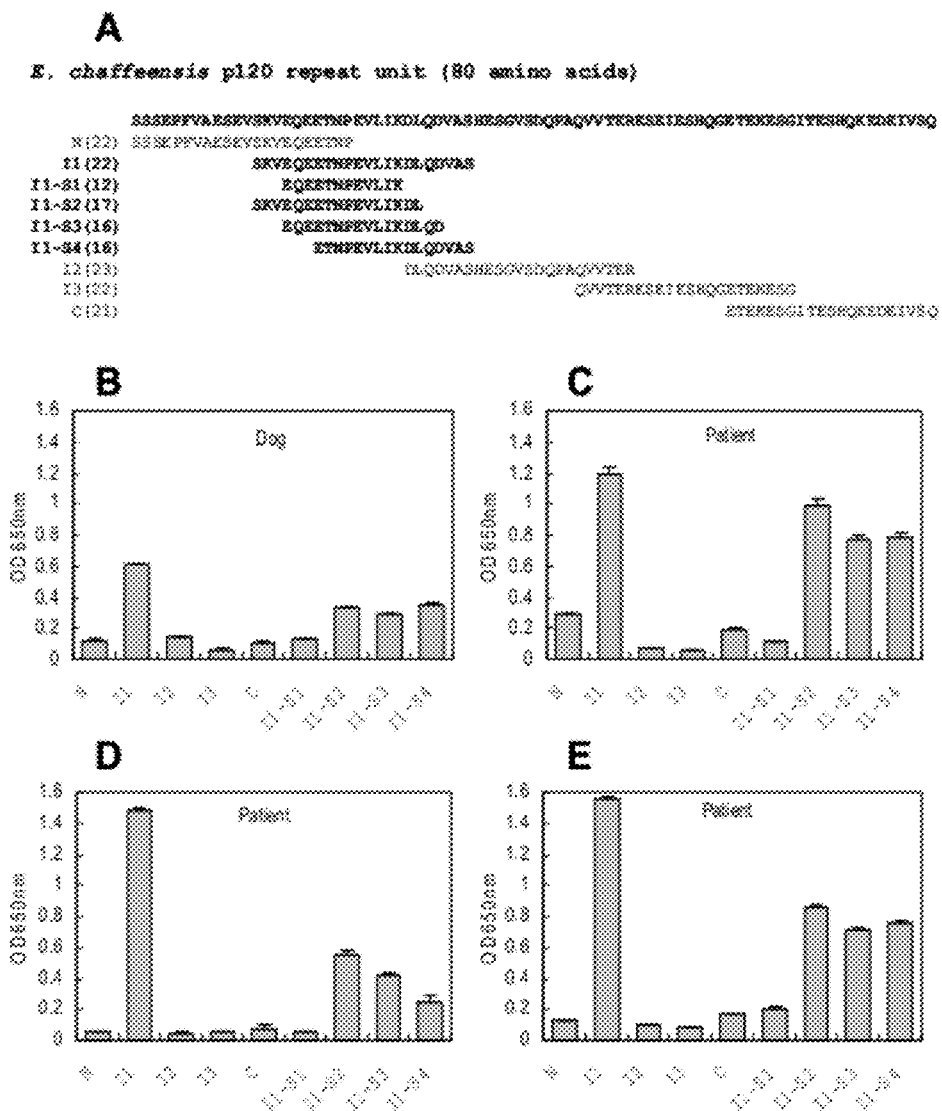
FIGS. 5A-5E. Immunoreactivity of overlapping synthetic peptides spanning the *E. chaffeensis* p120 repeat unit by ELISA.

Recombinant protein expression was performed for 4 h after induction with 0.2% arabinose, and proteins were purified under native conditions using HisSelect® columns (Sigma, St. Louis, Mo.). The recombinant TR regions of *Ehrlichia* p120 and p140 were expressed as glutathione S-transferase (GST) fusion proteins as previously described (Yu et al., 1996; Yu et al., 2000).

p120 and p140 synthetic peptides. For the *E. chaffeensis* p120, five overlapping peptides corresponding to a single repeat unit (p120R-N, p120R-I1, p120R-12, p120R-13, and p120R-C) were commercially synthesized (Bio-Synthesis, Lewisville, Tex.) (FIG. 1B, left panel; see FIG. 5A for sequences). Fine mapping within the p120R-I1 region was performed with four overlapping peptides (p120R-I1-S1, p120R-I1-S2, p120R-I1-S3, and p120R-I1-S4; Bio-Synthesis) (FIG. 1B, left panel; see FIG. 5A for sequences). For p140, six overlapping peptides (p120R-1 to p120R-6) corresponding to the different regions of the *E. canis* p140R were synthesized (Bio-Synthesis) (FIG. 1B, right panel; see FIG. 6A for sequences). All peptides were supplied as a lyophilized powder and resuspended in molecular biology grade water (1 mg/ml).

Antisera. Two convalescent anti-*E. chaffeensis* dog sera (nos. 2251 and 2495) and one convalescent anti-*E. canis* dog sera (no. 2995) were obtained from experimentally infected dogs. Sera from dogs exhibiting clinical signs or hematologic abnormalities consistent with CME were submitted to the Louisiana Veterinary Medical Diagnostic Laboratory from veterinarians statewide and screened by IFA, as described previously (McBride et al., 2001). HME patient sera were kind gifts from Focus Technologies (Cypress, Calif.) and William Nicholson at Centers for Disease Control and Prevention (Atlanta, Ga.). Rabbit anti-p120 and anti-p140 antisera were generated against the synthetic KLH-conjugated peptides located in the epitope-containing region of each respective repeat unit (p120: SKVEQEETNPEVLIKDLQD-VAS (SEQ ID NO:1); p140: EHSSSEVGEKVSKTSKEEST-PEVKA (SEQ ID NO:11)) by a commercial vendor (Bio-Synthesis).

Gel electrophoresis and Western immunoblotting. Purified *E. chaffeensis* or *E. canis* whole-cell lysates or recombinant proteins were separated by sodium dodecyl sulfate-polyacrylamide gel electrophoresis (SDS-PAGE) and transferred to nitrocellulose, and Western immunoblotting performed as previously described (McBride et al., 2003), except that primary dog sera were diluted 1:100, human sera were diluted 1:200, and rabbit antisera were diluted 1:1,000.

ELISA. Enzyme-linked immunosorbent assay (ELISA) plates (MaxiSorp; Nunc, Roskilde, Denmark) were coated (0.5 µg/well; 50 µl) with recombinant proteins or synthetic peptides suspended in phosphate-buffered saline (pH 7.4). Proteins and peptides were absorbed for 1 h at room temperature with gentle agitation, and subsequently washed thrice with 200 µl Tris-buffered saline containing 0.2% Tween 20 (TBST). Plates were blocked with 100 µl 10% equine serum (Sigma) in TBST for 1 h at room temperature with agitation, and washed. Convalescent dog or human sera diluted (1:100 or 1:200, respectively) in 10% equine serum-TBST were added to each well (50 µl) and incubated at room temperature for 1 h with gentle agitation. The plates were washed four times, and 50 µl alkaline phosphatase-labeled goat anti-dog or human IgG (H+L) secondary antibody (Kirkegaard & Perry Laboratories, Gaithersburg, Md.) diluted (1:5,000) in 10% equine serum-TBST was added and incubated for 1 h at room temperature. The plates were washed four times, and substrate (100 µl; BluePhos; Kirkegaard & Perry Laboratories) was added to each well. The plates were incubated in the dark for 30 min with agitation, and color development was determined on a microplate reader (VersaMax; Molecular Devices, Sunnyvale, Calif.) at $A_{650}$ and data analyzed by SoftmaxPro v4.0 (Molecular Devices). Optical density (OD) readings represent the mean OD for three wells (±standard deviations) after subtracting the OD value of the buffer-only wells. A reading >0.2 OD unit above the negative control absorbance was considered positive for all samples. In addition, a reading 0.2-0.5 OD unit above the control absorbance was considered a weak positive, and a reading >0.5 OD unit above the control absorbance was considered a strong positive.

Mass spectrometry. Sample solution or protein standard (1 µl) was spotted directly onto a MALDI target plate and allowed to air dry. Sinapic acid (Aldrich, Milwaukee, Wis.) matrix solution (1 µl; 50:50 acetonitrile/water) was then applied on the sample spot and allowed to dry. The dried MALDI spot was blown with compressed air (Decon Laboratories, King of Prussia, Pa.) before inserting into the mass spectrometer. Mass spectrometry was performed using a matrix-assisted laser desorption ionization-time-of-flight (MALDI-TOF) mass spectrometer (4800 MALDI TOF/TOF Proteomics Analyzer; Applied Biosystems) at the University of Texas Medical Branch Mass Spectrometry Core Laboratory. Data were acquired with the software package including 4000 series explorer (v3.6 RC1; Applied Biosystems). The instrument was operated in positive ion linear mode, mass range as required. 4000 laser shots were acquired and averaged from each sample shot. External calibration was performed using cytochrome C or BSA according to the target molecular weight.

TABLE 1

Oligonucleotide primers for amplification of the *E. chaffeensis* p120 and *E. canis* p140 gene fragments.

| Fragment | Name | Primers Sequence (5' to 3') | Amplicon size (bp) |
|---|---|---|---|
| p120 | p120N-F | ATGGATATTGATAATAGTAACATAAGTAC (SEQ ID NO: 16) | 1,644 |
| | p120C-R | TACAATATCATTTACTACATTGTGATT (SEQ ID NO: 17) | |
| p120N | p120N-F | ATGGATATTGATAATAGTAACATAAGTAC (SEQ ID NO: 18) | 162 |
| | p120N-R | TGTGTCATCTTCTTGCTCTTG (SEQ ID NO: 19) | |
| p120C | p120C-F | ATTCTAGTAGAAGATTTGCCATTAG (SEQ ID NO: 20) | 444 |
| | p120C-R | TACAATATCATTTACTACATTGTGATT (SEQ ID NO: 21) | |
| p140 | p140N-F | ATGGATATTGATAACAATAATGTGACTAC (SEQ ID NO: 22) | 2,064 |
| | p140C-R | TATTAAATCAACTGTTTCTTTGTTAGT (SEQ ID NO:23) | |
| p140N | p140N-F | ATGGATATTGATAACAATAATGTGACTAC (SEQ ID NO: 24) | 183 |
| | p140N-R | TGGATTTCCTACATTGTCATTC (SEQ ID NO: 25) | |
| p140C | p140C-F | GAAGTACAGCCTGTTGCAG (SEQ ID NO: 26) | 324 |

TABLE 1-continued

Oligonucleotide primers for amplification of the E. chaffeensis p120 and E. canis p140 gene fragments.

| Fragment | Name | Primers Sequence (5' to 3') | Amplicon size (bp) |
|---|---|---|---|
| | p140C-R | TATTAAATCAACTGTTTCTTTGTTAGT (SEQ ID NO:27) | |

Sequence analysis. Amino acid sequence alignments of *E. chaffeensis* p120 and *E. canis* p140 were performed with MegAlign (Lasergene v5.08; DNAStar). The major epitopes of p120 and p140 were examined for sequence similarity to other proteins by using the protein-protein basic local alignment search tool (BLAST; www.ncbi.nlm.nih.gov/BLAST).

Statistics. Statistical difference between experimental groups were assessed with the two-tailed Student's t-test, and significance was indicated by a P value of <0.05.

Results:

*E. chaffeensis* p120 and *E. canis* p140 composition and characteristics. In the *E. chaffeensis* (Arkansas strain) p120 and *E. canis* (Jake strain) p140 proteins, glutamate (17.5% in p120; 17.4% in p140), serine (12.2%; 15.8%), and valine (10.8%; 12.9%) were the most frequently occurring amino acids (Table 2). Moreover, in the TRs of p120 and p140, the occurrences of these three (E, S and V) residues were more frequent (22.3%/21.4%; 14.8%/18.5%; and 11.4%/13.3%, respectively). On the contrary, in the N- and C-termini of p120 and p140, the occurrences of these three residues became less frequent, except for the valine content in the C-terminus of p120. Due to the large proportion of glutamate residues, the p120 and p140 proteins were highly acidic (pI 3.8 and 3.9, respectively).

Amino acid sequence similarity within the N-terminus and surface-exposed motif of the repeat region between *E. chaffeensis* p120 and *E. canis* p140 has been reported (McBride et al., 2000; Yu et al., 2000), but sequence similarity within the C-terminus and the analysis of specific regions has not been fully explored. The amino acid identity was ~50% for the first 32 amino acids of the N-terminus. Similarly, homologous (~39% amino acid identity) regions were identified in the C-terminus of p120 and p140 (FIG. 2). A BLAST search determined no substantial sequence similarity with other known Ehrlichial proteins or proteins from organisms in closely related genera.

Figure 3:
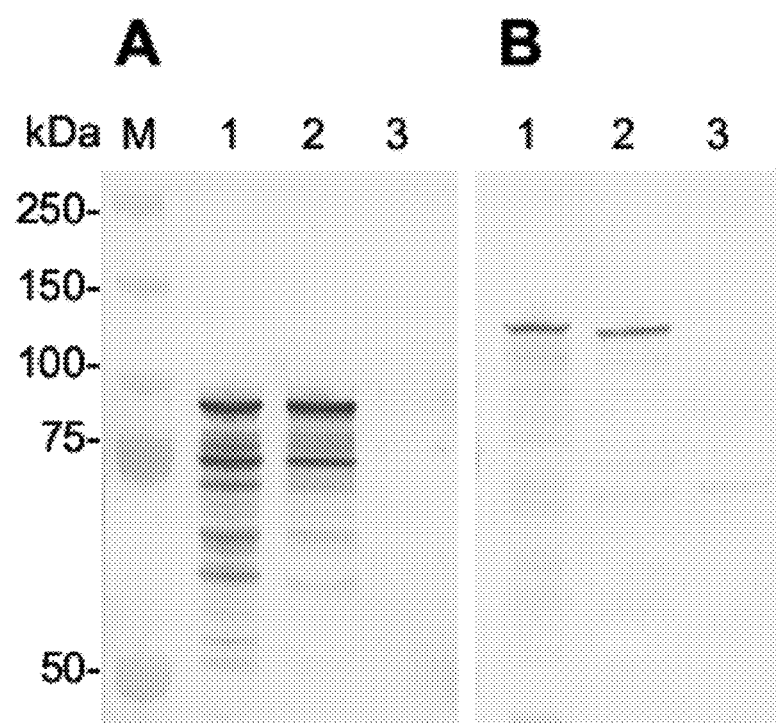
FIGS. 3A-3B. Identification of native *E. chaffeensis* p120 and *E. canis* p140 proteins by Western immunoblot.

Identification of the native *E. chaffeensis* p120 and *E. canis* p140 proteins. Western blotting identified two strongly reactive native proteins with the molecular mass of ~95 kDa and ~75 kDa (both larger than predicted mass of 61 kDa based on the amino acid sequence) and a few less prominent proteins (75-50 kDa) in *E. chaffeensis* whole-cell lysates and culture supernatants that reacted with monospecific rabbit antiserum against the synthetic p120R-I1 peptide; however, this antiserum did not react with any proteins in *E. canis* whole-cell lysates (FIG. 3A). Similarly, a native protein with the molecular mass of ~125 kDa (larger than predicted mass of 74 kDa) and a few smaller and less prominent proteins in *E. canis* whole-cell lysates reacted with monospecific rabbit antiserum against the p140TR. Proteins in *E. chaffeensis* whole-cell lysates did not react with this antiserum (FIG. 3B). Pre-immunization rabbit serum controls did not react with proteins in *E. chaffeensis* or *E. canis* whole-cell lysates by Western immunoblot.

TABLE 2

Predicted and observed molecular masses and amino acid analyses of *E. chaffeensis* p120 and *E. canis* p140 proteins.

| Protein | Molecular mass (kDa)[a] | | | Glutamate content | Serine content | Valine content |
|---|---|---|---|---|---|---|
| | Predicted | Observed | Mass[c] | n (%) | n (%) | n (%) |
| *E. chaffeensis* p120 | | | | | | |
| p120 | 77.1 | 110 | nd | 96 (17.5) | 67 (12.2) | 59 (10.8) |
| p120N | 22.3 | 23 | nd | 2 (4.0) | 4 (8.0) | 1 (2.0) |
| p120TR[b] | 47.0 | 58 | 47.1 | 78 (22.3) | 52 (14.8) | 40 (11.4) |
| p120C | 33.0 | 33 | nd | 16 (10.8) | 11 (7.4) | 18 (12.2) |
| Native p120 | 60.8 | 95/75 | nd | | | |
| *E. canis* p140 | | | | | | |
| p140 | 89.9 | 140 | nd | 120 (17.4) | 109 (15.8) | 89 (12.9) |
| p140N | 21.5 | 22 | nd | 4 (6.6) | 6 (9.8) | 7 (11.5) |
| p140TR | 85.6 | 130 | 85.9 | 111 (21.4) | 96 (18.5) | 69 (13.3) |
| p140C | 28.3 | 28 | nd | 5 (4.6) | 7 (6.5) | 13 (12.0) |
| Native p140 | 73.6 | 125 | nd | | | |

[a]Including the fusion tags: all were thioredoxin (16.3 kDa) except for p120TR and p140TR (GST tag; 28 kDa).
[b]Only first two repeats was cloned and expressed, but the amino acid content values are for the whole repeat region.
[c]As determined by MALDI-TOF mass spectrometry of the recombinant protein
nd = not determined Epitope mapping of *E. chaffeensis* p120 and *E. canis* p140 with recombinant proteins. To conclusively determine the major epitope-containing regions of p120 and p140, the recombinant full-length p120 and p140 proteins (p120W/p140W) and fragments corresponding to three distinct domains including the N-terminus (p120N/p140N), tandem repeat region (p120TR/p140TR), and C-terminus (p120C/p140C) were expressed (FIG. 1A). The p120W/p140W and p120TR/p140TR recombinant proteins exhibited molecular masses substantially larger than predicted by their amino acid sequences by SDS-PAGE. In contrast, the recombinant p120N/p140N and p120C/p140C exhibited masses consistent with that predicted by their amino acid sequences. MALDI-TOF mass spectrometry determined that the molecular masses of recombinant p120TR and p140TR proteins were nearly identical to that predicted by the corresponding amino acid sequences (Table 2), and thus the abnormal migration was not associated with posttranslational modifications.

Figure 4:
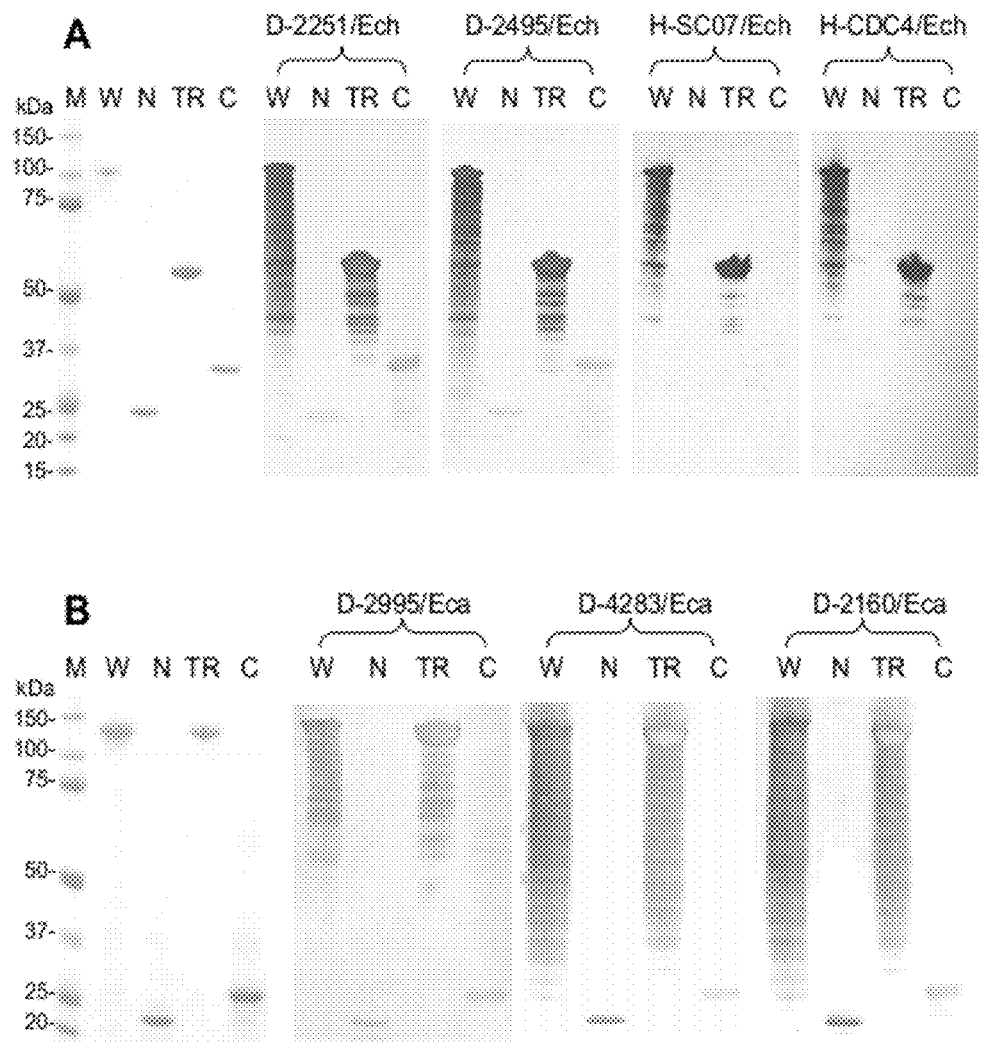
FIGS. 4A-4B. Immunoreactivity of recombinant proteins of *E. chaffeensis* p120 and *E. canis* p140 by Western immunoblot.

By Western immunoblot, the recombinant p120W and p120TR reacted very strongly with two anti-*E. chaffeensis* dog sera derived from dogs (nos. 2251 and 2495) experimentally infected with *E. chaffeensis* and two HME patient (nos. SC07 and CDC4) sera that had detectable *E. chaffeensis* antibodies by immunofluorescence assay (IFA); however, recombinant fragments of the p120N and p120C did not react, or reacted very weakly with those dog or patient sera, or reacted with only one serum (FIG. 4A). Similarly, the recombinant p140W protein and p140TR reacted very strongly with three anti-*E. canis* dog sera derived from an experimentally infected dog (no. 2995) and two naturally infected dogs (nos. 2160 and 4283); however, recombinant p140N and p140C did not react or reacted weakly with those dog sera (FIG. 4B). These human or dog sera did not recognize thioredoxin or GST proteins, and the normal human or dog sera did not recognize these recombinant proteins by Western immunoblot.

Peptide mapping of the major immunodeterminants of *E. chaffeensis* p120 and *E. canis* p140. To localize the major epitope(s) of *E. chaffeensis* p120 protein, 5 overlapping peptides (p120R-N, p120R-I1, p120R-I2, p120R-I3 and p120R-C) spanning the TR of p120 (FIG. 1B [left panel] and 5A) were reacted by ELISA with the anti-*E. chaffeensis* dog (no. 2251) sera and three HME patient (nos. 3, 18 and 20) sera that demonstrated *E. chaffeensis* antibodies by immunofluorescence assay (IFA). Four peptides (p120R-N, p120R-I2, p120R-I3 and p120R-C) were not immunoreactive, but p120R-I1 (22-mer) located in the N-terminal region of the TR reacted strongly with *E. chaffeensis* patient sera by ELISA (FIG. 5B to E). Furthermore, peptides p120R-N and p120R-I2, which contain amino acids (SKVEQEETNP (SEQ ID NO:12) and DLQDVAS (SEQ ID NO:13), respectively) present in the N- and C-termini of the p120R-I1 (22-mer), and the p120-S1 (EQEETNPEVLIK (SEQ ID NO:3)) representing a central overlapping region were not reactive with antibodies individually; however collectively the peptide p120-I1 (SKVEQEETNPEVLIKDLQDVAS (SEQ ID NO:1)) reacted strongly with antibodies in sera, suggesting that 22 amino acids were necessary for full constitution of the p120 TR epitope (FIG. 5A-E). Additional mapping with smaller peptides (p120R-I1-S1, S2, S3 and S4) demonstrated a significant (S1, S3 and S4, P<0.05 for all sera; S2, P<0.05 for all patient sera) contribution by both N-terminal (SKV) or C-terminal (DLQD) amino acids of peptide p120R-I1 and indicated that the continuous epitope was represented by this peptide (FIG. 5A-E).

To identify the peptide sequence containing the immunodeterminant in *E. canis* p140 protein, six overlapping peptides (designated p140R-1 to p140R-6 from N-terminus to C-terminus) spanning the TR of p140 (FIG. 1B [right panel] and 6A) were reacted with four anti-*E. canis* sera from naturally infected dogs (nos. 2160, 6, 10 and 18) (FIG. 6B to E). By ELISA, all overlapping peptides except for peptide p140R-3 (11-mer) reacted with anti-*E. canis* dog sera. Peptide p140R-4 (19 amino acids; SKEESTPEVKAEDLQ-PAVD (SEQ ID NO:2)), which was predicted to be surface-exposed and overlapped with the identified *E. chaffeensis* p120 epitope (see above and FIG. 2), had significantly (P≦0.05) stronger immunoreactivity with the majority of sera tested by ELISA. Additional peptide mapping with overlapping peptides (p140-R1) demonstrated that the N-terminal amino acids (SKEESTP (SEQ ID NO:14)) of p140-R4 did react with antibodies and contributed to the epitope as p140-R4 exhibited consistently stronger immunoreactivity than p140R-5, which lacked amino acids SKEES (SEQ ID NO:28) (FIG. 6A-E). Furthermore, peptide p140R-4, which contained additional C-terminal amino acids (EDLQPAVD (SEQ ID NO:15)) compared to p140R-3, exhibited strong immunoreactivity, whereas p140R-3 lacking these amino acids was virtually nonreactive, indicating a dominant contribution associated with these residues (EDLQPAVD (SEQ ID NO:15)) to the epitope. Comparative immunoreactivity between peptides p140R-2 and R-4 indicated that additional C-terminal amino acid residues, AVD, also contributed significantly (P<0.05) to epitope reactivity with half of the dog sera examined (FIG. 6A-E).

Figure 7:
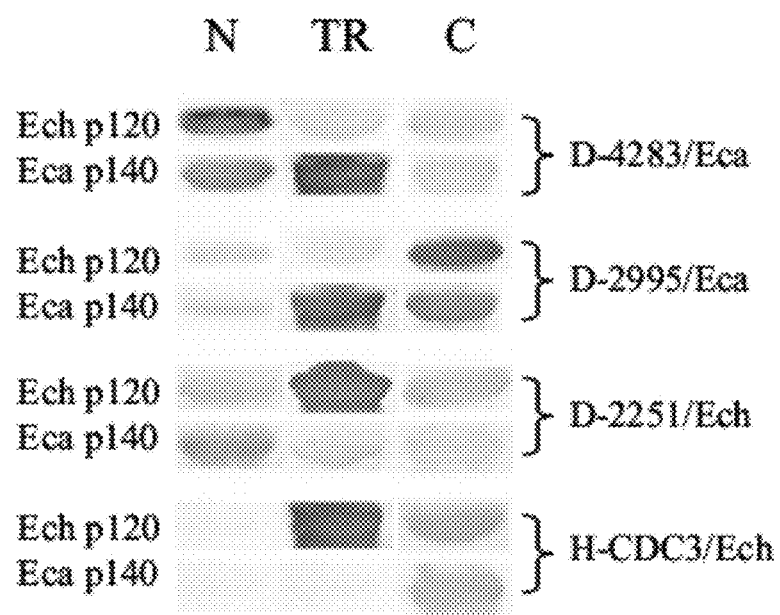
FIG. 7. Localization of minor cross-reactive epitopes between E. chaffeensis p120 and E. canis p140 proteins by Western immunoblot. E. chaffeensis p120 and E. canis p140 recombinant proteins (N-terminus [N], tandem repeats [TR], and C-terminus [C]) reacted with anti-E. canis sera (4283 and 2995 [D-4283/Eca and D-2995/Eca]) and anti-E. chaffeensis sera (2251 and CDC3 [D-2251/Ech and H-CDC3/Ech]).
Figure 8:
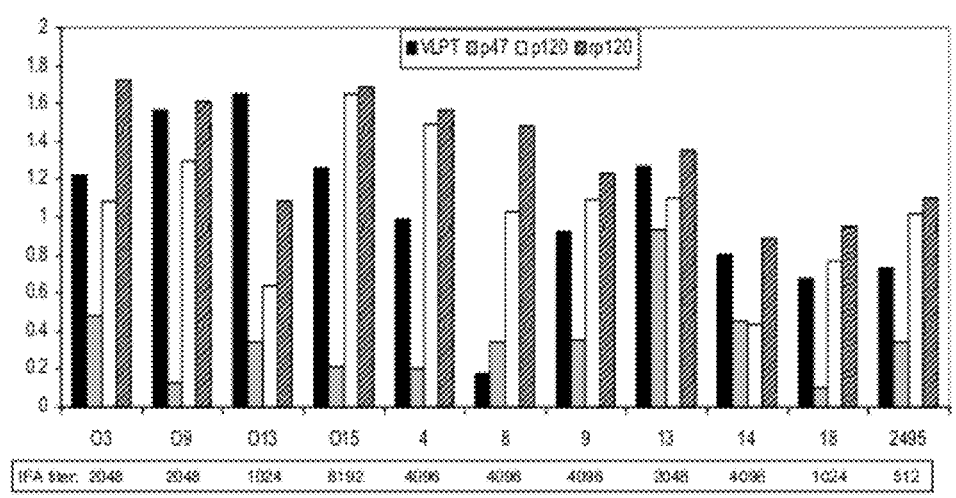
FIG. 8. Immunoreactivities of major antibody epitopes of E. chaffeensis immunodominant proteins with HME patient sera by ELISA. Synthetic epitope peptides of VLPT (R3+R4), p47 (N2C-N+R+C), p120 (R-I1), and the recombinant p120 TR protein (rp120, containing first two tandem repeats of p120) reacted with 10 HME patient sera and an anti-E. chaffeensis dog (no. 2495) serum. The OD readings represent the means for three wells (±standard deviations), with the OD of the negative control wells subtracted. The normal human or dog serum did not recognize these peptides.

Identification of immunoreactive regions for cross reaction between *E. chaffeensis* p120 and *E. canis* p140. To examine cross reactions between p120 and p140 and to localize the regions containing cross-reactive epitope(s), the recombinant p120 and p140 proteins corresponding to three distinct domains (N-terminus, TR region and C-terminus) were reacted with the anti-*E. canis* dog sera and anti-*E. chaffeensis* dog or patient sera. By Western immunoblot, the recombinant p120TR and p140TR proteins did not react, or reacted weakly with heterologous anti-*E. canis* sera and anti-*E. chaffeensis* sera, respectively; however, either recombinant N- or C-terminus of the p120 or p140 proteins did cross react with heterologous sera (FIG. 7).

Discussion:

It is well established that tandem repeat-containing proteins of *Ehrlichia* spp. are primary targets of the humoral immune response and elicit vigorous, and in many instances, species-specific antibodies (Doyle et al., 2006; Luo et al., 2008; McBride et al., 2000). *E. chaffeensis* p120 and *E. canis* p140 protein orthologs are well characterized major immunoreactive proteins strongly recognized by sera from HME patients and *E. canis*-infected dogs (McBride et al., 2000; Yu et al., 1997; Yu et al., 2000). Although previous studies demonstrated that *E. chaffeensis* p120 and *E. canis* p140 proteins reacted with antibodies in dog and/or patient sera (McBride et al., 2001; Yu et al., 1996; Yu et al., 1999; Yu et al., 2000), the immunologic properties of these two proteins were not fully defined, and the extent of the host response directed against them has remained undetermined.

All of the major immunoreactive TR proteins of *E. chaffeensis* and *E. canis* that have been characterized, including p120 and p140 orthologs, are highly acidic due to a predominance of glutamate/aspartate, moreover, they also appear to be serine-rich, which usually occurs more frequently within TRs of these proteins (Doyle et al., 2006; Luo et al., 2008; McBride et al., 2003; McBride et al., 2007; McBride et al., 2000). Interestingly, major continuous antibody epitopes of these proteins have been mapped to serine-rich acidic domains (Doyle et al., 2006; Luo et al., 2008; McBride et al., 2007; McBride et al., 2000; Nethery et al., 2007), which indicates a relationship between these domains and the host immune response; however, the specific role of these amino acids in directing the immune response against *Ehrlichia* is still unknown. The major epitope-containing regions of both *E. chaffeensis* p120 and *E. canis* p140 protein orthologs were mapped to the serine-rich tandem repeat units, which is consistent with the location of epitopes in other Ehrlichial TR-containing proteins. The antibody epitopes in p120TR and p140 TR, which exhibited the strongest antibody reactivity with both dog and human sera, were localized to the p120R-I1 (22 amino acids) and p140R-4 (19 amino acids) regions, respectively, which are homologous and predicted to be surface-exposed domains. Therefore, consistent with the location of epitopes mapped in other TR Ehrlichial proteins, the conserved surface-exposed domains of p120 and p140 TRs contained a dominant continuous immunodeterminant.

The length of the *E. chaffeensis* p120 and *E. canis* p140 epitopes was similar (~20 amino acids) and consistent in size with that described of other molecularly characterized continuous Ehrlichial epitopes, including those of VLPT/p19, p47/36, and p200 (*E. canis*) (Doyle et al., 2006; Luo et al., 2008; McBride et al., 2007; Nethery et al., 2007). Although smaller peptides associated with the mapped epitope reacted with antibodies, significantly higher antibody reactivity was observed with peptides consisting of ~20 amino acids a finding that is consistent with the epitope length the inventors have mapped on other TR proteins and similar in size to a neutralizing continuous antibody epitope consisting of 15 amino acids recently mapped in the *Helicobacter* UreB protein (Li et al., 2008). However, a smaller six amino acid continuous epitope has been mapped in *Anaplasma marginale* msp1a (Allred et al., 1990). Although major continuous epitopes have been mapped on several Ehrlichial TR proteins, one conformational epitope has been mapped in VLPT (Luo et al., 2008), and there may be other discontinuous epitopes associated with these major immunoreactive proteins that were not determined in this study. However, the host response to the continuous epitopes is strong and consistent with the response observed with recombinant folded proteins, suggesting the absence of dominant conformational epitopes.

Unlike other immunoreactive protein orthologs of *Ehrlichia*, the major epitopes of p120 and p140 exhibit some sequence similarity, raising the possibility that cross-reactive antibodies could be elicited; however, antibodies generated against epitope-containing peptides did not cross react by Western immunoblot, indicating that these epitopes appear to be primarily species-specific, a finding consistent with a previous study using antisera against recombinant p120TR and p140TR (McBride et al., 2000). Hence, the cross reactive immune response elicited by *Ehrlichia* species does not appear to be directed against the major continuous antibody epitopes identified thus far in *E. chaffeensis* and *E. canis* TR proteins, including the p120/p140. However, the inventors did identify that minor cross-reactive epitopes in the N- and C-terminal regions, which is consistent with the fact that substantial sequence similarity occurs in these regions. Therefore, as the inventors have proposed with major continuous epitopes identified in other Ehrlichial TR proteins, the p120/p140 TR epitopes could be utilized for species-specific diagnostic development.

The inventors have previously reported that some recombinant Ehrlichial immunoreactive proteins exhibited larger-than-predicted masses similar to their native counterparts by gel electrophoresis (Doyle et al., 2006; Luo et al., 2008; McBride et al., 2007; McBride et al., 2000), which was also observed in this study with both recombinant and native p120 and p140 proteins. The recombinant p120W/p140W and p120TR/p140TR exhibited abnormally large molecular masses, but the recombinant N- and C-terminal regions (p120N/p140N, p120C/p140C) migrated as expected, indicating that the highly acidic serine-rich TR was responsible for the anomalous electrophoretic behavior of these proteins. This abnormal electrophoretic migration was previously associated with detection of carbohydrate based on chemical reactivity, suggesting glycosylation of TRs (McBride et al., 2000).

In this study, the inventors determined by mass spectrometry that the molecular masses of p120TR and p140TR were consistent with those predicted by their amino acid sequences; therefore, the glycosylation is not responsible for the larger-than-predicted masses of the p120 and p140 proteins. It is likely that the high acidity of these proteins, particularly in the TR regions is responsible for the abnormal electrophoretic behavior. This is supported by studies demonstrating that highly acidic proteins exhibit abnormal migration patterns during gel electrophoresis (Garcia-Ortega et al., 2005; Graceffa et al., 1992). Like p120 and p140 proteins, the inventors recently reported that another major immunoreactive protein (VLPT) of *E. chaffeensis* also exhibited larger-than-predicted mass on gel, but mass spectrometry determined that this protein was not posttranslationally modified (Luo et al., 2008). The molecular masses of the native *E. chaffeensis* p120 (~95 kDa) and *E. canis* p140 (~125 kDa) proteins were smaller than previously reported masses (~120 kDa and ~140 kDa, respectively) (McBride et al., 2000; Yu et al., 2000). This difference is likely related to differences in SDS-PAGE procedures and accuracy of molecular mass markers. Nevertheless, the native proteins identified from the Ehrlichial lysate by the antibodies against synthetic epitope peptides, and the masses of the recombinant p120 or p140 protein (without fusion tag) were in agreement in this study.

The major immunoreactive proteins of *Ehrlichia* spp. have been identified and consist of a small subset of proteins. Three of these proteins in *E. chaffeensis* and *E. canis* are acidic, serine-rich and contain TRs (Doyle et al., 2006; Luo et al., 2008; McBride et al., 2007; Yu et al., 2000). The host immune response appears to be primarily directed at continuous species-specific epitopes within the TRs, which suggests similar characteristics contribute to immune response stimulation and production of species-specific antibodies directed at these TR epitopes. However, the role of continuous major antibody epitopes within Ehrlichial TR proteins in eliciting a protective immune response is currently undefined. Although protective antibody epitopes have been mapped to an *E. chaffeensis* major outer membrane protein, p28 (Li et al., 2002), new studies indicate that Ehrlichial TR proteins are secreted and interact with important host cell targets and facilitate pathogen survival (Wakeel et al., 2009). Thus, studies to examine whether host antibody response elicited by continuous epitopes in TR proteins such as the p120/p140 are protective, will provide much needed insight into the protective Ehrlichial antigens and effective immune responses.

SEQUENCES

| | | SEQ ID NO. |
|---|---|---|
| I1 (22) | SKVEQEETNPEVLIKDLQDVAS | 1 |
| I1-S1 (12) | EQEETNPEVLIK | 3 |
| I1-S2 (17) | SKVEQEETNPEVLIKDL | 4 |
| I1-S3 (16) | EQEETNPEVLIKDLQD | 5 |
| I1-S4 (16) | ETNPEVLIKDLQDVA | 6 |
| R-1 (19) | SSSEVGKKVSETSKEESTP | 7 |
| R-2 (19) | SETSKEESTPEVKAEDLQP | 8 |
| R-4 (19) | SKEESTPEVKAEDLQPAVD | 2 |
| R-5 (14) | TPEVKAEDLQPAVD | 9 |
| R-6 (19) | TPEVKAEDLQPAVDGSIEH | 10 |

Example 2 p120 Peptides Display Improved Sensitivity of Serodiagnosis of Human Monocytotropic Ehrlichiosis as Compared to the Full-Length p120 Protein or Combinations of *Ehrlichia* Peptides The sensitivities and specificities of synthetic peptides representing these and other well-defined major immunodeterminants of *E. chaffeensis* were determined by enzyme-linked immunosorbent assay (ELISA). Thirty-one human monocytotropic ehrlichiosis (HME) patient serum samples that had detectable *E. chaffeensis* antibodies (titers from 64 to 8,192) by indirect fluorescent antibody assay (IFA) were tested. All 31 serum samples reacted with at least one *E. chaffeensis* peptide, 30 (96.8%) with TRP120 peptides, 27 (87.1%) with TRP32 peptides, 24 (77.4%) with TRP47 peptides, 19 (61.3%) with Ank200 peptides, and 28 (90.3%) with recombinant TRP120-TR protein. A mixture of the two most sensitive peptides from TRP120 and TRP32 did not provide enhanced analytical sensitivity compared to that provided by TRP120 alone. These results demonstrate that the TRP120 peptide can be used for standardized sensitive point-of-care and reference laboratory immunodiagnostics for HME. This is the first study to compare analysis of molecularly defined major antibody epitopes with IFA for diagnosis of HME.

Also presented in this example is data mapping the major immunodeterminants of the *E. chaffeensis* 200-kDa ankyrin protein (Ank200) and the minor immunodeterminants in the N- and C-terminal regions of *E. chaffeensis* TRP47. Major antibody epitopes of Ank200 were localized to four polypeptide regions (18-mer, 20-mer, 20-mer, and 21-mer, respectively) in terminal acidic domains, which reacted with antibodies in sera from human monocytotropic ehrlichiosis (HME) patients and an *E. chaffeensis*-infected dog. Two minor epitope-containing regions were identified in the N terminus and the C terminus of TRP47.

Materials and Methods

Culture and purification of *E. chaffeensis*. *E. chaffeensis* (Arkansas strain) was propagated in DH82 cells and purified by size exclusion chromatography as previously described (McBride et al., 2001; Rikihisa et al., 1992). The fractions containing bacteria were frozen and utilized for DNA and antigen preparation (McBride et al., 1996).

PCR amplification of the *E. chaffeensis* genes. Oligonucleotide primers for the amplification of the *E. chaffeensis* Ank200 and TRP47 gene fragments were designed manually or by using PrimerSelect (Lasergene v5.08; DNAStar, Madison, Wis.) according to the sequences in GenBank (accession numbers YP_507490 and DQ085430, respectively) and synthesized (Sigma-Genosys, Woodlands, Tex.) (Table 3). Gene fragments corresponding to the different regions used for epitope mapping were amplified by PCR (FIG. 1 for Ank200; see FIG. 4A for TRP47). PCR was performed with PCR HotMaster mix (Eppendorf, Westbury, N.Y.) and *E. chaffeensis* genomic DNA as the template. The thermal cycling profile was as follows: 95° C. for 3 min, 30 cycles of 94° C. for 30 s, annealing temperature (1° C. less than the lowest primer melting temperature [Tm]) for 30 s, and 72° C. for the appropriate extension time (1 min/1,000 bp), followed by a 72° C. extension for 10 min and a 4° C. hold.

TABLE 3

Oligonucleotide primers for amplification of *E. chaffeensis* Ank200 and TRP47 gene fragments

| Fragment | Forward primer (5' to 3') | Reverse primer (5' to 3') | Size (bp) |
|---|---|---|---|
| Ank200 | | | |
| N | CAACAAAATCCTAATTCGCAAG (SEQ ID NO: 29) | CGATTTTATATCATTACCAGCA (SEQ ID NO: 30) | 1,644 |
| $N_1$ | CACCATGGCAGATCCAAAACAAG (SEQ ID NO: 31) | TACCGCATACAATGGATCTTC (SEQ ID NO: 32) | 384 |
| $N_2$ | CACCCCTTTACCTAAAGGTCAAAG (SEQ ID NO: 33) | ATCCCTAACACCTTCCC (SEQ ID NO: 34) | 456 |
| $N_3$ | CACCGCAGTTATTCATGATGAAGAG (SEQ ID NO: 35) | CAATGGGGATTGATTTC (SEQ ID NO: 36) | 468 |
| $N_4$ | CACCCATGTTATGGTTCAGAACC (SEQ ID NO: 37) | ATCATTACCAGCAACAGC (SEQ ID NO: 38) | 354 |
| $N_5$ | CACCATGGCAGATCCAAAACAAG (SEQ ID NO: 39) | TTGCTGAGAAGGCAAATC (SEQ ID NO: 40) | 195 |
| $N_6$ | CACCGAAACAGGAGAAACTGTAGAA (SEQ ID NO: 41) | TACCGCATACAATGGATCTTC (SEQ ID NO: 42) | 189 |
| $N_7$ | CACCGCAGTTATTCATGATGAAGAG (SEQ ID NO: 43) | AGCTAAATGCAGTAATGTCATTAC (SEQ ID NO: 44) | 246 |
| $N_8$ | CACCGTAATGACATTACTGCATTTAGCT (SEQ ID NO: 45) | CAATGGGGATTGATTTC (SEQ ID NO: 46) | 246 |
| $N_9$ | CACCGCAGTTATTCATGATGAAGAG (SEQ ID NO: 47) | AATTTCTTCTAGATCTGGCTC (SEQ ID NO: 48) | 123 |
| $N_{10}$ | CACCGAGCCAGATCTAGAAGAAATT (SEQ ID NO: 49) | AGCTAAATGCAGTAATGTCATTAC (SEQ ID NO: 50) | 144 |
| I | TGTTCAGTTAAAGGACGTGTTC (SEQ ID NO: 51) | AGCTAAATGCAGCGGTGTATC (SEQ ID NO: 52) | 1,371 |
| C | TTTGCTGAAAAGGGTGTAAAAA (SEQ ID NO: 53) | ATCTTCAGATGTAATAGGAGGTAGTCCC (SEQ ID NO: 54) | 1,368 |
| $C_1$ | TTTGCTGAAAAGGGTGTAAAAA (SEQ ID NO: 55) | TCCATGTAGACCATGAACTGC (SEQ ID NO: 56) | 822 |
| $C_2$ | GCAGTTCATGGTCTACATGGA (SEQ ID NO: 57) | TTTGCTCTGGCAAGAACTT (SEQ ID NO: 58) | 639 |
| $C_3$ | GCAGTTCATGGTCTACATGGA (SEQ ID NO: 59) | CGCTGATGCACCTAGAGA (SEQ ID NO: 60) | 318 |

TABLE 3-continued

Oligonucleotide primers for amplification of E. chaffeensis Ank200 and TRP47 gene fragments

| Fragment | Forward primer (5' to 3') | Reverse primer (5' to 3') | Size (bp) |
|---|---|---|---|
| $C_4$ | TCTCTAGGTGCATCAGCG (SEQ ID NO: 61) | TTTGCTCTGGCAAGAACTT (SEQ ID NO: 62) | 339 |
| $C_5$ | TCTCTAGGTGCATCAGCG (SEQ ID NO: 63) | ACCCTTATCAAATATTCCACT (SEQ ID NO: 64) | 171 |
| $C_6$ | AGTGGAATATTTGATAAGGGT (SEQ ID NO: 65) | TTTGCTCTGGCAAGAACTT (SEQ ID NO: 66) | 189 |
| TRP47 | | | |
| $N_1$ | ATGCTTCATTTAACAACAGAA (SEQ ID NO: 67) | ATGATAACCACGATCAGGTTC (SEQ ID NO: 68) | 135 |
| $N_2$ | GAACCTGATCGTGGTTATCAT (SEQ ID NO: 69) | AGGATCAACTAAGAAAGAAGC (SEQ ID NO: 70) | 135 |
| $N_3$ | GCTTCTTTCTTAGTTGATCCT (SEQ ID NO: 71) | ATGATCATGTTCATTGTGATG (SEQ ID NO: 72) | 132 |
| $N_4$ | CATCACAATGAACATGATCATG (SEQ ID NO: 73) | ATTTCCTTCAAGAACTGGAAC (SEQ ID NO: 74) | 132 |

$^a$Linker sequences for cloning are underlined.

Expression and purification of the recombinant proteins. The expression of the three largest E. chaffeensis Ank200 fragments (N, I, and C) was performed using the pUni/pR-SET-E Echo vector system (Invitrogen, Carlsbad, Calif.). Expression of the recombinant proteins in Escherichia coli BL21(DE3)pLysS (Invitrogen) was induced by adding 1 mM isopropyl-β-D-thiogalactopyranoside (IPTG) to cultures in log growth phase incubated for 4 h at 37° C. All other Ank200 fragments were expressed by pBAD/Thio-TOPO or pBAD102/D-TOPO vector (Invitrogen). Expression of the recombinant proteins in E. coli TOP10 (Invitrogen) was induced by adding 0.02% arabinose to 4 h cultures. All recombinant proteins were purified under native conditions using His-Select columns (Sigma, St. Louis, Mo.). The expression of the N-terminal region of E. chaffeensis TRP47 (TRP47-N) and the tandem repeat region of E. chaffeensis TRP120 (TRP120-TR; containing first two tandem repeats of TRP120 only) has been previously described (Doyle et al., 2006; Yu et al., 1996).

Synthetic peptides. For E. chaffeensis Ank200, six, four, and six overlapping peptides corresponding to three regions ($N_6$, $N_{10}$, and $C_6$) (see gray lines for locations in FIG. 1; see FIG. 3A to C, left, for sequences), respectively, were commercially synthesized (Bio-Synthesis, Lewisville, Tex.). For TRP47, the Cterminal peptide and three overlapping peptides corresponding to the N4 region (see FIGS. 4A and 5A) were synthesized (Bio-Synthesis). All other synthetic peptides (TRP120-R-$I_1$ [SKVEQEETNPEVLIKDLQDVAS (SEQ ID NO:1)], TRP47-R [ASVS EGDAVVNAVSQETPA (SEQ ID NO:75)], TRP32-$R_3$ [SDLHGSFSVELFD-PFKEAVQLGNDLQQSSD (SEQ ID NO:76)], TRP32-$R_4$ [SDSHEPSHLELPSLSEEVIQLESDLQQSSN (SEQ ID NO:77)], and E. canis TRP36-2R [TEDSVSAPATEDS-VSAPA (SEQ ID NO:78)], which contained two tandem repeat units of TRP36) used in this study have been described previously (Doyle et al., 2006; Luo et al., 2009; Luo et al., 2008). All peptides were supplied as a lyophilized powder and resuspended in molecular biology grade water (1 mg/ml). Antisera. A convalescent-phase anti-E. chaffeensis dog serum sample was obtained from an experimentally infected dog (no. 2251). HME patient serum samples were kind gifts from Focus Technologies (Cypress, Calif.) and the Centers for Disease Control and Prevention (Atlanta, Ga.). Patient serum samples positive for Rickettsia spp. but negative for E. chaffeensis by IFA were kind gifts from Arkansas Public Health Laboratory (Little Rock, Ark.). Rabbit anti-Ank200-$N_6$-1 antiserum was generated against the synthetic keyhole limpet hemocyanin-conjugated peptide Ank200-$N_6$-1 by a commercial vendor (Bio-Synthesis).

Gel electrophoresis and Western immunoblotting. Purified recombinant proteins were separated by sodium dodecyl sulfate-polyacrylamide gel electrophoresis (SDS-PAGE) and transferred to nitrocellulose, and Western immunoblotting was performed as previously described (McBride et al., 2003), except that primary dog sera were diluted 1:100, human sera were diluted 1:200, and rabbit antisera were diluted 1:1,000.

ELISA. For epitope mapping, an ELISA was performed as previously described (Luo et al., 2009). For serologic diagnosis evaluation, an Immobilizer amino plate (Nunc, Roskilde, Denmark) was used to increase the signal-to-noise ratio. Immobilizer amino plates were coated with synthetic peptides or recombinant proteins (0.5 μg/well; 50 μl) suspended in 100 mM sodium carbonate buffer (pH 9.6) and incubated with gentle agitation at room temperature for 1 to 2 h or overnight at 4° C. The wells were washed four times with 300 μl phosphatebuffered saline containing 0.05% (vol/vol) Tween 20 (PBST; pH 7.2) by a plate washer (SkanWasher 400; Molecular Devices, Sunnyvale, Calif.). Dog or human sera diluted (1:100 or 1:200, respectively) in PBST were added to each well (50 μl) and incubated at room temperature for 1 h. The plates were washed again, and 50 μl alkaline phosphatase-labeled goat anti-dog or -human IgG(H+L) secondary antibody (Kirkegaard & Perry Laboratories, Gaithersburg, Md.) diluted (1:5,000) in PBST was added and incubated at room temperature for 1 h. After the addition of substrate (BluePhos; Kirkegaard & Perry Laboratories), plates were incubated in the dark for 30 min, color development was determined on a microplate reader (VersaMax; Molecular Devices, Sunnyvale, Calif.) at $A_{650}$, and data were analyzed by SoftMax Pro version 4.0 (Molecular Devices). Optical density (OD) readings represent the mean OD value for three wells (±standard deviations) after subtracting the OD value of the negative control wells. All sera negative for E. chaffeensis by IFA had readings of <0.05 OD unit; therefore, a positive sample threshold was set at >0.1 OD unit. In addition, a reading of 0.1 to 0.5 OD unit was considered a weak positive, and a reading of >0.5 OD unit was considered a strong positive. IFA. The anti-*E. chaffeensis* antibody status in HME patient sera was determined as described previously (McBride et al., 2003). Antigen slides were prepared from DH82 cells infected with *E. chaffeensis* (Arkansas strain) (McBride et al., 2001). Sera were diluted 2-fold in PBS, starting at 1:64. Statistics. The statistical differences between experimental groups were assessed with the two-tailed Student t test, and significance was indicated by a P value of <0.05. Locus tag numbers of nucleotide sequences. *Ehrlichia* gene locus tag numbers for the proteins in this study were previously available in the Integrated Microbial Genomes system (img.jgi.doe.gov) (ECH_0170 for TRP32, ECH_0166 for TRP47, ECH_0039 for TRP120, ECH_0684 for Ank200, and Ecaj_0109 for TRP36).

Results

Figure 9:
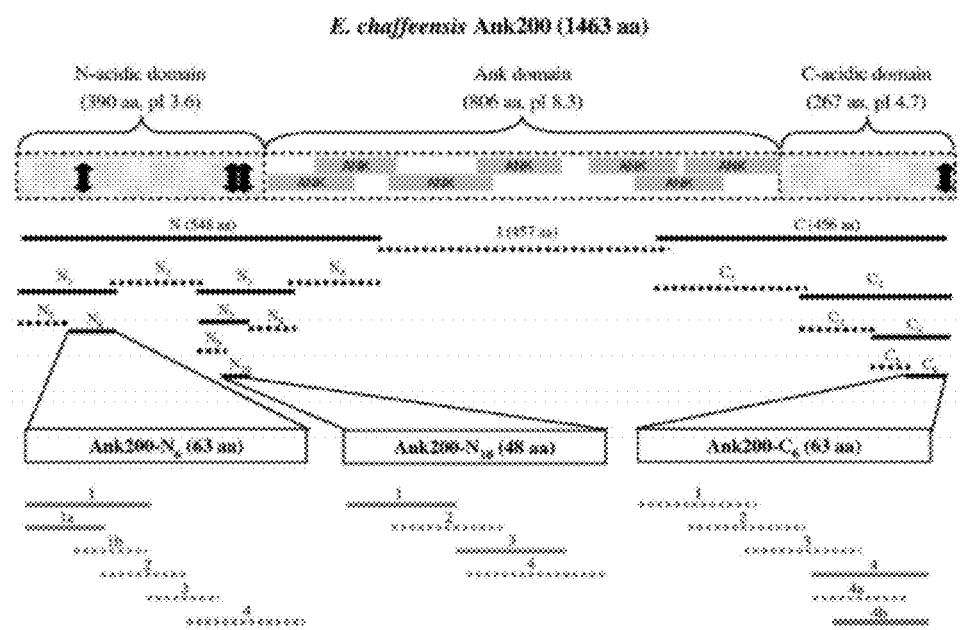
FIG. 9. Schematic of E. chaffeensis Ank200 protein, showing domains, predicted isoelectric points (pIs), and the recombinant proteins and synthetic peptides used for epitope mapping. Predicted ankyrin domains are shown in shaded boxes. The recombinant proteins and synthetic peptides are shown in black lines and gray lines, respectively, and solid lines show regions containing an epitope(s), whereas dashed lines show regions which did not react or reacted weakly with anti-E. chaffeensis human and dog sera. The approximate locations of mapped epitopes are designated by arrows.

*E. chaffeensis* Ank200 amino acid composition and domains. The overall Ank200 composition (1,463 amino acids [aa]) was dominated by three hydrophobic amino acids (L, V, and A; 353 aa), three polar amino acids (S, G, and N; 362 aa), and two strongly acidic amino acids (E and D; 198 aa), resulting in a protein with an acidic nature (pI 4.6). Like for *E. canis* Ank200, three specific domains (N acidic, Ank, and C acidic) were identified, according to amino acid composition and con served motifs (FIG. 9). The distal terminal polypeptides (N acidic, first 390 aa; C acidic, last 267 aa) exhibited a substantially larger proportion of strongly acidic amino acids (D and E; 22.6% in the N-acidic domain and 13.1% in the C-acidic domain) than the internal region (Ank domain, 806 aa [positions 391 to 1196]; 9.3% D and E) of the protein, where ankyrin repeats were located. In contrast, the Ank domain region contained more strongly basic amino acids (K and R; 10.2%) than strongly acidic amino acids. Consequently, the isoelectric points of two terminal domains were acidic (pI 3.6 and 4.7), whereas the internal Ank domain region was slightly basic (pI 8.3) (FIG. 9).

Immunoreactivities of the major *E. chaffeensis* Ank200 fragments. To determine the major epitope-containing regions of Ank200, the recombinant fragments corresponding to the N terminus (Ank200-N, aa 10 to 557), internal region (Ank200-I, aa 562 to 1018), and C terminus (Ank200-C, aa 984 to 1439), covering 98% of the open reading frame, were expressed (FIG. 9). By Western immunoblotting, the recombinant Ank200-N and Ank200-C (containing the N- and C-acidic domains, respectively) proteins reacted with an HME patient serum sample (no. SC07); however, recombinant protein of the Ank200-I (a majority of the Ank domain) did not react with the patient serum sample. A similar result was obtained by Western blotting probed with the anti-*E. chaffeensis* dog serum sample derived from a dog (no. 2251) experimentally infected with *E. chaffeensis*. Thus, the two immunoreactive fragments Ank200-N and Ank200-C were considered to contain antibody epitopes and were investigated further. The anti-*E. chaffeensis* patient or dog sera did not recognize thioredoxin protein, and the normal human or dog sera did not recognize these recombinant proteins by Western immunoblotting.

Major epitope-containing regions in Ank200-N. The major epitope-containing region(s) in Ank200-N was identified by evaluating the immunoreactivities of four overlapping recombinant proteins (N1 to N4) and of some smaller overlapping recombinant proteins (N5 to N10) (FIG. 1). Western immunoblotting revealed that N1 and N3 fragments were reactive with the patient serum samples, whereas two other fragments (N2 and N4) of Ank200-N were not reactive or only weakly reactive. Western blotting probed with anti-*E. chaffeensis* dog sera exhibited a similar result. Therefore, smaller overlapping recombinant proteins (N5, N6, N7, and N8) representing N1 and N3 regions were expressed, and two fragments, N6 and N7, were immunoreactive with the patient sera or anti-*E. chaffeensis* dog sera by Western blotting, while the other two fragments (N5 and N8) were not immunoreactive or were weakly immunoreactive. N7 was further divided into two overlapping polypeptides, N9 and N10, and polypeptide N10 was immunoreactive with the patient sera or anti-*E. chaffeensis* dog sera by Western blotting, while N9 was not immunoreactive. Thus, the N6 (63-aa) and N10 (48-aa) sections were identified as the major epitope-containing regions of *E. chaffeensis* Ank200-N, which were located in a highly acidic domain and exhibited high glutamate content (22.2% and 14.6%, respectively) (FIG. 9 and FIGS. 10A and B, left, for sequences).

Figure 10:
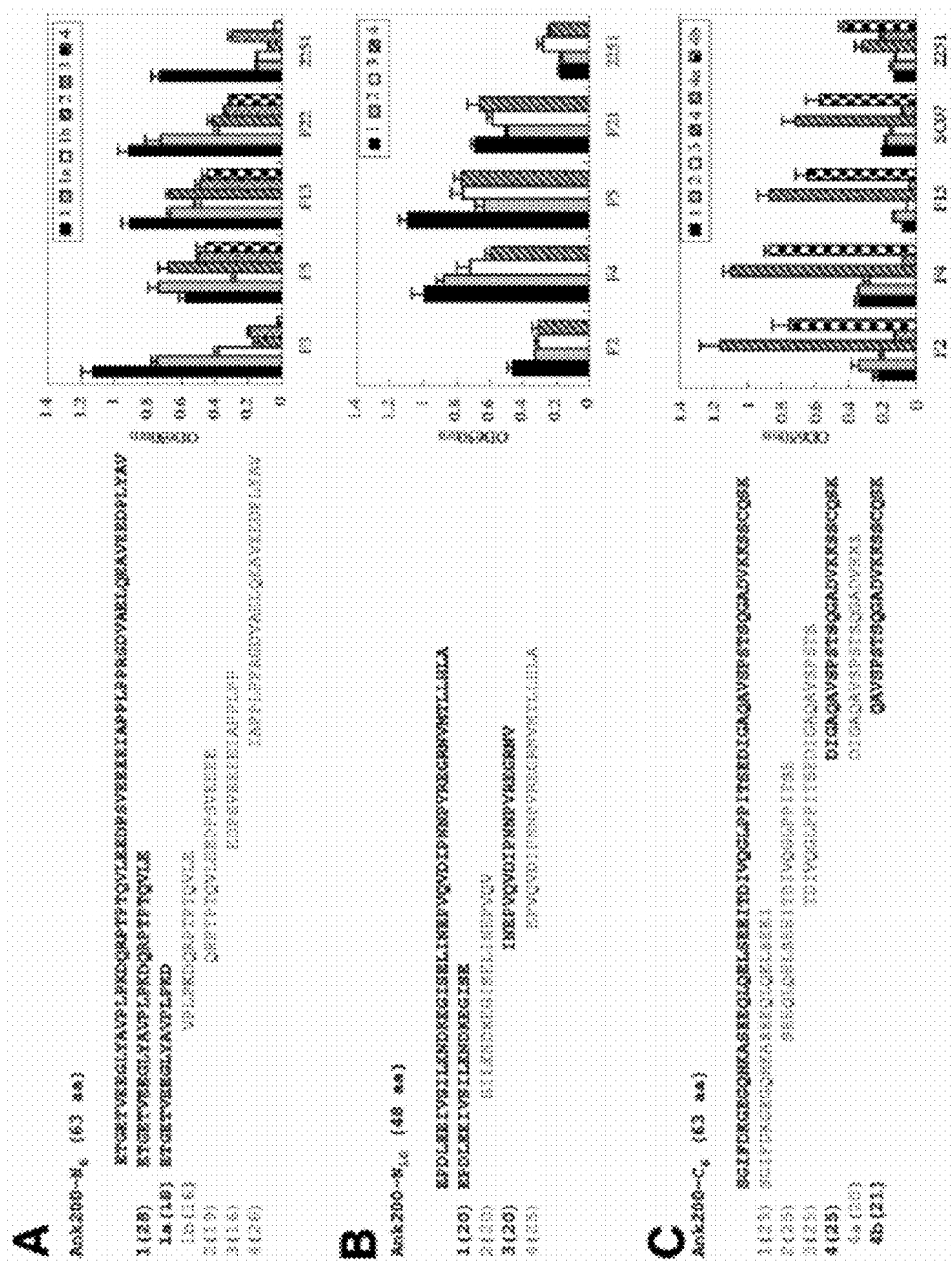
FIGS. 10A-C. Immunoreactivities of overlapping synthetic peptides spanning the E. chaffeensis Ank200-$N_6$, -$N_{10}$, and -$C_6$ fragments by ELISA.

Major epitope-containing region in Ank200-C. The major epitope(s) in Ank200-C was identified by evaluating the immunoreactivities of six overlapping recombinant proteins Ank200-C was divided into two overlapping fragments (C1 and C2), and Western immunoblotting revealed that the C2 fragment was immunoreactive with a patient serum sample, while C1 was not reactive. Therefore, C2 fragment was further divided into two overlapping polypeptides (C3 and C4), and the C4 fragment was immunoreactive with a patient serum sample by Western blotting, while C3 was not reactive or was only weakly reactive. Smaller overlapping polypeptides (C5 and C6) representing the C4 region were expressed, and the C6 fragment reacted with a patient serum sample by Western blotting, while C5 was not reactive or was weakly reactive. A similar result was obtained by Western blotting probed with an anti-*E. chaffeensis* dog serum sample. Thus, the C6 (63-aa) section of *E. chaffeensis* Ank200-C was identified as a major epitope-containing region, which was also located in a highly acidic domain and exhibited a high glutamate content (11.1%) (FIG. 9 and FIG. 10C, left, for the sequence).

Determination of the major immunodeterminants of *E. chaffeensis* Ank200 with synthetic peptides. Synthetic peptides were used to localize the major epitope(s) in three immunoreactive regions ($N_6$, $N_{10}$, and $C_6$) of Ank200, respectively. Four synthetic overlapping polypeptides ($N_6$-1, 2, 3, and 4; FIG. 10A, left panel) covering the sequence of Ank200-$N_6$ (63 aa) were generated and reacted by ELISA with an anti-*E. chaffeensis* dog serum (no. 2251) and four HME patient sera (nos. F3, F5, F13 and F22) that had detectable *E. chaffeensis* antibodies by IFA. Among five sera, peptide $N_6$-2 did not react with two sera, reacted weakly with one and strongly with two sera; peptide $N_6$-3 did not react with one sera and reacted weakly with four sera; peptide $N_6$-4 did not react with two sera and reacted weakly with three sera; however, peptide $N_6$-1 was found to react strongly with all the anti-*E. chaffeensis* dog and patient sera, indicating that the N-terminal fragment (28 aa) of the Ank200-$N_6$ region had a significantly (P<0.05 for dog serum and most patient sera) stronger immunoreactivity than other fragments and contained a major antibody epitope (FIG. 10A, right panel). To further determine the amino acid sequence reactive with antibody, $N_6$-1 was divided into two smaller overlapping peptides ($N_6$-1a and $N_6$-1b). By ELISA, peptide $N_6$-1b did not react with the anti-*E. chaffeensis* dog serum and reacted weakly with four patient sera; however, although peptide $N_6$-1a was also not reactive with antibodies in dog serum, it reacted strongly with all four patient sera, indicating that the N-terminal amino acids (ETGETVEEGLYA (SEQ ID NO:79)) contributed significantly (P<0.05) to epitope reactivity with all patient sera (FIG. 10A, right panel). Therefore, $N_6$-1a (18 aa; ETGETVEEGLYAVPLPKD (SEQ ID NO:80)) contained a major continuous antibody epitope of Ank200 for human, but longer sequence of peptide $N_6$-1 (28 aa; ETGETVEEG-LYAVPLPKDQRPTPTQVLE (SEQ ID NO:81)) exhibited the strongest immunoreactivity and was necessary for full reconstitution of the major antibody epitope of Ank200.

To identify the peptide sequence containing the immunodeterminant in Ank200-$N_{10}$ (48 aa) region, four overlapping peptides ($N_{10}$-1, 2, 3 and 4; FIG. 10B, left panel) covering $N_{10}$ region were reacted with an anti-*E. chaffeensis* dog serum (no. 2251) and four HME patient sera (nos. F2, F4, F5 and F21). By ELISA, peptides $N_{10}$-1 and 2 did not react and peptides $N_{10}$-3 and 4 reacted weakly with antibodies in the dog serum (FIG. 10B, right panel). Since the recombinant Ank200-$N_{10}$ protein reacted strongly with anti-*E. chaffeensis* dog serum by Western blotting, the data suggested that the sequence longer than above peptides was required to reconstitute the major antibody epitope of Ank200 recognized by antibodies in the dog serum. By ELISA, peptide $N_{10}$-2 reacted weakly with two patient sera and reacted strongly with two patient sera, and peptides $N_{10}$-1, 3 and 4 reacted weakly with one patient serum but reacted strongly with other three patient sera, suggesting that $N_{10}$ had two epitope-containing regions for human, $N_{10}$-1 (20 aa; EPDLEEIVSILKNDKEGISE (SEQ ID NO:82)) and $N_{10}$-3 (20 aa; INEPVQVDIPNNPVREGRNV (SEQ ID NO:83)), and the C-terminal amino acids (MTLLHLA (SEQ ID NO:84)) of $N_{10}$ had no substantial contribution to the epitope reactivity; moreover, peptide $N_{10}$-1 exhibited substantially stronger immunoreactivity than did peptides $N_{10}$-3 with three patient sera (FIG. 10B, right panel).

Four synthetic overlapping peptides ($C_6$-1, 2, 3 and 4; FIG. 10C, left panel) covering the sequence of Ank200-$C_6$ (63 aa) were reacted by ELISA with an anti-*E. chaffeensis* dog serum (no. 2251) and four HME patient sera (nos. F2, F4, F15 and SC07). Peptides $C_6$-1, 2 and 3 were only weakly immunoreactive with one or two patient sera, but peptide $C_6$-4 was found to react with the anti-*E. chaffeensis* dog serum and react strongly with all patient sera, indicating that the C-terminal fragment (25 aa) of the Ank200 contained a major antibody epitope and the C-terminal sequence (QGADVKKSSCQSK (SEQ ID NO:85), 13 aa) significantly ($P<0.05$ for all sera) contributed to the epitope reactivity (FIG. 10C). To further determine the amino acid sequence reactive with antibody, two smaller overlapping peptides ($C_6$-4a and 4b) representing fragment $C_6$-4 reacted with anti-*E. chaffeensis* dog and patient sera by ELISA. The peptide $C_6$-4a was not immunoreactive with all sera, however, peptide $C_6$-4b was found to react with the anti-*E. chaffeensis* dog serum and react strongly with all patient sera, indicating that the very distal C-terminal fragment $C_6$-4b (21 aa; QAVSPSTSQGADVKKSSCQSK (SEQ ID NO:86)) contained a major continuous antibody epitope of Ank200. Moreover, the very distal C-terminal amino acids (SCQSK (SEQ ID NO:87)) contributed significantly ($P<0.05$ for all sera) to the epitope immunoreactivity (FIG. 10C).

Figure 11:
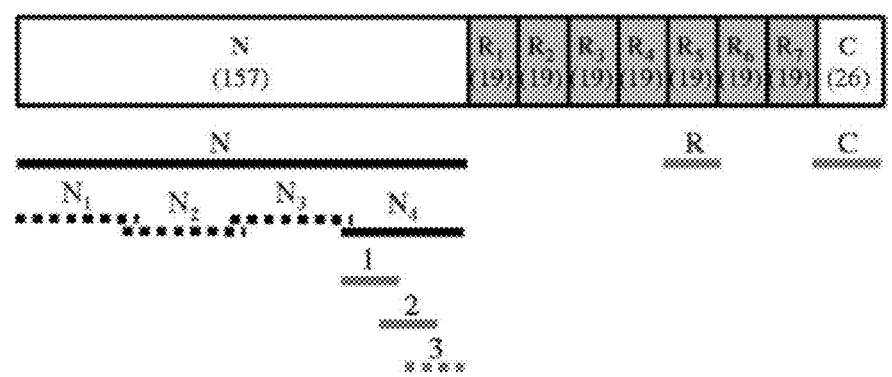
FIG. 11. Schematic of TRP47 showing domains, location of TRs (number of amino acids in parentheses), and recombinant proteins and synthetic peptides used for epitope mapping. The recombinant proteins and synthetic peptides are shown in black lines and gray lines, respectively, and solid lines show regions containing epitope(s).

Identification of TRP47 antibody epitopes in the TR flanking terminal regions. *E. chaffeensis* TRP47 has N-(157 aa) and short C-(26 aa) termini flanking the TR (19 aa each) region (FIG. 11). In a previous study, it was determined that the TR of TRP47 contained a major antibody epitope (Doyle et al., 2006); however the N- and C-terminal regions were not fully explored. The immunoreactivity of TRP47-N and TRP47-C regions was further investigated using HME patient sera in this report. A large panel of 31 patient sera that had detectable *E. chaffeensis* antibodies by IFA was used to detect the recombinant TRP47-N protein by Western blot; as a result, 13 of 31 sera reacted with TRP47-N, indicating that the N-terminal region of TRP47 contained a minor antibody epitope.

To locate the epitope in the TRP47-N, four recombinant overlapping proteins (TRP47-$N_1$, $N_2$, $N_3$, and $N_4$; FIG. 11) covering the sequence of whole TRP47-N region were expressed and reacted with three HME patient sera (nos. O13, O15 and 19) that recognized TRP47-N by Western blotting. The recombinant $N_2$ fragment did not react with the patient sera, the $N_1$ reacted weakly with one patient serum, the $N_3$ reacted with two sera (one weakly), while the $N_4$ fragment reacted with all three sera strongly, indicating the TRP47-$N_4$ fragment (44 aa) contained a minor antibody epitope. Three synthetic overlapping polypeptides ($N_4$-1, 2, and 3; FIG. 11 and FIG. 12A) covering the sequence of TRP47-$N_4$ were generated and reacted with six HME patient sera (nos. O15, 6, 9, 13, 18 and 19) that recognized TRP47-N by Western blotting. By ELISA, peptide $N_4$-3 was not reactive with any tested serum, $N_4$-1 was found to react with five sera (except for no. 19), and $N_4$-2 reacted with three sera (nos. 6, 18 and 19), and the reaction with serum no. 19 was very strong (FIG. 12B). Therefore, the assembled sequence (33 aa) of $N_4$-1 and 2 fragments contained the antibody epitope with the TRP47-N region.

Although the TR of TRP47 has previously been reported to react with anti-*E. chaffeensis* dog serum, its immunoreactivity with the HME patient serum has not been reported. Synthesized TR unit (TRP47-R; 19 aa) and C-terminus (TRP47-C; 26 aa) of TRP47 (FIG. 11 and FIG. 12A) were reacted by ELISA with sera from seven HME patients and one experimentally infected dog. Peptide TRP47-R was recognized by six patient sera and the dog serum; peptide TRP47-C was recognized by three patient sera, but exhibited significantly ($P<0.05$) stronger reactivity than did TRP47-R with two sera (nos. O3 and 13) (FIG. 12C). Hence, both TRP47-R and TRP47-C exhibited the immunoreactivity with HME patient sera; however, TRP47-R had stronger overall immunoreactivity ($P<0.05$ for most sera) than TRP47-C. Moreover, TRP47-R exhibited stronger immunoreactivity than did TRP47-C with an anti-*E. chaffeensis* dog serum.

Evaluation of synthetic *E. chaffeensis* major immunodeterminants for serologic diagnosis of HME. In order to examine and compare the immunoreactivity of *E. chaffeensis* major immunoreactive epitopes that have been characterized, a panel of 31 HME patient sera that had detectable *E. chaffeensis* antibodies by IFA (titer from 64 to 8192) were used to examine and compare the sensitivity of synthetic epitopes from *E. chaffeensis* TRP32, TRP47, TRP120 and Ank200 with IFA. Epitopes for TRP32, TRP47, and TRP120 mapped in other studies were also included in this evaluation. An equal (w:w) mixture of TRP32-$R_3$ (30 aa) and -$R_4$ (30 aa) peptides were used for TRP32, an equal mixture of TRP47-$N_4$-1 (22 aa), -R (19 aa) and -C (26 aa) peptides was used for TRP47, TRP120-R-$I_1$ (22 aa) peptide was used for TRP120, and an equal mixture of Ank200-$N_6$-1a (18 aa), $N_{10}$-1 (20 aa), and $C_6$-4b (21 aa) were used for Ank200. In addition, a recombinant TRP120 TR protein (rTRP120-TR) and an equal mixture of TRP32-$R_3$, TRP32-$R_4$ and TRP120-R-$I_1$ peptides were also tested. *E. canis* TRP36-2R (18 aa) was used as a negative control peptide. Patient sera (n=10) negative for *E. chaffeensis* antibodies by IFA were also tested.

Figure 13A:
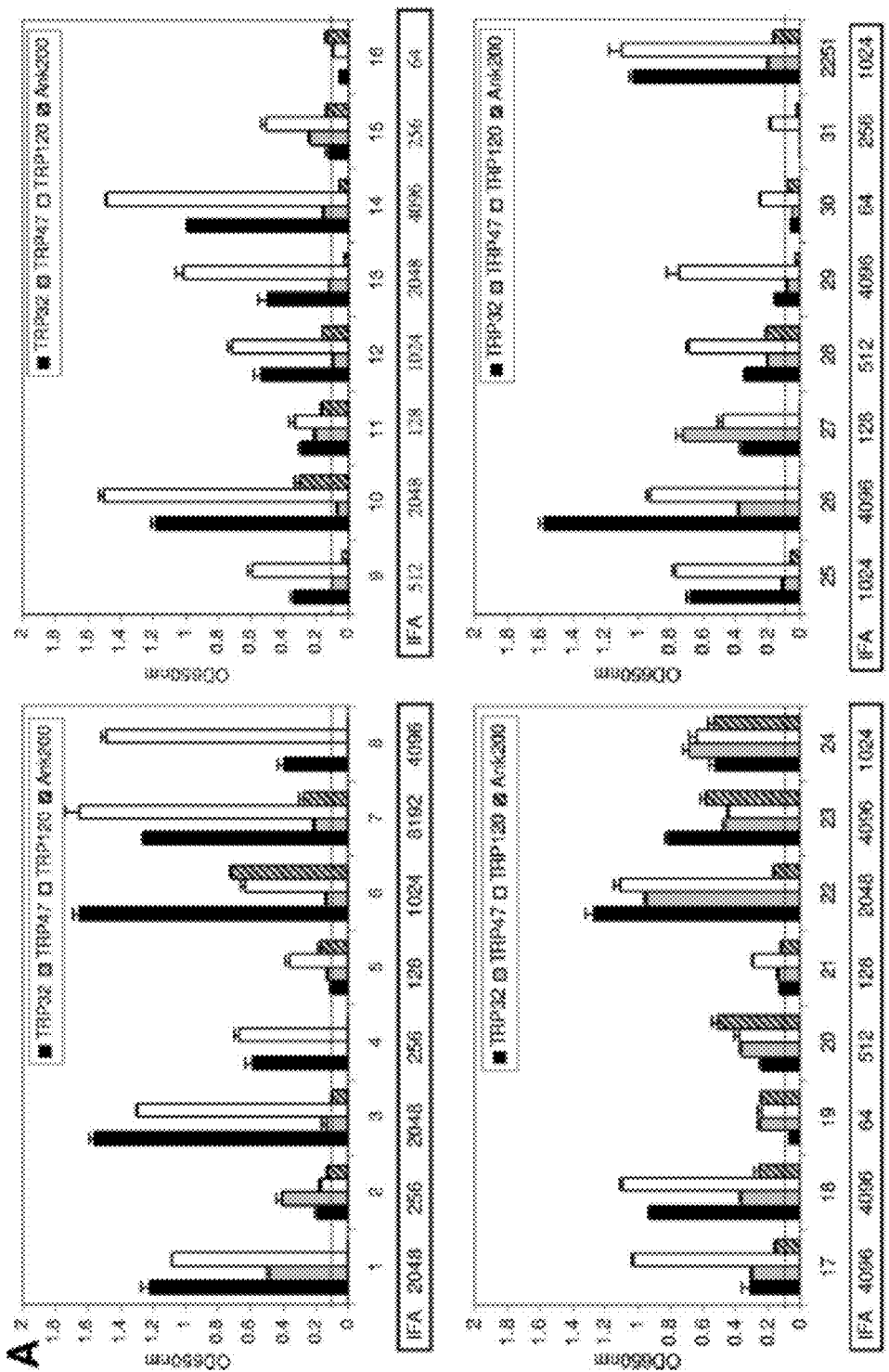
FIGS. 13A-B. Immunoreactivity of major antibody epitopes from E. chaffeensis immunoreactive proteins with HME patient sera by ELISA.
Figure 13B:
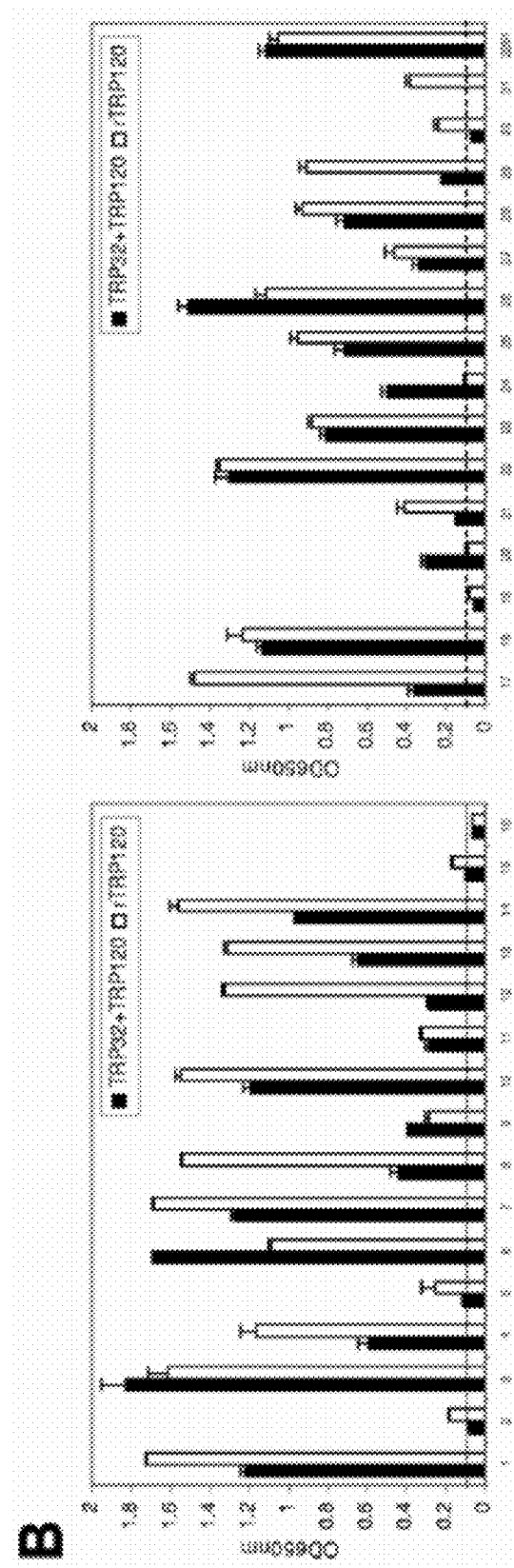

All 31 HME patient sera reacted with at least one *E. chaffeensis* peptide and 30 sera (96.8%) reacted with TRP120 peptide, 27 (87.1%) with TRP32 peptides, 24 (77.4%) with TRP47 peptides, 19 (61.3%) with Ank200 peptides (FIG. 13A; Table 4). Only one serum (no. 16) with low IFA titer (1:64) did not reach established positive cutoff with TRP120 peptide, and four sera (nos. 16, 19, 30 and 31) with low IFA titer (three with 1:64 and one with 1:256) did not react with TRP32 peptides. The recombinant TRP120-TR protein was recognized by 28 (90.3%) sera, and a mixture of TRP120 and TRP32 peptides was recognized by only 26 (83.9%) sera and did not provide enhanced sensitivity over the TRP120 alone (FIG. 13B; Table 4). These results suggested that TRP120 is the best candidate for immunodiagnosis of HME, and a single synthetic peptide TRP120-R-I$_1$ from TRP120 repeats exhibited higher sensitivity than the peptide mixture or recombinant TRP120-TR protein did with HME patient sera. Moreover, the peptides were not recognized by patient sera that were positive for *Rickettsia* spp. but not positive for *E. chaffeensis* by IFA, indicating that ELISA reactions between synthetic *E. chaffeensis* immunodeterminants and HME patient sera were specific.

TABLE 4

Analytical sensitivity of synthetic antibody epitopes of *E. chaffeensis* immunoreactive proteins for immunodiagnosis of HME by ELISA.

| Antigens | TRP32 | TRP47 | TRP120 | Ank200 | TRP32 + TRP120 | Overall | rTRP120 |
|---|---|---|---|---|---|---|---|
| No. of patients with detectable antibodies | 27 | 24 | 30 | 19 | 26 | 31 | 28 |
| % of patients with detectable antibodies | 87.1 | 77.4 | 96.8 | 61.3 | 83.9 | 100 | 90.3 |

$^a$ Synthetic epitope peptides of TRP32 (R$_3$ + R$_4$), TRP47 (N$_4$ − 1 + R + C), TRP120 (R − I$_1$) and Ank200 (N$_6$ − 1a + N$_{10}$ − 1 + C$_6$ − 4b), and an equal mixture of TRP32 − R$_3$, TRP32 − R$_4$ and TRP120-R − I$_1$ peptides as well as the rTRP120 (recombinant TRP120-TR protein, containing first two tandem repeats of TRP120 only) reacted with 31 HME patient sera. "Overall" refers to overall number and percentage of patients with detectable antibodies against any tested synthetic peptide.
$^b$ A sample with a reading 0.1 OD unit above the negative control absorbance was considered positive.

Discussion

Many of the major immunoreactive proteins of *E. chaffeensis* and *E. canis* have been identified and molecularly characterized, and interestingly, most are members of a small group of tandem repeat or ankyrin repeat containing proteins, including TRP32/TRP19, TRP47/TRP36, TRP120/TRP140 and Ank200s (Doyle et al., 2006; McBride et al., 2003; McBride et al., 2007; Sumner et al., 1999; Yu et al., 1997; Yu et al., 2000). Common features among these proteins include serine-rich TRs and an acidic pI (due to a predominance of glutamate/aspartate). Both recombinant and native proteins exhibit electrophoretic masses larger than predicted by amino acid sequence, due to the acidic properties of the proteins and not by the addition of glycans post-translationally (Garcia-Ortega et al., 2005; Luo et al., 2009; Luo et al., 2008). Notably, major continuous antibody epitopes of these proteins have been mapped to acidic domains, which are located in the central TR region in all TRPs or N- and C-terminal regions in *E. canis* Ank200, indicating Ehrlichial acidic domains, particularly those in TRs, are primary targets of the host humoral immune response (Doyle et al., 2006; Luo et al., 2009; Luo et al., 2008; McBride et al., 2003; McBride et al., 2007; Nethery et al., 2007). The association of these acidic domains with the host immune response is interesting and unique and to the inventor's knowledge, has not been described with respect to any other pathogen; however, the specific role of these domains in Ehrlichial pathobiology or immunity is still unknown.

*E. chaffeensis* and *E. canis* Ank200 protein orthologs are the largest Ehrlichial major immunoreactive proteins. They have identical chromosomal locations, and exhibit ~50% nucleic acid identity and ~32% amino acid identity, and they lack serine-rich TRs present in other Ehrlichial major immunoreactive proteins (McBride et al., 2003). However, they have similar distal N- and C-terminal acidic domains flanking the centralized ankyrin domain containing numerous ankyrin repeats that may mediate protein-protein interactions (Nethery et al., 2007). Like the ankyrin protein AnkA from *Anaplasma phagocytophilum* (Park et al., 2004), *E. chaffeensis* Ank200 is also translocated to the nucleus of infected cells, where it interacts with the DNA motif Alu (Zhu et al., 2009). In this study, major epitope-containing regions of *E. chaffeensis* Ank200 were mapped to the distal N- and C-terminal acidic (pI 3.6 and 4.7) domains, which is consistent with the location of the four epitopes mapped in *E. canis* Ank200 N- and C-terminal acidic (pI 4 and 4.9) domains (Nethery et al., 2007). The antibody epitopes in *E. chaffeensis* Ank200, which exhibited the strongest antibody reactivity with both dog and human sera, were localized to four polypeptides $N_6$-1a, $N_{10}$-1, $N_{10}$-3 and $C_6$-4b (18-mer, 20-mer, 20-mer, and 21-mer, respectively), with three in the N-terminal domain and only one in the C-terminal domain, demonstrating that the N-terminal domain has multiple epitopes, and thus, is the immunodominant region. The length of the Ank200 epitopes was similar and consistent in size (around 20-mer) with those described of other molecularly characterized continuous Ehrlichial epitopes Doyle et al., 2006; Luo et al., 2009; Luo et al., 2008; McBride et al., 2007; Nethery et al., 2007. However, a smaller six-amino acid epitope has been reported *Anaplasma marginale* msp1a protein (Allred et al., 1990). One conformational epitope has been mapped in TRP32-R$_4$ (Luo et al., 2008), and there may be other conformational epitopes associated with these major immunoreactive proteins that were not determined, although the host response to the continuous major epitopes in Ehrlichial immunodominant proteins is strong and suggest the absence of dominant conformational epitopes.

A major epitope in the TR region of the TRP47 and corresponding ortholog (TRP36) in *E. canis* was previously reported (Doyle et al., 2006). However, a comprehensive analysis of the regions flanking the TR was not performed. Hence, in this Example, HME patient sera were used to fully explore these regions and all three regions exhibited the immunoreactivity with patient sera. Two additional epitope-containing regions were identified in the N- and C-termini of TRP47, respectively, but TRP47-TR exhibited the stronger overall immunoreactivity than TRP47-N and -C and was more consistently recognized by antibodies in HME patient sera. Therefore, TRP47 TR appears to be the major antibody epitope and minor epitopes are located in the N- and C-termini. Similarly, minor cross-reactive antibody epitopes have been identified in N- and C-terminal regions of the TRP120 and TRP140 (Luo et al., 2009). Some HME patients only developed antibodies to one or more of the TRP47 minor epitopes and not to the TR epitope. This could be related to diversity in the TR of TRP47, which has been described in Arkansas and Supulpa strains (Doyle et al., 2006; Yu et al., 2007). This is in contrast to other TRPs, such as TRP120 and TRP32, in which the TR epitopes appear to be more conserved (Yabsley et al., 2003; Yu et al., 2007). Therefore, the increased sensitivity attained with a peptide mixture containing all TRP47 epitopes compared to the TR epitope alone, is likely related to antigenic diversity of this protein. Additional characterization of TRP47 variants could provide an explanation for the decreased sensitivity of this protein compared to TRP120 or TRP32 as well as information regarding the kinetics of the antibody response in HME patients.

All of the Ehrlichial major immunoreactive protein orthologs (TRP32/TRP19, TRP47/TRP36, and TRP120/TRP140) identified and characterized recently are antigenically distinct and elicit species-specific antibodies (Doyle et al., 2006; Luo et al., 2009; Luo et al., 2008; McBride et al., 2007). Five major antibody epitopes characterized in *E. canis* Ank200 are also molecularly distinct (Nethery et al., 2007). Consistent with these findings, the amino acid alignments of the mapped epitopes in Ank200 identified no significant homology with *E. canis* Ank200 or other proteins from organisms in closely related genera; moreover, antisera against recombinant *E. chaffeensis* or *E. canis* Ank200N did not cross-react, indicating that these epitopes appear to be primarily species-specific and could be utilized for species-specific diagnostic development. The inventors have previously reported that minor antibody epitope-containing regions in the N- and C-termini of *E. chaffeensis* TRP120 and *E. canis* TRP140 are cross-reactive, further suggesting that cross-reactive antibodies generated between closely related *Ehrlichia* spp. were directed at some minor epitopes rather than major epitopes (Luo et al., 2009).

Previous studies have concluded that the TRP120 is a sensitive immunodiagnostic antigen for HME (Yu et al., 1999). The data presented in this Example indicates that the TRP120 is the most sensitive immunodiagnostic antigen for HME. It is becoming increasingly evident that all of the major immunoreactive proteins of *Ehrlichia* spp. have molecularly distinct epitopes, which can be used to serologically identify etiologic agents, a task that has been routinely difficult or impossible to accomplish (Doyle et al., 2006; Luo et al., 2009; Luo et al., 2008; McBride et al., 2007; Nethery et al., 2007). The TRP epitopes are molecularly distinct and therefore, serologic responses specific to *E. chaffeensis* can be distinguished from those against closely related agents or conserved bacterial proteins using these immunodeterminants. The inventors determined serologically that TRP120-R-I$_1$ is a species-specific epitope, and lack of serologic cross-reactivity with *E. canis* was related to divergence at the amino acid level (Luo et al., 2009). In addition, the TRP120 has very limited amino acid homology with two *A. phagocytophilum* repeat-containing proteins, GE100 and GE130; however, the TRP120-R-I$_1$ peptide does not have any amino acid homology with these two proteins (Storey et al., 1998). Compared with TRP32 and TRP47, the TRP120 has less molecular variation among examined *E. chaffeensis* strains, and this trait is shared with an ortholog, *E. canis* TRP140 (Yu et al., 2007). However, as observed with other immunoreactive peptides from *Ehrlichia*, in some cases, but not all, a mixture of TRP120 and TRP32 peptides does not provide enhanced sensitivity over the TRP120 alone, indicating that mixed peptides could compete with each other resulting in decreased sensitivity. To the inventor's knowledge, this is the first study to compare multiple molecularly-defined major antibody epitopes of *E. chaffeensis* for serodiagnosis of HME in a solid phase assay. The synthetic TRP120-R-I$_1$ peptide exhibited even more sensitive reactivity than the recombinant TRP120-TR with patient sera, indicating that high purity of the immunodeterminant may contribute to enhanced sensitivity of ELISA and could effectively replace recombinant proteins.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,814,097
U.S. Pat. No. 3,964,482
U.S. Pat. No. 4,220,450
U.S. Pat. No. 4,373,071
U.S. Pat. No. 4,373,932
U.S. Pat. No. 4,401,796
U.S. Pat. No. 4,458,066
U.S. Pat. No. 4,472,509
U.S. Pat. No. 4,598,049
U.S. Pat. No. 4,897,268
U.S. Pat. No. 4,938,948
U.S. Pat. No. 5,075,109
U.S. Pat. No. 5,440,013
U.S. Pat. No. 5,446,128
U.S. Pat. No. 5,470,723
U.S. Pat. No. 5,470,932
U.S. Pat. No. 5,475,085
U.S. Pat. No. 5,543,504
U.S. Pat. No. 5,552,157
U.S. Pat. No. 5,565,213
U.S. Pat. No. 5,567,434
U.S. Pat. No. 5,618,914
U.S. Pat. No. 5,656,016
U.S. Pat. No. 5,670,155
U.S. Pat. No. 5,672,681
U.S. Pat. No. 5,674,976
U.S. Pat. No. 5,697,899
U.S. Pat. No. 5,710,245
U.S. Pat. No. 5,738,868
U.S. Pat. No. 5,741,516
U.S. Pat. No. 5,770,219
U.S. Pat. No. 5,779,708
U.S. Pat. No. 5,783,208
U.S. Pat. No. 5,795,587
U.S. Pat. No. 5,797,898
U.S. Pat. No. 5,840,833
U.S. Pat. No. 5,853,744
U.S. Pat. No. 5,859,184
U.S. Pat. No. 5,891,506
U.S. Pat. No. 5,929,237
U.S. Pat. No. 6,136,610

U.S. Pat. No. 6,210,708
U.S. Pat. No. 6,372,445
U.S. Pat. No. 6,617,142
U.S. Pat. No. 6,875,750
U.S. Pat. No. 6,951,765
U.S. Pat. No. 7,163,677
U.S. Pat. No. 7,282,194
U.S. Pat. No. 7,344,893
U.S. Pat. No. 7,371,582
U.S. Patent Appln. 2005/0047972
U.S. Patent Appln. 2005/0065463
U.S. Patent Appln. 2005/0250141
U.S. Patent Appln. 2007/0264664
U.S. Patent Appln. 2009/0005535
Allred et al., *Proc. Natl. Acad. Sci. USA*, 87:3220-3224, 1990.
Atherton and Sheppard, In: *Solid Phase peptide synthesis: a practical approach*, Oxford, England, IRL Press, 1989.
Carpenter et al., *J. Infect. Dis.*, 180:900-903, 1999.
Carpino et al., *Org. Proc. Res. Dev.*, 7(1)28-37, 2003.
Carpino, *J. Am. Chem. Soc.*, 115 (10):4397-4398, 1993.
Chen et al., *Am. J. Trop. Med. Hyg.*, 50:52-58, 1994.
Chen et al., *Clin. Diagn. Lab Immunol.*, 4:731-735, 1997.
Childs et al., *J. Clin. Microbiol.*, 37:2997-3000, 1999.
Collins et al., *Proc. Natl. Acad. Sci. USA*, 102(3):838-43, 2005 corner et al., *J. Clin. Microbiol.*, 37:558-564, 1999.
Doyle et al., *Infect. Immun.*, 74:711-720, 2006.
Dumler et al., *Clin. Infect. Dis.*, 45:S45-S51, 2007.
Feng and Walker, *Infect. Immun.*, 72:966-971, 2004.
Frutos et al., *Ann. NY Acad. Sci.*, 1081:417-33, 2006.
Garcia-Ortega et al., *Electrophoresis*, 26:3407-3413, 2005.
Geysen et al., *Proc. Natl. Acad. Sci. USA*, 81(13):3998-4002, 1984.
Goeddel, *Methods Enzymol.*, 185:3-7, 1990.
Graceffa et al., *Arch. Biochem. Biophys.*, 297:46-51, 1992.
Henry et al., *J. Pharm. Sci.*, 87(3), 922-925, 1998.
Hotopp et al. *PLoS Genet.* 2(2):e21, 2006.
*J. Biol. Chem.*, 243:3552-59, 1969.
Johannesson et al. *J. Med. Chem.*, 42(22):4524-4537, 1999.
Johnson et al., In: *Biotechnology And Pharmacy*, Pezzuto et al. (Eds.), Chapman and Hall, N.Y., 1993.
Li et al., *J. Immunol.*, 169:1419-1425, 2002.
Li et al., *Vaccine*, 26:6945-6949, 2008.
Luo et al., *Infect. Immun.*, 76:1572-1580, 2008.
Mavromatis et al., *J. Bacteriol.*, 188(11):4015-4023, 2006.
McBride et al., *Ann. NY Acad. Sci.*, 990:678-684, 2003.
McBride et al., *Infect. Immun.*, 68:13-18, 2000.
McBride et al., *Infect. Immun.*, 71:2516-2524, 2003.
McBride et al., *Infect. Immun.*, 75:74-82, 2007.
McBride et al., *J. Clin. Microbiol.*, 39:315-322, 2001.
McBride et al., *J. Vet. Diagn. Invest.*, 8:441-447, 1996.
Merrifield, *J. Am. Chem. Soc.*, 85(14):2149-2154, 1963.
Nethery et al., *Infect. Immun.*, 75:4900-4908, 2007.
Park et al., *Cell Microbiol.*, 6:743-751, 2004.
Popov et al., *Microb. Pathog.*, 28:71-80, 2000.
Remington's Pharmaceutical Sciences, 18th Ed. Mack Printing Company, 1289-1329, 1990.
Remington: The Science and Practice of Pharmacy, $21^{st}$ Ed. Lippincott Williams and Wilkins, 2005
Rikihisa et al., *J. Clin. Microbiol.*, 30:143-148, 1992.
Rikihisa et al., *J. Clin. Microbiol.*, 32:2107-2112, 1994.
Storey et al., *Infect. Immun.*, 66:1356-1363, 1998.
Sumner et al. *J Clin Microbiol.* 37(5):1447-53, 1999.
Wakeel et al., *Infect. Immun.*, 77(5):1734-1745, 2009.
Walker and Task Force on Consensus Approach for Ehrlichiosis, In: *Diagnosing human ehrlichioses: current status and recommendations*, ASM News, 66:287-290, 2000.
Weisshoff et al., *Eur. J. Biochem.*, 259(3):776-788, 1999.
Winslow et al., *Ann. NY Acad. Sci.*, 990:435-443, 2003.
Winslow et al., *Curr. Opin. Infect. Dis.*, 18:217-221, 2005.
Winslow et al., *Infect. Immun.*, 68:2187-2195, 2000.
Yabsley et al., *J. Clin. Microbiol.*, 41:5202-5206, 2003.
Yager et al., *Infect. Immun.*, 73:8009-8016, 2005.
Yu et al., *Gene*, 184:149-154, 1997.
Yu et al., *J. Clin. Microbiol.*, 34:2853-2855, 1996.
Yu et al., *J. Clin. Microbiol.*, 37:2568-2575, 1999.
Yu et al., *J. Clin. Microbiol.*, 38:369-374, 2000.
Yu et al., *Vet. Parasitol.*, 143:337-346, 2007.
Zhang et al., *Clin. Vaccine Immunol.*, 15:1080-1088, 2008.
Zhu et al., *Infect. Immun.*, 77:4243-4255, 2009.

What is claimed is:

1. An isolated peptide 45 amino acids or less in length, wherein the peptide comprises SEQ ID NO: 1 or, an isolated peptide 30 amino acids or less in length, wherein the peptide comprises SEQ ID NO: 2, wherein the peptide selectively binds to an antibody that recognizes and binds to an *Ehrlichia* p120 or p140 protein.

2. The peptide of claim 1, wherein the peptide is from 20 to 30 amino acids in length.

3. The peptide of claim 1, wherein the peptide consists of SEQ ID NO:1 or SEQ ID NO:2.

4. The peptide of claim 1, wherein the isolated peptide is immobilized on a surface of a support substrate.

5. The peptide of claim 4, wherein said support substrate comprises latex, polystyrene, nylon, nitrocellulose, cellulose, silica, agarose, or magnetic resin.

6. The peptide of claim 4, wherein the support substrate is a reaction chamber, a well, a membrane, a filter, a paper, an emulsion, a bead, a microbead, a dipstick, a card, a glass slide, a lateral flow apparatus, a microchip, a comb, a silica particle, a magnetic particle, a nanoparticle, or a self-assembling monolayer.

7. The peptide of claim 1, wherein the peptide is comprised in a kit.

8. The peptide of claim 1, wherein the peptide is comprised in a pharmaceutical preparation.

9. The peptide of claim 1, wherein the peptide was produced via peptide synthesis.

10. The peptide of claim 1, wherein the peptide was recombinantly produced.

11. The peptide of claim 1, wherein the isolated peptide further comprises a detectable label.

12. A kit comprising: (a) the isolated peptide of claim 1, (b) an anti-dog or anti-human secondary antibody linked to a reporter molecule; and, (c) an appropriate reagent for detection of the reporter molecule.

13. The kit of claim 12, wherein the peptide is immobilized on a membrane or a microtiter plate.

14. The kit of claim 13, wherein the reporter molecule is selected from the group consisting of luciferase, horseradish peroxidase, P-galactosidase, and a fluorescent label.

15. The kit of claim 12, wherein the kit further comprises a dilution buffer for dog or human serum.

16. The kit of claim 12, wherein the kit comprises a lateral flow immunoassay or a lateral flow immunochromatographic assay.

17. The kit of claim 12, wherein the kit comprises an enzyme-linked immunosorbent assay (ELISA).

* * * * *